US010657423B2

(12) United States Patent
Reeves

(10) Patent No.: US 10,657,423 B2
(45) Date of Patent: May 19, 2020

(54) METHODS FOR USING FEATURE VECTORS AND MACHINE LEARNING ALGORITHMS TO DETERMINE DISCRIMINANT FUNCTIONS OF MINIMUM RISK LINEAR CLASSIFICATION SYSTEMS

(71) Applicant: Denise Reeves, Burke, VA (US)

(72) Inventor: Denise Reeves, Burke, VA (US)

( * ) Notice: Subject to any disclaimer, the term of this patent is extended or adjusted under 35 U.S.C. 154(b) by 0 days.

(21) Appl. No.: 16/523,793

(22) Filed: Jul. 26, 2019

(65) Prior Publication Data

US 2019/0347572 A1    Nov. 14, 2019

Related U.S. Application Data

(63) Continuation-in-part of application No. 15/853,787, filed on Dec. 23, 2017, now abandoned.
(Continued)

(51) Int. Cl.
*G06K 9/62* (2006.01)
*G06N 20/00* (2019.01)
(Continued)

(52) U.S. Cl.
CPC .......... *G06K 9/6278* (2013.01); *A61B 5/7264* (2013.01); *A61B 5/7267* (2013.01);
(Continued)

(58) Field of Classification Search
CPC .... G06K 9/626; G06K 9/6261; G06K 9/6267; G06K 9/6268; G06K 9/6277;
(Continued)

(56) References Cited

U.S. PATENT DOCUMENTS 5,835,901 A * 11/1998 Duvoisin, III ......... G06K 9/627
706/19
6,760,715 B1 * 7/2004 Barnhill ............... G06K 9/6256
706/16
(Continued)

FOREIGN PATENT DOCUMENTS

JP    2012181579 A  *  9/2012

OTHER PUBLICATIONS

Yang et al.; "A Novel Multi-Surface Proximal Support Vector Machine Classification Model Incorporating Feature Selection"; Jul. 2009; 2009 International Conference on Machine Learning and Cybernetics; pp. 943-947 (Year: 2009).*
(Continued)

*Primary Examiner* — John Villecco

(57) ABSTRACT

Methods are provided for determining discriminant functions of minimum risk linear classification systems, wherein a discriminant function is represented by a geometric locus of a principal eigenaxis of a linear decision boundary. A geometric locus of a principal eigenaxis is determined by solving a system of fundamental locus equations of binary classification, subject to geometric and statistical conditions for a minimum risk linear classification system in statistical equilibrium. Feature vectors and machine learning algorithms are used to determine discriminant functions and ensembles of discriminant functions of minimum risk linear classification systems, wherein distributions of the feature vectors have similar covariance matrices, and wherein a discriminant function of a minimum risk linear classification system exhibits the minimum probability of error for classifying given collections of feature vectors and unknown feature vectors related to the collections.

6 Claims, 12 Drawing Sheets

Related U.S. Application Data

(60) Provisional application No. 62/556,185, filed on Sep. 8, 2017.

(51) Int. Cl.
*G06F 17/18* (2006.01)
*A61B 5/00* (2006.01)
*G06F 17/11* (2006.01)

(52) U.S. Cl.
CPC .............. *G06F 17/11* (2013.01); *G06F 17/18* (2013.01); *G06K 9/6265* (2013.01); *G06K 9/6277* (2013.01); *G06K 9/6286* (2013.01); *G06N 20/00* (2019.01)

(58) Field of Classification Search
CPC .... G06K 9/6278; G06K 9/6279; G06K 9/628; G06K 9/6281; G06K 9/6285; G06K 9/6286; G06N 20/00; G06F 17/18; G06F 17/11; A61B 5/7264; A61B 5/7267
See application file for complete search history.

(56) References Cited

U.S. PATENT DOCUMENTS

| | | | | |
|---|---|---|---|---|
| 7,010,167 | B1* | 3/2006 | Ordowski | G06K 9/6267 345/644 |
| 7,305,132 | B2* | 12/2007 | Singh | G06K 9/6232 382/224 |
| 7,529,666 | B1* | 5/2009 | Padmanabhan | G06K 9/623 704/231 |
| 7,624,074 | B2* | 11/2009 | Weston | G06N 20/00 706/1 |
| 7,660,775 | B2* | 2/2010 | Bougaev | G06N 7/005 706/20 |
| 7,961,955 | B1* | 6/2011 | Minter | G06K 9/6247 382/159 |
| 7,961,956 | B1* | 6/2011 | Minter | G06K 9/6234 382/159 |
| 7,979,363 | B1* | 7/2011 | Minter | G06N 7/005 706/12 |
| 7,983,490 | B1* | 7/2011 | Minter | G06K 9/6226 382/159 |
| 8,527,432 | B1* | 9/2013 | Guo | G06N 20/00 706/12 |
| 9,189,735 | B2* | 11/2015 | Ni | G06N 5/02 |
| 9,406,030 | B2* | 8/2016 | Dolev | G06K 9/00442 |
| 9,449,260 | B2* | 9/2016 | He | G06K 9/6256 |
| 2003/0216916 | A1* | 11/2003 | Navratil | G10L 17/06 704/250 |
| 2008/0086493 | A1* | 4/2008 | Zhu | G06F 16/2462 |
| 2008/0301077 | A1* | 12/2008 | Fung | G16H 50/20 706/46 |
| 2010/0082639 | A1* | 4/2010 | Li | G06F 16/334 707/748 |
| 2017/0154209 | A1* | 6/2017 | Nakano | G06K 9/00255 |
| 2019/0108423 | A1* | 4/2019 | Jones | G06K 9/00288 |

OTHER PUBLICATIONS

Ekmekci et al.; "Classifier Combination with Kernelized Eigenclassifiers"; Jul. 2013, International Society of Information Fusion; pp. 743-479 (Year: 2013).*

Reeves, Denise; "Design and Development of Bayes' Minimax Linear Classification Systems"; Dec. 13, 2016, arXiv: 1612.03902v2; pp. 1-122 (Year: 2016).*

Reeves, Denise; "Design of Data-Driven Mathematical Laws for Optimal Statistical Classification Systems"; May 12, 2018; arXiv: 1612.03902v9; pp. 1-339 (Year: 2018).*

Kittler et al.; "Discriminant Function Implementation of a Minimum Risk Classifier"; May 1975; Biological Cybernetics; vol. 18, Issue 3-4, pp. 169-179; <https://doi.org/10.1007/BF00326687> (Year: 1975).*

Aksu et al.; "Margin-Maximizing Feature Elimination Methods for Linear and Nonlinear Kernel-Based Discriminant Functions"; May 2010; IEEE Transactions on Neural Networks, vol. 21, No. 5; pp. 701-717 (Year: 2010).*

Reeves, Denise; "Resolving the Geometric Locus Dilemma for Support Vector Learning Machines"; Nov. 2015; arXiv:1511.05102v1; pp. 1-170 (Year: 2015).*

* cited by examiner

A: linear decision boundary
B: linear decision border
C: linear decision border

1: region of counter risk in decision region $Z_2$
2: region of counter risk in decision region $Z_1$
3: region of risk in decision region $Z_2$
4: region of risk in decision region $Z_1$

METHODS FOR USING FEATURE VECTORS AND MACHINE LEARNING ALGORITHMS TO DETERMINE DISCRIMINANT FUNCTIONS OF MINIMUM RISK LINEAR CLASSIFICATION SYSTEMS

CROSS-REFERENCES TO RELATED APPLICATIONS

This application claims the benefit of U.S. provisional application No. 62/556,185, filed Sep. 8, 2017.

FIELD OF THE INVENTION

This invention relates generally to learning machines and statistical pattern recognition systems. More particularly the invention relates to using feature vectors and machine learning algorithms to determine discriminant functions of minimum risk linear classification systems. The invention is described in an article by applicant, "Design of Data-Driven Mathematical Laws for Optimal Statistical Classification Systems," arXiv: 1612.03902v8: submitted on 22 Sep. 2017.

BACKGROUND OF THE INVENTION

The design of statistical pattern recognition systems is important for a wide variety of statistical classification problems including, but not limited to: seismic signal analysis for geophysical exploration, radar signal analysis for weather radar systems and military applications, analysis of biomedical signals for medical and physiological applications, classification of objects in images, optical character recognition, speech recognition, handwriting recognition, face recognition, and fingerprint classification.

The statistical pattern recognition problem involves classifying a pattern into one of several classes by processing features associated with the pattern, wherein a pattern is determined by numerical features that have been extracted from a digital signal associated with one of the problems similar to those outlined above. Numerical features can be extracted from a variety of digital signals, e.g., seismic signals, radar signals, speech signals, biomedical signals, images of objects, hyperspectral images or multispectral images. For a given type of digital signal, thousands of numerical features are available, wherein numerical features are extracted by computer-implemented methods.

An important attribute of statistical pattern recognition systems involves learning from a set of training patterns, wherein a training pattern is represented by a d-dimensional vector of numerical features. Given a set of training patterns from each pattern class, the primary objective is to determine decision boundaries in a corresponding feature space that separate patterns belonging to different pattern classes. In the statistical decision theoretic approach, the decision boundaries are determined by the probability distributions of the feature vectors belonging to each category, wherein the probability distributions determine the structure of a discriminant function and the probability distributions must be specified or learned.

In the discriminant analysis-based approach, a parametric form of the decision boundary is specified, e.g., a linear or quadratic form, and the best decision boundary of the specified form is found based on the classification of the training patterns. For example, support vector machines learn decision boundaries from training patterns, wherein the capacity of a linear or nonlinear decision boundary is regulated by a geometric margin of separation between a pair of margin hyperplanes.

The computer-implemented design of a discriminant function of a classification system involves two fundamental problems: (1) the design of numerical features of the objects being classified for the different classes of objects, and (2) the computer-implemented design of the discriminant function of the classification system.

For M classes of feature vectors, the feature space of a classification system is composed of M regions of feature vectors, wherein each region contains feature vectors that belong to one of the M classes. The design of a computer-implemented discriminant function involves designing a computer-implemented method that uses feature vectors to determine discriminant functions which generate decision boundaries that divide feature spaces into M suitable regions, wherein a suitable criterion is necessary to determine the best possible partitioning for a given feature space.

The no-free-lunch theorem for supervised learning demonstrates that there is a cost associated with using machine learning algorithms to determine discriminant functions of classification systems. Criteria of performance for a classification system must be chosen, and a class of acceptable classification systems must be defined in terms of constraints on design and costs. Finally, a classification system can be determined within the specified class—which is best in terms of the selected criteria—by an extremum of an objective function of an optimization problem that satisfies the criteria of performance and the constraints on the design and costs.

Suppose that a theoretical model of a discriminant function of a classification system can be devised from first principles, wherein the structure and the properties of the theoretical model satisfy certain geometric and statistical criteria. The no-free-lunch theorem for supervised learning suggests that the best parametric model of the classification system matches the theoretical model, wherein the structure and the properties of the parametric model are determined by geometric and statistical criteria satisfied by the theoretical model.

What would be desired is to (1) devise a theoretical model of a discriminant function of a binary classification system, wherein the discriminant function of the binary classification system exhibits certain geometric and statistical properties and is represented by a geometric and statistical structure that satisfies certain geometric and statistical criteria, and (2) devise a parametric model of a discriminant function of a binary classification system that matches the theoretical model, wherein the structure and the properties of the parametric model satisfy fundamental geometric and statistical criteria of the theoretical model, wherein the discriminant function is represented by a geometric and statistical structure that matches the structure exhibited by the theoretical model and also exhibits fundamental geometric and statistical properties of the theoretical model, and (3) discover or devise an algorithm for which criteria of performance satisfy fundamental geometric and statistical criteria of the theoretical model of a discriminant function of a binary classification system, wherein a class of discriminant functions of binary classification systems are defined in terms of an objective function of an optimization problem that satisfies fundamental geometric and statistical conditions and costs.

In particular, it would be advantageous to devise a computer-implemented method for using feature vectors and machine learning algorithms to determine a discriminant function of a minimum risk linear classification system that classifies the feature vectors into two classes, wherein the feature vectors have been extracted from digital signals such as seismic signals, radar signals, speech signals, biomedical signals, fingerprint images, hyperspectral images, multi-spectral images or images of objects, and wherein the minimum risk linear classification system exhibits the minimum probability of error for classifying the feature vectors into the two classes.

Further, it would be advantageous if discriminant functions of minimum risk linear classification systems can be combined additively, wherein M ensembles of M−1 discriminant functions of M−1 minimum risk linear classification systems determine a discriminant function of an M-class minimum risk linear classification system that classifies feature vectors into M classes. It would also be advantageous to devise a method that determines a fused discriminant function of a fused minimum risk linear classification system that classifies different types of feature vectors into two classes, wherein different types of feature vectors have different numbers of vector components and may be extracted from different types of digital signals. Further, it would be advantageous to extend the method to M classes of feature vectors. Finally, it would be advantageous to devise a method that uses a discriminant function of a minimum risk linear classification system to determine a classification error rate and a measure of overlap between distributions of feature vectors for two classes of feature vectors, wherein the distributions of feature vectors have similar covariance matrices. A similar method could be used to determine if distributions of two collections of feature vectors are homogenous distributions.

SUMMARY OF THE INVENTION

The present invention involves the mathematical discovery of a theoretical model and a parametric model of a discriminant function of a minimum risk linear classification system that match each other. Both models are both determined by a system of fundamental locus equations of binary classification, subject to geometric and statistical conditions for a minimum risk linear classification system in statistical equilibrium.

An important aspect of both models involves the general idea of a geometric locus. The general idea of a curve or surface which at any point of it exhibits some uniform property is expressed in geometry by the term locus. Generally speaking, a geometric locus is a curve or surface formed by points, wherein each point on the geometric locus possesses some uniform property that is common to all points on the locus—and no other points. Any given curve or surface must pass through each point on a specified locus, and each point on the specified locus must satisfy certain geometric conditions. For example, a circle is a locus of points, all of which are at the same distance (the radius) from a fixed point (the center).

Any given geometric locus is determined by an equation, wherein the locus of the equation is the location of all those points whose coordinates are solutions of the equation. Classic geometric locus problems involve algebraic equations of conic sections or quadratic surfaces, wherein the algebraic form of an equation is determined by the geometric property and the Cartesian coordinate system of the locus. Finding the form of an equation for a geometric locus is often a difficult problem. The central problem involves identifying the geometric property exhibited by a certain locus of points. The inverse problem involves finding the form of an equation whose solution determines coordinates of all of the points on a locus that has been defined geometrically.

Another aspect of both models involves the idea of an extreme point. Take a collection of feature vectors for any two pattern classes that are drawn from any two statistical distributions, wherein the distributions are either overlapping or non-overlapping with each other. An extreme point is defined to be a feature vector that exhibits a high variability of geometric location, wherein the feature vector is located (1) relatively far from its distribution mean, (2) relatively close to the mean of the other distribution, and (3) relatively close to other extreme points. Accordingly, any given extreme point exhibits a large covariance, wherein the extreme point is located somewhere within an overlapping region or near a tail region between two distributions.

Given the geometric and statistical properties exhibited by the locus of an extreme point, it follows that a collection of extreme vectors determine principal directions of large covariance for a given collection of feature vectors, wherein extreme vectors are discrete principal components that specify directions for which the collection of feature vectors is most variable or spread out.

Further, decision regions of minimum risk linear classification systems are determined by distributions of extreme points, wherein the distributions have similar covariance matrices, and wherein positions and potential locations of extreme points determine regions of counter risk and risk associated with making right and wrong decisions.

The theoretical model of the invention demonstrates that a discriminant function of a minimum risk linear classification system is represented by a certain geometric and statistical structure, wherein the structure is the principal eigenaxis of a decision boundary of a minimum risk linear classification system. The principal eigenaxis is expressed as a dual locus of likelihood components and principal eigenaxis components and is determined by a geometric locus of signed and scaled extreme points, wherein likelihood components determine likelihoods for extreme points and principle eigenaxis components determine an intrinsic coordinate system of the geometric locus of a linear decision boundary.

The theoretical model also demonstrates that a minimum risk linear classification system seeks a point of statistical equilibrium, wherein conditional probabilities and critical minimum eigenenergies exhibited by the system are symmetrically concentrated, and wherein opposing and counteracting random forces and influences of the system are symmetrically balanced with each other, wherein the total allowed eigenenergy and the expected risk exhibited by the minimum risk linear classification system are minimized and the minimum risk linear classification system exhibits the minimum probability of error. However, the theoretical model does not provide a constructive proof for finding the point of statistical equilibrium that is sought by a minimum risk linear classification system—nor does it define its parametric form. Further, suitable models for equilibrium points of minimum risk linear classification systems cannot be found with analytical or numerical methods.

A discriminant function of a minimum risk linear classification system of the invention is determined by using feature vectors and machine learning algorithms of the invention, wherein for a given machine learning algorithm and a given collection of feature vectors, a discriminant function of a minimum risk linear classification system is determined by using the processors of a computer system to find a satisfactory solution of a certain dual optimization problem, wherein the discriminant function of the minimum risk linear classification system satisfies a system of fundamental locus equations of binary classification, subject to geometric and statistical conditions for a minimum risk linear classification system in statistical equilibrium.

One aspect of the principles of the invention provides a method for determining a discriminant function of a minimum risk linear classification system that classifies feature vectors into two classes, wherein the minimum risk linear classification system exhibits the minimum probability of error for classifying a collection of feature vectors that belong to the two classes and unknown feature vectors related to the collection.

Another aspect provides a method for determining a discriminant function of an M–class minimum risk linear classification system that classifies feature vectors into M classes, wherein the minimum risk linear classification system exhibits the minimum probability of error for classifying a collection of feature vectors that belong to the M classes and unknown feature vectors related to the collection of feature vectors. Yet another aspect provides a method for using a discriminant function of a minimum risk linear classification system to determine a classification error rate and a measure of overlap between distributions of feature vectors for two classes of feature vectors, wherein the distributions have similar covariance matrices. Additional aspects will become apparent in view of the following descriptions.

The innovative concept of the invention is a novel geometric and statistical structure that determines a discriminant function of a minimum risk linear classification system that classifies feature vectors into two classes along with the geometric and statistical architecture of a learning machine. The novel geometric and statistical structure is the principal eigenaxis of the decision boundary of the minimum risk linear classification system, wherein the principal eigenaxis determines an intrinsic coordinate system and an eigenaxis of symmetry for the decision space of the minimum risk linear classification system, wherein all of the points on a linear decision boundary and corresponding decision borders exclusively reference the principal eigenaxis, and wherein likelihoods are symmetrically distributed over the sides of the principal eigenaxis, wherein likelihoods determine conditional likelihoods for feature vectors—termed extreme vectors—that are located within overlapping regions or near tail regions of distributions of two given collections of feature vectors that belong to the two classes.

The discriminant function of the minimum risk linear classification system determines likely locations of feature vectors according to vector projections of the feature vectors along the eigenaxis of symmetry, wherein the vector projection of a feature vector along the principal eigenaxis accounts for the distance between the feature vector and the average extreme vector of the collection of feature vectors, and wherein the vector projection of the feature vector along the eigenaxis of symmetry determines a region of the decision space that the feature vector is located within, wherein the region is related to one of the two classes, and wherein the scalar projection of the feature vector along the eigenaxis of symmetry determines a signed magnitude related to one of the two classes.

The principal eigenaxis of the invention is determined by a geometric locus of signed and scaled extreme points, wherein the geometric locus of the principal eigenaxis is expressed as a dual locus of likelihood components and principal eigenaxis components, wherein likelihood components on the dual locus determine conditional likelihoods for extreme points that belong to the two classes, and wherein principal eigenaxis components on the dual locus determine the intrinsic coordinate system and the corresponding eigenaxis of symmetry for the decision space of the minimum risk linear classification system.

The minimum risk linear classification system is in statistical equilibrium, wherein the linear classification system exhibits the minimum probability of classification error for the given collection of feature vectors, in accordance with the principal eigenaxis of the linear decision boundary of the system, wherein conditional probabilities and critical minimum eigenenergies exhibited by the linear classification system are concentrated.

The geometric locus of signed and scaled extreme points satisfies a computer-implemented system of fundamental locus equations of binary classification, subject to geometric and statistical conditions for a minimum risk linear classification system in statistical equilibrium, wherein the principal eigenaxis of the linear decision boundary is in statistical equilibrium, wherein conditional probabilities and critical minimum eigenenergies exhibited by the minimum risk linear classification system are symmetrically concentrated within the geometric locus of the principal eigenaxis, and wherein counteracting and opposing components of conditional probabilities and total allowed eigenenergies exhibited by the minimum risk linear classification system are symmetrically balanced with each other within the geometric locus, wherein corresponding counter risks and risks of the minimum risk linear classification system are symmetrically balanced with each other about the geometric center of the geometric locus of the principal eigenaxis. Further, the computer-implemented system matches a theoretical system that has been devised.

The principal eigenaxis of the linear decision boundary exhibits symmetrical dimensions and density, wherein counteracting and opposing components of likelihood components and principal eigenaxis components are symmetrically distributed over either side of the dual locus, wherein conditional probabilities and critical minimum eigenenergies exhibited by the minimum risk linear classification system are symmetrically concentrated, and wherein counteracting and opposing components of critical minimum eigenenergies exhibited by all of the scaled extreme vectors on the dual locus together with corresponding counter risks and risks exhibited by the minimum risk linear classification system are symmetrically balanced with each other about the geometric center of the dual locus, and wherein the center of total allowed eigenenergy and minimum expected risk of the minimum risk linear classification system is at the geometric center of the dual locus of likelihood components and principal eigenaxis components, wherein the minimum risk linear classification system satisfies a state of statistical equilibrium, wherein the total allowed eigenenergy and the expected risk of the system are minimized, and wherein the minimum risk linear classification system exhibits the minimum probability of error for classifying the given collection of feature vectors and feature vectors related to the given collection.

DETAILED DESCRIPTION OF THE INVENTION

Figure 1:
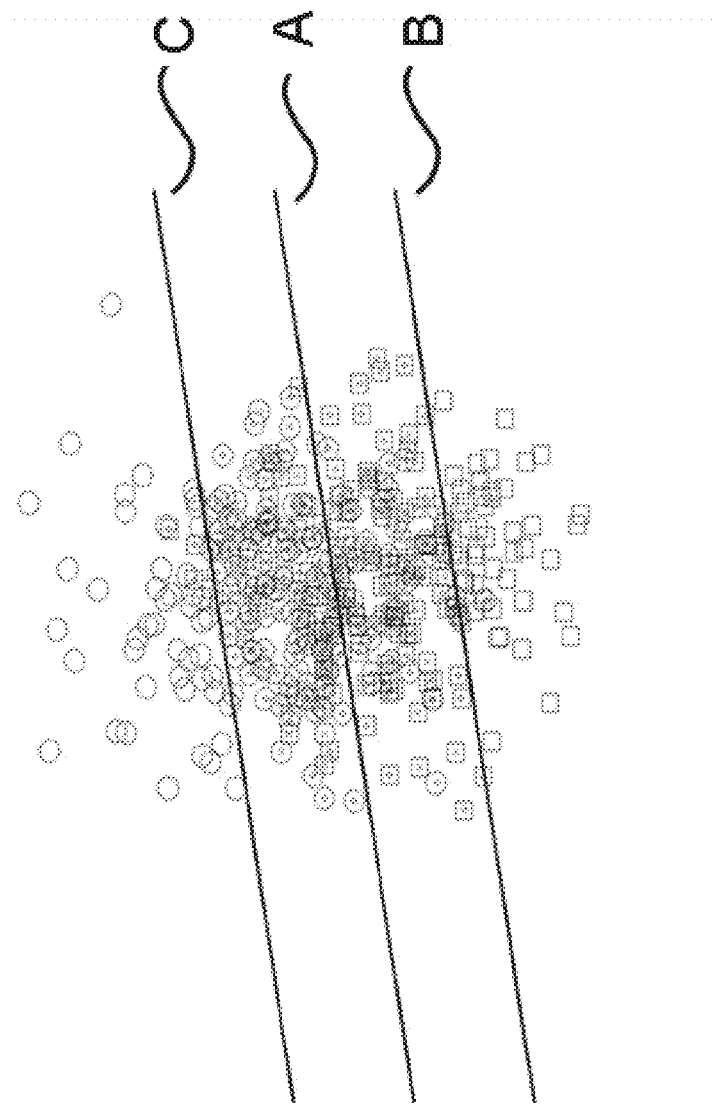
FIG. 1 illustrates symmetrical decision regions of a minimum risk linear classification system that are delineated by a linear decision boundary and linear decision borders obtained by using the method for determining a discriminant function of a minimum risk linear classification system that classifies feature vectors into two classes in which distributions of two collections of feature vectors have different mean vectors and similar covariance matrices and are overlapping with each other.

Before describing illustrative embodiments of the invention, a detailed description of machine learning algorithms of the invention is presented along with a detailed description of the novel principal eigenaxis that determines a discriminant function of a minimum risk linear classification system.

The method to determine a discriminant function of a minimum risk linear classification system that classifies feature vectors into two categories, designed in accordance with the invention, uses machine learning algorithms and labeled feature vectors to determine a geometric locus of signed and scaled extreme points for feature vectors x of dimension d belonging to either of two classes A or B, wherein the geometric locus satisfies a system of fundamental locus equations of binary classification, subject to geometric and statistical conditions for a linear classification system in statistical equilibrium.

The input to a machine learning algorithm of the invention is a collection of N feature vectors $x_i$ with labels $y_i$ $$(x_1,y_1),(x_2,y_2),\ldots,(x_N,y_N)$$

wherein $y_i=+1$ if $x_i \in A$ and $y_i=-1$ if $x_i \in B$, and wherein the N feature vectors are extracted from collections of digital signals.

Denote a minimum risk linear classification system of the invention by $$s^T \tau + \tau_0 \underset{B}{\overset{A}{\gtreqless}} 0,$$

wherein A or B is the true category. The discriminant function $D(s)=s^T\tau+\tau_0$ of the minimum risk linear classification system is represented by a novel principal eigenaxis that is expressed as a dual locus of likelihood components and principal eigenaxis components and is determined by a geometric locus of signed and scaled extreme points:

$$\tau = \tau_1 - \tau_2 = \sum_{i=1}^{l_1} \psi_{1i*} x_{1i*} - \sum_{i=1}^{l_2} \psi_{2i*} x_{2i*},$$

wherein $x_{1i*}$ and $x_{2i*}$ are extreme points located within overlapping regions or near tail regions of distributions of the N feature vectors, wherein the distributions have similar covariance matrices, and wherein $\tau_1-\tau_2$ determines an intrinsic coordinate system of geometric loci of a linear decision boundary and corresponding decision borders that jointly partition the decision space of the minimum risk linear classification system into symmetrical decision regions, wherein $$\left(s - \frac{1}{l}\sum_{i=1}^{l} x_{i*}\right)^T (\tau_1 - \tau_2)$$

determines an eigenaxis of symmetry for the decision space, and wherein the scale factors $\psi_{1i*}$ and $\psi_{2i*}$ determine magnitudes $\|\psi_{1i*}x_{1i*}\|$ and $\|\psi_{2i*}x_{2i*}\|$ as well as critical minimum eigen energies $\|\psi_{1i*}x_{1i*}\|_{min_c}^2$ and $\|\psi_{2i*}x_{2i*}\|_{min_c}^2$ exhibited by respective principal eigenaxis components $\psi_{1i*}x_{1i*}$ and $\psi_{2i*}x_{2i*}$ on $\tau_1-\tau_2$, and determine conditional likelihoods for respective extreme points $x_{1i*}$ and $x_{2i*}$.

A machine learning algorithm of the invention uses the collection of N labeled feature vectors to find a satisfactory solution for the inequality constrained optimization problem:

$$\min \Psi(\tau) = \|\tau\|^2/2 + C/2 \sum_{i=1}^{N} \xi_i^2, \tag{1.1}$$

$$\text{s.t. } y_i(x_i^T \tau + \tau_0) \geq 1 - \xi_i, \, i=1, \ldots, N,$$

wherein $\tau$ is a $d \times 1$ geometric locus of signed and scaled extreme points that determines the principal eigenaxis of the decision boundary of a minimum risk linear classification system, wherein $\tau$ is expressed as a dual locus of likelihood components and principal eigenaxis components, and wherein $\|\tau\|^2$ is the total allowed eigenenergy exhibited by $\tau$, $\tau_0$ is a functional of $\tau$, C and $\xi_i$ are regularization parameters, and $y_i$ are class membership statistics: if $x_i \in A$, assign $y_i=+1$, and if $x_i \in B$, assign $y_i=1$.

The objective of the machine leaning algorithm is to find the dual locus of likelihood components and principal eigenaxis components $\tau$ that minimizes the total allowed eigenenergy $\|Z|\tau\|_{min_c}^2$ and the expected risk $\Re_{min}(Z|\|\tau\|_{min_c}^2)$ exhibited by the minimum risk linear classification system $$x^T \tau + \tau_0 \underset{B}{\overset{A}{\gtrless}} 0,$$

wherein the system of N inequalities:

$$y_i(x_i^T \tau + \tau_0) \geq 1 - \xi_i, \, i=1, \ldots, N,$$

is satisfied in a suitable manner, and wherein the dual locus of $\tau$ satisfies a critical minimum eigenenergy constraint:

$$\gamma(\tau) = \|\tau\|_{min_c}^2,$$

wherein the total allowed eigenenergy $\|Z|\tau\|_{min_c}^2$ exhibited by the dual locus of $\tau$ determines the minimum expected risk $\Re_{min}(Z|\|\tau\|_{min_c}^2) = \|Z|\tau\|_{min_c}$ and the conditional probability $P(Z|\tau) = \|Z|\tau\|_{min_c}^2$ exhibited by the minimum risk linear classification system that classifies the collection of N feature vectors into the two classes A and B.

A satisfactory solution for the primal optimization problem in Eq. (1.1) is found by using Lagrange multipliers $\psi_i \geq 0$ and the Lagrangian function:

$$L_{\Psi(\tau)}(\tau,\tau_0,\xi,\psi) = \|\tau\|^2/2 + C/2\sum_{i=1}^{N}\xi_i^2 - \sum_{i=1}^{N}\psi_i\{y_i(x_i^T\tau + \tau_0) - 1 + \xi_i\}, \tag{1.2}$$

wherein the objective function and its constraints are combined with each other, that is minimized with respect to the primal variables $\tau$ and $\tau_0$, and is maximized with respect to the dual variables $\psi_i$. The Lagrange multipliers method introduces a Wolfe dual geometric locus $\psi$ that is symmetrically and equivalently related to the primal geometric locus $\tau$ and finds extrema for the restriction of the primal geometric locus $\tau$ to a Wolfe dual principal eigenspace.

The fundamental unknowns associated with the primal optimization problem in Eq. (1.1) are the scale factors $\psi_i$ of the principal eigenaxis components $$\left\{\psi_i \frac{k_{x_i}}{\|k_{x_i}\|}\right\}_{i=1}^{N}$$

on the geometric locus of a principal eigenaxis $\psi$. Each scale factor $\psi_i$ determines a conditional density and a corresponding conditional likelihood for an extreme point on a dual locus of likelihood components, and each scale factor $\psi_i$ determines the magnitude and the critical minimum eigenenergy exhibited by a scaled extreme vector on a dual locus of principal eigenaxis components.

The Karush-Kuhn-Tucker (KKT) conditions on the Lagrangian function $L_{\Psi(\tau)}$ in Eq. (1.2)

$$\tau - \Sigma_{i=1}^{N} \psi_i y_i x_i = 0, \, i=1, \ldots, N, \tag{1.3}$$

$$\Sigma_{i=1}^{N} \psi_i y_i = 0, \, i=1, \ldots, N, \tag{1.4}$$

$$c\Sigma_{i=1}^{N} \xi_i \Sigma_{i=1}^{N} \psi_i = 0, \, i=1, \ldots, N, \tag{1.5}$$

$$\psi_i \geq 0, \, i=1, \ldots, N, \tag{1.6}$$

$$\psi_i[y_i(x_i^T \tau + \tau_0) - 1 + \xi_i] \geq 0, \, i=1, \ldots, N, \tag{1.7}$$

determine a system of fundamental locus equations of binary classification, subject to geometric and statistical conditions for a minimum risk linear classification system in statistical equilibrium, that are jointly satisfied by the geometric locus of the principal eigenaxis $\psi$ and the geometric locus of the principal eigenaxis $\tau$.

Because the primal optimization problem in Eq. (1.1) is a convex optimization problem, the inequalities in Eqs (1.6) and (1.7) must only hold for certain values of the primal and the dual variables. The KKT conditions in Eqs (1.3)-(1.7) restrict the magnitudes and the eigenenergies of the principal eigenaxis components on both w and t, wherein the expected risk $\Re_{min}(Z|\|\tau\|_{min_c}^2)$ and the total allowed eigenenergy $\|Z|\tau\|_{min_c}^2$ exhibited by a minimum risk linear classification system are jointly minimized.

Substituting the expressions for $\tau$ and $\psi$ in Eqs (1.3) and (1.4) into the Lagrangian functional $L_{\Psi(\tau)}$ of Eq. (1.2) and simplifying the resulting expression determines the Lagrangian dual problem:

$$\max \Xi(\psi) = \sum_{i=1}^{N} \psi_i - \sum_{i,j=1}^{N} \psi_i \psi_j y_i y_j \frac{k_{x_i} + \delta_{ij}/C}{2}, \tag{1.8}$$

wherein $\psi$ is subject to the constraints $\Sigma_{i=1}^{N} \psi_i y_i = 0$, and $\psi_i \geq 0$, and wherein $\delta_{ij}$ is the Kronecker $\delta$ defined as unity for $i=j$ and 0 otherwise.

Equation (1.8) is a quadratic programming problem that can be written in vector notation by letting $Q \triangleq \epsilon I + \tilde{X}\tilde{X}^T$, wherein $\tilde{X} \triangleq D_y X$, wherein $D_y$ is a N×N diagonal matrix of training labels (class membership statistics) $y_i$, and wherein the N×d matrix $\tilde{X}$ is a matrix of N labeled feature vectors:

$$\tilde{X} = (y_1 x_1, y_2 x_2, \ldots, y_N x_N)^T.$$

The matrix version of the Lagrangian dual problem, which is also known as the Wolfe dual problem:

$$\max \Xi(\psi) = 1^T \psi - \frac{\psi^T Q \psi}{2} \quad (1.9)$$

is subject to the constraints $\psi^T y = 0$ and $\psi_i \geq 0$, wherein the inequalities $\psi_i \geq 0$ only hold for certain values of $\psi_i$.

Because Eq. (1.9) is a convex programming problem, the theorem for convex duality guarantees an equivalence and a corresponding symmetry between the dual loci of $\psi$ and $\tau$. Accordingly, the geometric locus of the principal eigenaxis $\psi$ determines a dual locus of likelihood components and principal eigenaxis components, wherein the expected risk $\mathfrak{R}_{min}(Z\|\psi\|_{min_c}^2)$ exhibited by the dual locus of iv is symmetrically and equivalently related to the expected risk $\mathfrak{R}_{min}(Z\|\tau v_{min_c}^2)$, exhibited by the dual locus of $\tau$: $\mathfrak{R}_{min}(Z\|\psi\|_{min_c}^2) \equiv \mathfrak{R}_{min}(Z\|\tau\|_{min_c}^2)$, and wherein the total allowed eigenenergy $\|Z|\psi\|_{min_c}^2$ exhibited by the dual locus of $\psi$ is symmetrically and equivalently related to the total allowed eigenenergy $\|Z|\tau\|_{min_c}^2$ exhibited by the dual locus of $\tau$: $\|Z|\psi\|_{min_c}^2 \equiv \|Z|\tau\|_{min_c}^2$.

The locations and the scale factors of the principal eigenaxis components on both $\psi$ and $\tau$ are considerably affected by the rank and the eigenspectrum of the Gram matrix Q, wherein a low rank Gram matrix Q determines an unbalanced principal eigenaxis and an irregular linear partition of a decision space. The Gram matrix Q has low rank, wherein d<N for a collection of N feature vectors of dimension d. These problems are solved by the following regularization method.

The regularized form of Q, wherein $\varepsilon \ll 1$ and $Q \triangleq \varepsilon I + \tilde{X}\tilde{X}^T$, ensures that Q has full rank and a complete eigenvector set, wherein Q has a complete eigenspectrum. The regularization constant C is related to the regularization parameter $\varepsilon$ by $$\frac{1}{C}.$$

For N feature vectors of dimension d, wherein d<N, all of the regularization parameters $\{\xi_i\}_{i=1}^N$ in Eq. (1.1) and all of its derivatives are set equal to a very small value: $\xi_i = \xi \ll 1$, e.g. $\xi_i = \xi = 0.02$. The regularization constant C is set equal to $$\frac{1}{\xi}: C = \frac{1}{\xi}.$$

For N feature vectors of dimension d, wherein N<d, all of the regularization parameters $\{\xi_i\}_{i=1}^N$ in Eq. (1.1) and all of its derivatives are set equal to zero: $\xi_i = \xi = 0$. The regularization constant C is set equal to infinity: $C = \infty$.

The KKT conditions in Eqs (1.3) and (1.6) require that the geometric locus of the principal eigenaxis $\tau$ satisfy the vector expression:

$$\tau = \Sigma_{i=1}^N y_i \psi_i x_i \quad (1.10)$$

wherein $\psi_i \geq 0$ and feature vectors $x_i$ correlated with Wolfe dual principal eigenaxis components $$\psi_i \frac{x_{i*}}{\|x_{i*}\|}$$

that have non-zero magnitudes $\psi_i > 0$ are termed extreme vectors. Denote the scaled extreme vectors that belong to class A and class B by $\psi_{1i*} x_{1i*}$ and $\psi_{2i*} x_{2i*}$, respectively, wherein $\psi_{1i*}$ is the scale factor for the extreme vector $x_{1i*}$ and $\psi_{2i*}$ is the scale factor for the extreme vector $x_{2i*}$. Let there be $l_1$ scaled extreme vectors $\{\psi_{1i*} x_{1i*}\}_{i=1}^{l_1}$ that belong to class A, and let there be $l_2$ scaled extreme vectors $\{\psi_{2i*} x_{2i*}\}_{i=1}^{l_2}$ that belong to class B. Let there be $l = l_1 + l_2$ scaled extreme vectors from class A and class B.

Using Eq. (1.10), the class membership statistics and the assumptions outlined above, it follows that the geometric locus of the principal eigenaxis $\tau$ is determined by the vector difference between a pair of sides, i.e., a pair of directed line segments:

$$\tau = \sum_{i=1}^{l_1} \psi_{1i*} x_{1i*} - \sum_{i=1}^{l_2} \psi_{2i*} x_{2i*} = \tau_1 - \tau_2, \quad (1.11)$$

wherein $\tau_1$ and $\tau_2$ denote the sides of $\tau$, wherein the side of $\tau_1$ is determined by the vector expression $\tau_1 = \Sigma_{i=1}^{l_1} \psi_{1i*} x_{1i*}$, and the side of $\tau_2$ is determined by the vector expression $\tau_2 = \Sigma_{i=1}^{l_2} \psi_{2i*} x_{2i*}$, and wherein the geometric locus of the principal eigenaxis $\tau$ is determined by the vector difference of $\tau_1$ and $\tau_2$.

All of the principal eigenaxis components $\psi_{1i*} x_{1i*}$ and $\psi_{2i*} x_{2i*}$ on the dual locus of $\tau = \Sigma_{i=1}^{l_1} \psi_{1i*} x_{1i*} - \Sigma_{i=1}^{l_2} \psi_{2i*} x_{2i*}$ determine an intrinsic coordinate system of geometric loci of a linear decision boundary and corresponding decision borders. FIG. 1-FIG. 5 illustrate various geometric loci of linear decision boundaries and corresponding decision borders.

FIG. 1 illustrates a linear decision boundary and linear decision borders, wherein distributions of two collections of feature vectors have different mean vectors and similar covariance matrices, wherein the distributions are overlapping with each other.

Figure 2:
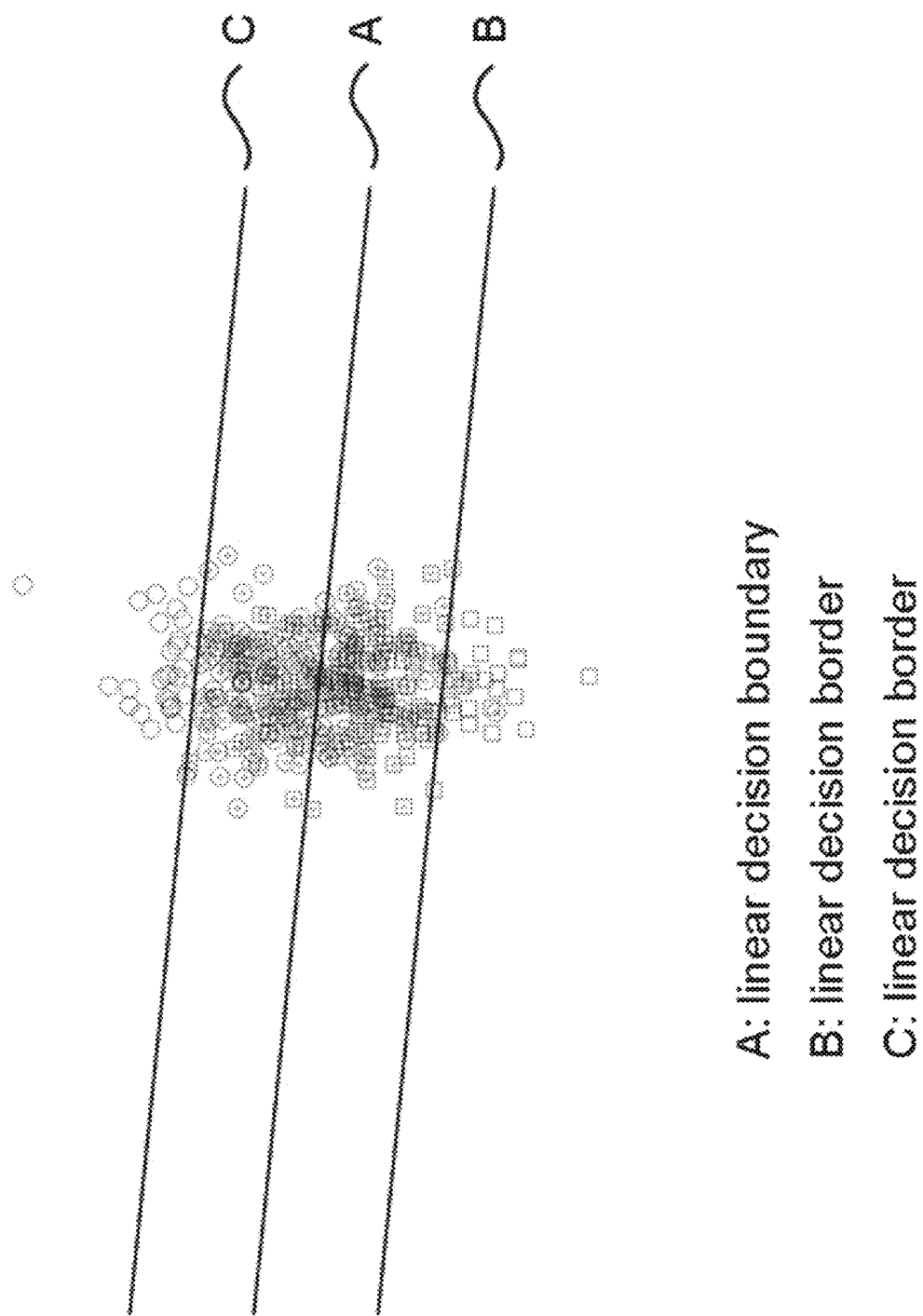
FIG. 2 illustrates symmetrical decision regions of a minimum risk linear classification system that are delineated by a linear decision boundary and linear decision borders obtained by using the method for determining a discriminant function of a minimum risk linear classification system that classifies feature vectors into two classes in which distributions of two collections of feature vectors have different mean vectors and similar covariance matrices and are overlapping with each other.

FIG. 2 illustrates a linear decision boundary and linear decision borders, wherein distributions of two collections of feature vectors have different mean vectors and similar covariance matrices, wherein the distributions are overlapping with each other.

Figure 3:
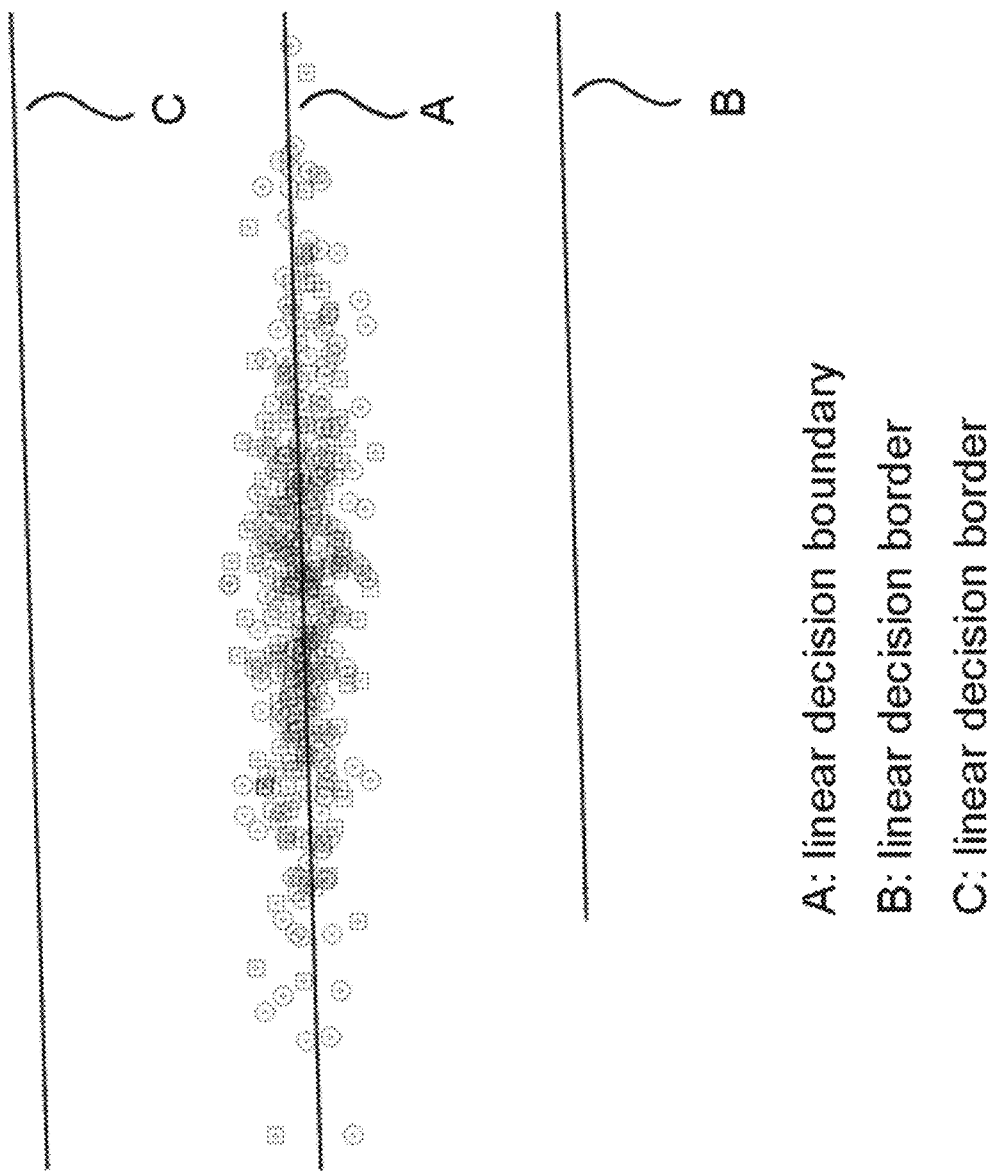
FIG. 3 illustrates symmetrical decision regions of a minimum risk linear classification system that are delineated by a linear decision boundary and linear decision borders obtained by using the method for determining a discriminant function of a minimum risk linear classification system that classifies feature vectors into two classes in which distributions of two collections of feature vectors have similar mean vectors and similar covariance matrices and are completely overlapping with each other.

FIG. 3 illustrates a linear decision boundary and linear decision borders, wherein distributions of two collections of feature vectors have similar mean vectors and similar covariance matrices, wherein the distributions are completely overlapping with each other.

Figure 4:
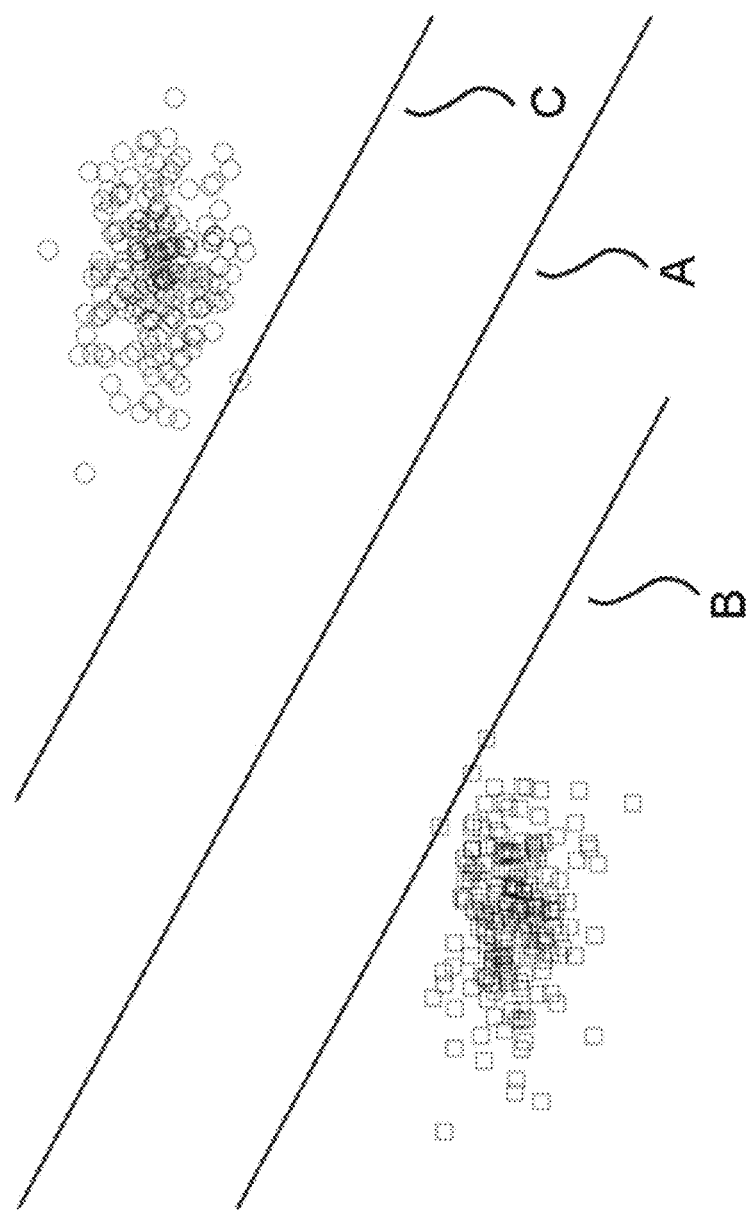
FIG. 4 illustrates symmetrical decision regions of a minimum risk linear classification system that are delineated by a linear decision boundary and linear decision borders obtained by using the method for determining a discriminant function of a minimum risk linear classification system that classifies feature vectors into two classes in which distributions of two collections of feature vectors have different mean vectors and similar covariance matrices and are not overlapping with each other.

FIG. 4 illustrates a linear decision boundary and linear decision borders, wherein distributions of two collections of feature vectors have different mean vectors and similar covariance matrices, wherein the distributions are not overlapping with each other.

Figure 5:
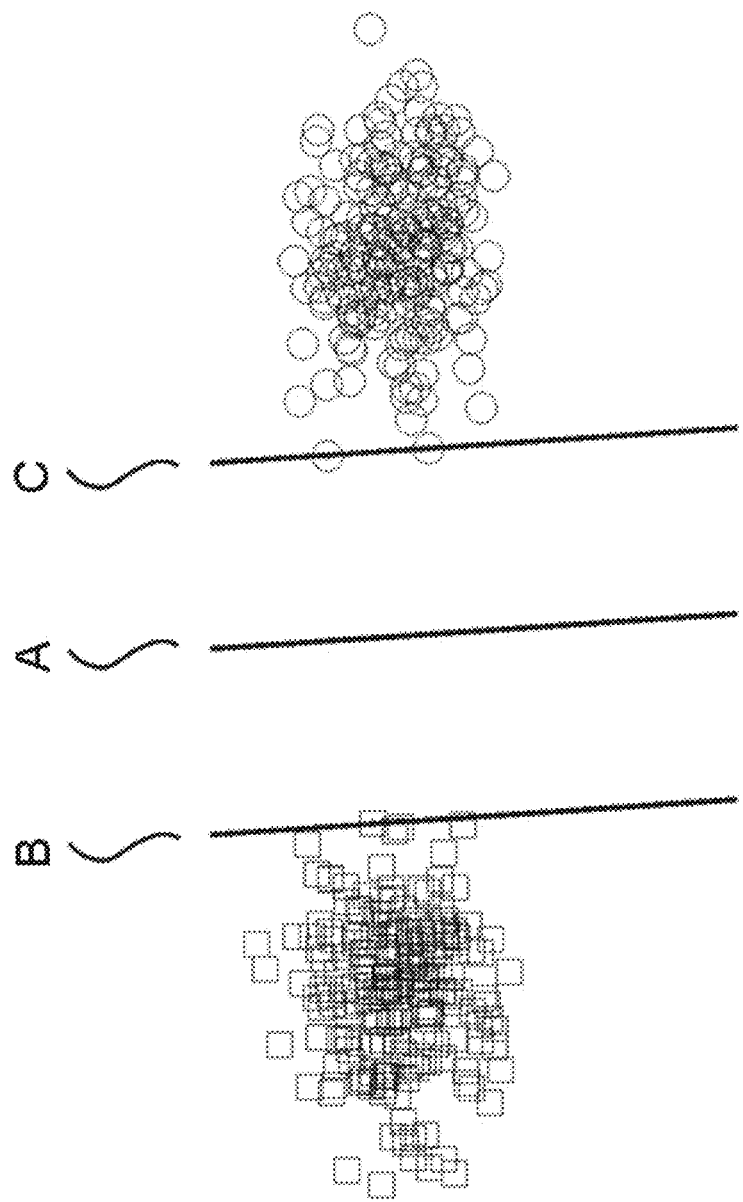
FIG. 5 illustrates symmetrical decision regions of a minimum risk linear classification system that are delineated by a linear decision boundary and linear decision borders obtained by using the method for determining a discriminant function of a minimum risk linear classification system that classifies feature vectors into two classes in which distributions of two collections of feature vectors have different mean vectors and similar covariance matrices and are not overlapping with each other.

FIG. 5 illustrates a linear decision boundary and linear decision borders, wherein distributions of two collections of feature vectors have different mean vectors and similar covariance matrices, wherein the distributions are not overlapping with each other.

The manner in which a discriminate function of the invention partitions the feature space $Z = Z_1 + Z_2$ of a minimum risk linear classification system for a collection of N feature vectors is determined by the KKT condition in Eq. (1.7) and the KKT condition of complementary slackness.

The KKT condition in Eq. (1.7) and the KKT condition of complementary slackness determine a discriminant function $$D(s) = s^T \tau + \tau_0 \quad (1.12)$$

that satisfies the set of constraints:

$$D(s)=0, D(s)=+1, \text{ and } D(s)=-1,$$

wherein $D(s)=0$ denotes a linear decision boundary that partitions the $Z_1$ and $Z_2$ decision regions of a minimum risk linear classification system $$s^T \tau + \tau_0 \underset{B}{\overset{A}{\gtreqless}} 0,$$

and wherein $D(s)=+1$ denotes the linear decision border for the $Z_1$ decision region, and wherein $D(s)=-1$ denotes the linear decision border for the $Z_2$ decision region.

The KKT condition in Eq. (1.7) and the KKT condition of complementary slackness also determines the following system of locus equations that are satisfied by $\tau_0$ and $\tau$:

$$y_i(x_{i*}^T \tau - \tau_0) - 1 + \xi_i = 0, \, i=1, \ldots, l,$$

wherein $\tau_0$ satisfies the functional of $\tau$ in the following manner:

$$\tau_0 = \frac{1}{l}\sum_{i=1}^{l} y_i(1-\xi_i) - \left(\frac{1}{l}\sum_{i=1}^{l} x_{i*}^T\right)\tau. \quad (1.13)$$

Using Eqs (1.12) and (1.13), the discriminant function is rewritten as:

$$D(s) = s^T \tau - \left(\frac{1}{l}\sum_{i=1}^{l} x_{i*}^T\right)\tau + \frac{1}{l}\sum_{i=1}^{l} y_i(1-\xi_i). \quad (1.14)$$

Using Eq. (1.14) and letting $D(s)=0$, the discriminant function is rewritten as $$s^T \tau - \left(\frac{1}{l}\sum_{i=1}^{l} x_{i*}^T\right)\tau + \frac{1}{l}\sum_{i=1}^{l} y_i(1-\xi_i) = 0, \quad (1.15)$$

wherein the constrained discriminant function $D(s)=0$ determines a linear decision boundary, and all of the points s on the linear decision boundary $D(s)=0$ exclusively reference the principal eigenaxis of $\tau$.

Using Eq. (1.14) and letting $D(s)=+1$, the discriminant function is rewritten as $$s^T \tau - \left(\frac{1}{l}\sum_{i=1}^{l} x_{i*}^T\right)\tau + \frac{1}{l}\sum_{i=1}^{l} y_i(1-\xi_i) = +1, \quad (1.16)$$

wherein the constrained discriminant function $D(s)=+1$ determines a linear decision border, and all of the points s on the linear decision border $D(s)=+1$ exclusively reference the principal eigenaxis of $\tau$.

Using Eq. (1.14) and letting $D(s)=-1$, the discriminant function is rewritten as $$s^T \tau - \left(\frac{1}{l}\sum_{i=1}^{l} x_{i*}^T\right)\tau + \frac{1}{l}\sum_{i=1}^{l} y_i(1-\xi_i) = -1, \quad (1.17)$$

wherein the constrained discriminant function $D(s)=-1$ determines a linear decision border, and all of the points s on the linear decision border $D(s)=-1$ exclusively reference the principal eigenaxis of $\tau$.

Given Eqs (1.15)-(1.17), it follows that a constrained discriminant function of the invention $$D(s) = s^T \tau - \left(\frac{1}{l}\sum_{i=1}^{l} x_{i*}^T\right)\tau + \frac{1}{l}\sum_{i=1}^{l} y_i(1-\xi_i): \, D(s)=0, D(s)=+1,$$

and $D(s) = -1$, determines geometric loci of a linear decision boundary $D(s)=0$ and corresponding decision borders $D(s)=+1$ and $D(s)=-1$ that jointly partition the decision space Z of a minimum risk linear classification system $$s^T \tau + \tau_0 \underset{B}{\overset{A}{\gtreqless}} 0$$

into symmetrical decision regions $Z_1$ and $Z_2$:$Z=Z_1+Z_2$: $Z_1 \approx Z_2$—wherein balanced portions of the extreme points $x_{1i*}$ and $x_{2i*}$ from class A and class B account for right and wrong decisions of the minimum risk linear classification system.

Therefore, the geometric locus of the principal eigenaxis $\tau$ determines an eigenaxis of symmetry $$\left(s - \frac{1}{l}\sum_{i=1}^{l} x_{i*}\right)^T (\tau_1 - \tau_2)$$

for the decision space of a minimum risk linear classification system, wherein a constrained discriminant function delineates symmetrical decision regions $Z_1$ and $Z_2$:$Z_1=Z_2$ for the minimum risk linear classification system $$s^T \tau + \tau_0 \underset{B}{\overset{A}{\gtreqless}} 0,$$

wherein the decision regions $Z_1$ and $Z_2$ are symmetrically partitioned by the linear decision boundary of Eq. (1.15), and wherein the span of the decision regions is regulated by the constraints on the corresponding decision borders of Eqs (1.16)-(1.17).

FIG. 1-FIG. 5 illustrate various types of symmetrical decision regions for minimum risk linear classification systems.

Substitution of the vector expressions for $\tau$ and $\tau_0$ in Eqs (1.11) and (1.13) into the expression for the discriminant function in Eq. (1.12) determines an expression for a discriminant function of a minimum risk linear classification system that classifies feature vectors s into two classes A and B:

$$D(s) = \left(s - \frac{1}{l}\sum_{i=1}^{l} x_{i*}\right)^T \tau_1 - \left(s - \frac{1}{l}\sum_{i=1}^{l} x_{i*}\right)^T \tau_2 + \frac{1}{l}\sum_{i=1}^{l} y_i(1 - \xi_i), \quad (1.18)$$

wherein feature vectors s belong to and are related to a collection of N feature vectors $\{x_i\}_{i=1}^{N}$, and wherein the average extreme vector $$\frac{1}{l}\sum_{i=1}^{l} x_{i*}$$

determines the average locus of the l extreme vectors $\{x_{i*}\}_{i=1}^{l}$ that belong to the collection of N feature vectors $\{x_i\}_{i=1}^{N}$, and wherein the average sign $$\frac{1}{l}\sum_{i=1}^{l} y_i(1 - \xi_i)$$

accounts for class memberships of the principal eigenaxis components on $\tau_1$ and $\tau_2$. The average locus $$\frac{1}{l}\sum_{i=1}^{l} x_{i*}$$

determines the average risk $\widehat{\mathfrak{R}}$ for the decision space $Z = Z_1 + Z_2$ of the minimum risk linear classification system $$s^T \tau + \tau_0 \underset{B}{\overset{A}{\gtrless}} 0,$$

wherein the vector transform $$x - \frac{1}{l}\sum_{i=1}^{l} x_{i*}$$

determines the distance between a feature vector s and the locus of average risk $\widehat{\mathfrak{R}}$.

Let s denote an unknown feature vector related to a collection of N feature vectors $\{x_i\}_{i=1}^{N}$ that are inputs to one of the machine learning algorithms of the invention, wherein each feature vector $x_i$ has a label $y_i$ wherein $y_i = +1$ if $x_i \in A$ and $y_i = -1$ if $x_i \in B$, and wherein a discriminant function of a minimum risk linear classification system has been determined. Now take any given unknown feature vector s.

The discriminant function $$D(s) = \left(s - \frac{1}{l}\sum_{i=1}^{l} x_{i*}\right)^T \tau_1 - \left(s - \frac{1}{l}\sum_{i=1}^{l} x_{i*}\right)^T \tau_2 + \frac{1}{l}\sum_{i=1}^{l} y_i(1 - \xi_i)$$

of Eq. (1.18) determines the likely location of the unknown feature vector s, wherein the likely location of s is determined by the vector projection of $$s - \frac{1}{l}\sum_{i=1}^{l} x_{i*}$$

onto the dual locus of likelihood components and principal eigenaxis components $\tau_1 - \tau_2$:

$$\|\tau_1 - \tau_2\| \left\| s - \frac{1}{l}\sum_{i=1}^{l} x_{i*} \right\| \cos\theta,$$

wherein the component of $$s - \frac{1}{l}\sum_{i=1}^{l} x_{i*}$$

along the dual locus of $\tau_1 - \tau_2$:

$$comp_{\overrightarrow{\tau_1 - \tau_2}}\left(s - \frac{1}{l}\sum_{i=1}^{l} x_{i*}\right) = \left\| s - \frac{1}{l}\sum_{i=1}^{l} x_{i*} \right\| \cos\theta$$

determines the signed magnitude $$\left\| s - \frac{1}{l}\sum_{i=1}^{l} x_{i*} \right\| \cos\theta$$

along the axis of $\tau_1 - \tau_2$, wherein $\theta$ is the angle between the transformed unknown feature vector $$s - \frac{1}{l}\sum_{i=1}^{l} x_{i*}$$

and $\tau_1 - \tau_2$, and wherein the decision region that the unknown feature vector s is located within is determined by the sign of the expression:

$$\text{sign}\left(\|\tau_1 - \tau_2\| \left\| s - \frac{1}{l}\sum_{i=1}^{l} x_{i*} \right\| \cos\theta + \frac{1}{l}\sum_{i=1}^{l} y_i(1 - \xi_i)\right).$$

Therefore, the likely location of the unknown feature vector s is determined by the scalar value of $$\|\tau_1 - \tau_2\| \left\| s - \frac{1}{l}\sum_{i=1}^{l} x_{i*} \right\| \cos\theta,$$

along the axis of the dual locus $\tau_1 - \tau_2$, wherein the scalar value of the expression $$\|\tau_1 - \tau_2\| \left( \left\| s - \frac{1}{l}\sum_{i=1}^{l} x_{i*} \right\| \cos\theta \right) + \frac{1}{l}\sum_{i=1}^{l} y_i(1-\xi_i)$$

indicates the decision region $Z_1$ or $Z_2$ that the unknown feature vector s is located within along with the corresponding class of s.

Thus, if:

$$\|\tau_1 - \tau_2\| \left( \left\| s - \frac{1}{l}\sum_{i=1}^{l} x_{i*} \right\| \cos\theta \right) + \frac{1}{l}\sum_{i=1}^{l} y_i(1-\xi_i) \geq 0,$$

then the unknown feature vector s is located within region $Z_1$ and s∈A, whereas if $$\|\tau_1 - \tau_2\| \left( \left\| s - \frac{1}{l}\sum_{i=1}^{l} x_{i*} \right\| \cos\theta \right) + \frac{1}{l}\sum_{i=1}^{l} y_i(1-\xi_i) < 0,$$

then the unknown feature vectors s is located within region $Z_2$ and s∈B.

The minimum risk linear classification system of the invention decides which of the two classes A or B that the unknown feature vector s belongs to according to the sign of +1 or −1 that is output by the signum function:

$$\text{sign}(D(s)) \overset{\Delta}{=} \text{sign}\left( \|\tau_1 - \tau_2\| \left( \left\| s - \frac{1}{l}\sum_{i=1}^{l} x_{i*} \right\| \cos\theta \right) + \frac{1}{l}\sum_{i=1}^{l} y_i(1-\xi_i) \right) \quad (1.19)$$

and thereby classifies the unknown feature vector s.

Thus, the discriminant function of the invention in Eq. (1.18) determines likely locations of each one of the feature vectors $x_i$ that belong to a collection of N feature vectors $\{x_i\}_{i=1}^N$ and any given unknown feature vectors s related to the collection, wherein the feature vectors are inputs to one of the machine learning algorithms of the invention and a discriminant function of a minimum risk linear classification system has been determined.

Further, the discriminant function identifies the decision regions $Z_1$ and $Z_2$ related to the two classes A and B that each one of the N feature vectors $x_i$ and the unknown feature vectors s are located within, wherein the discriminant function recognizes the classes of each one of the N feature vectors $x_i$ and each one of the unknown feature vectors s, and the minimum risk linear classification system of the invention in Eq. (1.19) decides which of the two classes that each one of the N feature vectors $x_i$ and each one of the unknown feature vectors s belong to and thereby classifies the collection of N feature vectors $\{x_i\}_{i=1}^N$ and any given unknown feature vectors s.

Therefore, discriminant functions of the invention exhibit a novel and useful property, wherein, for any given collection of feature vectors that belong to two classes and are inputs to a machine learning algorithm of the invention, the discriminant function that is determined by the machine learning algorithm determines likely locations of each one of the feature vectors that belong to the given collection of feature vectors and any given unknown feature vectors related to the collection, and identifies the decision regions related to the two classes that each one of the feature vectors and each one of the unknown feature vectors are located within, wherein the discriminant function recognizes the classes of the feature vectors and the unknown feature vectors according to the signs related to the two classes.

The likelihood components and the corresponding principal eigenaxis components $\psi_{1i*}x_{1i*}$ and $\psi_{2i*}x_{2i*}$, on the dual locus of $\psi_{1i*}$ and $\psi_{2i*}$ are determined by the geometric and the statistical structure of the geometric locus of signed and scaled extreme points: $\tau_1 - \tau_2 = \sum_{i=1}^{l_1} \psi_{1i*}x_{1i*} - \sum_{i=1}^{l_2} \psi_{2i*}x_{2i*}$, wherein the scale factors $\psi_{1i*}$ and $\psi_{2i*}$ of the geometric locus determine magnitudes $\|\psi_{1i*}x_{1i*}\|$ and $\|\psi_{2i*}x_{2i*}\|$ as well as critical minimum eigenenergies $\|\psi_{1i*}x_{1i*}\|_{min_c}^2$ and $\|\psi_{2i*}x_{2i*}\|_{min_c}^2$, exhibited by respective principal eigenaxis components $\psi_{1i*}x_{1i*}$ and $\psi_{2i*}x_{2i*}$ on the dual locus of $\tau_1 - \tau_2$, and each scale factor $\psi_{1i*}$ or $\psi_{2i*}$ determines a conditional density and a corresponding conditional likelihood for a respective extreme point $x_{1i*}$ or $x_{2i*}$.

Scale factors are determined by finding a satisfactory solution for the Lagrangian dual optimization problem in Eq. (1.9), wherein finding a geometric locus of signed and scaled extreme points involves optimizing a vector-valued cost function with respect to constraints on the scaled extreme vectors on the dual loci of $\psi$ and $\tau$, wherein the constraints are specified by the KKT conditions in Eqs (1.3)-(1.7).

The Wolfe dual geometric locus of scaled extreme points on $\psi$ is determined by the largest eigenvector $\psi_{max}$ of the Gram matrix Q associated with the quadratic form $\psi_{max}^T Q \psi_{max}$ in Eq. (1.9), wherein $\psi^T y = 0$, $\psi_{i*} > 0$, and wherein $\psi_{max}$ is the principal eigenaxis of an implicit linear decision boundary—associated with the constrained quadratic form $\omega_{max}^T Q \psi_{max}$—within the Wolfe dual principal eigenspace of $\psi$, wherein the inner product statistics contained within the Gram matrix Q determine an intrinsic coordinate system of the intrinsic linear decision boundary of Eq. (1.9).

The theorem for convex duality indicates that the principal eigenaxis of $\psi$ satisfies a critical minimum eigenenergy constraint that is symmetrically and equivalently related to the critical minimum eigenenergy constraint on the principal eigenaxis of $\tau$, within the Wolfe dual principal eigenspace of $\psi$ and $\tau$: $\|Z|\psi\|_{min_c}^2 \approx \|Z|\tau\|_{min_c}^2$, wherein the principal eigenaxis of $\psi$ satisfies a critical minimum eigenenergy constraint:

$$\max \psi_{max}^T Q \psi_{max} = \lambda_{max_\psi} \|Z|\psi_{max}\|_{min_c}^2,$$

and the functional $1^T \psi - \psi^T Q \psi / 2$ in Eq. (1.9) is maximized by the largest eigenvector $\psi_{max}$ of Q, wherein the constrained quadratic form $\psi^T Q \psi / 2$, wherein $\psi_{max}^T y = 0$ and $\psi_{i*} > 0$, reaches its smallest possible value. It follows that the principal eigenaxis components on $\psi$ satisfy minimum length constraints.

The principal eigenaxis components on $\psi$ also satisfy an equilibrium constraint. The KKT condition in Eq. (1.4) requires that the magnitudes of the principal eigenaxis components on the dual locus of $\psi$ satisfy the locus equation:

$$(y_i=1)\sum_{i=1}^{l_1}\psi_{1i*} + (y_i=-1)\sum_{i=1}^{l_2}\psi_{2i*} = 0 \quad (1.20)$$

wherein Eq. (1.20) determines the Wolf dual equilibrium point:

$$\sum_{i=1}^{l_1}\psi_{1i*} - \sum_{i=1}^{l_2}\psi_{2i*} = 0 \quad (1.21)$$

of a minimum risk linear classification system, wherein the critical minimum eigenenergies exhibited by the principal eigenaxis of $\psi$ are symmetrically concentrated.

Given Eq. (1.21), it follows that the integrated lengths of the Wolfe dual principal eigenaxis components correlated with each class balance each other, wherein the principal eigenaxis of $\psi$ is in statistical equilibrium:

$$\sum_{i=1}^{l_1} \psi_{1i*} = \sum_{i=1}^{l_2} \psi_{2i*} \qquad (1.22)$$

Now, each scale factor $\psi_{1i*}$ or $\psi_{2i*}$ is correlated with a respective extreme vector $x_{1i*}$ or $x_{2i*}$. Therefore, let $l_1+l_2=l$, and express the principal eigenaxis of $\psi$ in terms of $l$ scaled, unit extreme vectors:

$$\psi = \sum_{i=1}^{l_1} \psi_{1i*} \frac{x_{1i*}}{\|x_{1i*}\|} + \sum_{i=1}^{l_2} \psi_{2i*} \frac{x_{2i*}}{\|x_{2i*}\|} = \psi_1 + \psi_2, \qquad (1.23)$$

wherein $\psi_1$ and $\psi_2$ denote the sides of the dual locus of $\psi$, wherein the side of $\psi_1$ is determined by the vector expression $$\psi_1 = \sum_{i=1}^{l_1} \psi_{1i*} \frac{x_{1i*}}{\|x_{1i*}\|},$$

and wherein the side of $\psi_2$ is determined by the vector expression $$\psi_2 = \sum_{i=1}^{l_2} \psi_{2i*} \frac{x_{2i*}}{\|x_{2i*}\|}.$$

The system of locus equations in Eqs (1.20)-(1.23) demonstrates that the principal eigenaxis of $\psi$ is determined by a geometric locus of scaled, unit extreme vectors from class A and class B, wherein all of the scaled, unit extreme vectors on $\psi_1$ and $\psi_2$ are symmetrically distributed over either side of the geometric locus of the principal eigenaxis $\psi$, wherein a statistical fulcrum is placed directly under the center of the principal eigenaxis of $\psi$.

Using Eq. (1.22) and Eq. (1.23), it follows that the length $\|\psi_1\|$ of $\psi_1$ is equal to the length $\|\psi_2\|$ of $\psi_2$: $\|\psi_1\| = \|\psi_2\|$. It also follows that the total allowed eigenenergies $\|Z|\psi_1\|_{min_c}^2$ and $\|Z|\psi_2\|_{min_c}^2$ exhibited by $\psi_1$ and $\psi_2$ are symmetrically balanced with each other about the geometric center of the principal eigenaxis of $\psi$: $\|Z|\psi_1\|_{min_c}^2 = \|Z|\psi_2\|_{min_c}^2$.

The equilibrium constraint on the geometric locus of the principal eigenaxis $\psi$ in Eq. (1.20) ensures that the critical minimum eigenenergies exhibited by all of the principal eigenaxis components on $\psi_1$ and $\psi_2$ are symmetrically concentrated within the principal eigenaxis of $\psi$:

$$\left\| \sum_{i=1}^{l_1} \psi_{1i*} \frac{x_{1i*}}{\|x_{1i*}\|} \right\|_{min_c}^2 = \left\| \sum_{i=1}^{l_2} \psi_{2i*} \frac{x_{2i*}}{\|x_{2i*}\|} \right\|_{min_c}^2. \qquad (1.24)$$

Using Eq. (1.24), it follows that the principal eigenaxis of $\psi$ satisfies a state of statistical equilibrium, wherein all of the principal eigenaxis components on $\psi$ are equal or in correct proportions, relative to the center of $\psi$, wherein components of likelihood components and corresponding principal eigenaxis components of class A—along the axis of $\psi_1$—are symmetrically balanced with components of likelihood components and corresponding principal eigenaxis components of class B—along the axis of $\psi_2$.

Therefore, the principal eigenaxis of $\psi$ determines a point at which the critical minimum eigenenergies exhibited by all of the scaled, unit extreme vectors from class A and class B are symmetrically concentrated, wherein the total allowed eigenenergy $\|Z|\psi\|_{min_c}^2$ exhibited by the principal eigenaxis of $\psi$ is minimized within the Wolfe dual principal eigenspace.

The scale factors are associated with the fundamental unknowns of the constrained optimization problem in Eq. (1.1). Now, the geometric locus of the principal eigenaxis $\psi$ can be written as $$\Psi_{max} = \frac{\psi_1}{\lambda_{max_\psi}} \begin{pmatrix} \|x_1\|\|x_1\|\cos\theta_{x_1 x_1} \\ \|x_2\|\|x_1\|\cos\theta_{x_2 x_1} \\ \vdots \\ -\|x_N\|\|x_1\|\cos\theta_{x_N x_1} \end{pmatrix} + \qquad (1.25)$$

$$\ldots + \ldots \frac{\psi_N}{\lambda_{max_\psi}} \begin{pmatrix} -\|x_1\|\|x_N\|\cos\theta_{x_1 x_N} \\ -\|x_2\|\|x_N\|\cos\theta_{x_2 x_N} \\ \vdots \\ \|x_N\|\|x_N\|\cos\theta_{x_N x_N} \end{pmatrix},$$

wherein each scale factor $\psi_j$ is correlated with scalar projections $\|x_j\|\cos\theta_{x_i x_j}$ of a feature vector $x_j$ onto a collection of N signed feature vectors $x_i$.

Further, given a Gram matrix of all possible inner products of a collection of N feature vectors $\{x_i\}_{i=1}^N$, the pointwise covariance statistic $\widehat{cov}_{up}(x_i)$ of any given feature vector $x_i$ $$\widehat{cov}_{up}(x_i) = \|x_i\| \Sigma_{j=1}^N \|x_j\| \cos\theta_{x_i x_j} \qquad (1.26)$$

determines a unidirectional estimate of the joint variations between the random variables of each feature vector $x_j$ in the collection of N feature vectors $\{x_i\}_{i=1}^N$ and the random variables of the feature vector $x_i$, along with a unidirectional estimate of the joint variations between the random variables of the mean feature vector $\Sigma_{j=1}^N x_j$ and the feature vector $x_i$, along the axis of the feature vector $x_i$.

Let $i=1:l_1$, where each extreme vector $x_{1i*}$ is correlated with a principal eigenaxis component $$\psi_{1i*} \frac{x_{1i*}}{\|x_{1i*}\|}$$

on $\psi_1$. Now take the extreme vector $x_{1i*}$ that is correlated with the principal eigenaxis component $$\psi_{1i*} \frac{x_{1i*}}{\|x_{1i*}\|}.$$

Using Eqs (1.25) and (1.26), it follows that the geometric locus of the principal eigenaxis component $$\psi_{1i*} \frac{x_{1i*}}{\|x_{1i*}\|}$$

on $\psi_1$ is determined by the locus equation:

$$\psi_{1i*} = \lambda_{max_\psi}^{-1} \|x_{1i*}\| \Sigma_{j=1}^{l_1} \psi_{1j*} \|x_{1j*}\| \cos\theta_{x_{1i*} x_{1j*}} - \lambda_{max_\psi}^{-1} \|x_{1i*}\| \Sigma_{j=1}^{l_2} \psi_{2j*} \|x_{2j*}\| \cos\theta_{x_{1i*} x_{2j*}}, \qquad (1.27)$$

wherein components of likelihood components and principal eigenaxis components for class A—along the axis of the extreme vector $x_{1i*}$—are symmetrically balanced with opposing components of likelihood components and principal eigenaxis components for class B—along the axis of the extreme vector $x_{1i*}$:

$$\psi_{1i*} = \lambda_{max_\psi}^{-1}\|x_{1i*}\|\sum_{j=1}^{l_1} comp_{\overrightarrow{x_{1i*}}}(\overrightarrow{\psi_{1j*}x_{1j*}}) - \lambda_{max_\psi}^{-1}\|x_{1i*}\|\sum_{j=1}^{l_2} comp_{\overrightarrow{x_{1i*}}}(\overrightarrow{\psi_{2j*}x_{2j*}}),$$

wherein $\psi_{1i*}$ determines a scale factor for the extreme vector $$\frac{x_{1i*}}{\|x_{1i*}\|}.$$

Accordingly, Eq. (1.27) determines a scale factor $\omega_{1i*}$ for a correlated extreme vector $x_{1i*}$.

Let $i=1:l_2$, where each extreme vector $x_{2i*}$ is correlated with a principal eigenaxis component $$\psi_{2i*}\frac{x_{2i*}}{\|x_{2i*}\|}$$

on $\psi_2$. Now take the extreme vector $x_{2i*}$ that is correlated with the principal eigenaxis component $$\psi_{2i*}\frac{x_{2i*}}{\|x_{2i*}\|}.$$

Using Eqs (1.25) and (1.26), it follows that the geometric locus of the principal eigenaxis component $$\psi_{2i*}\frac{x_{2i*}}{\|x_{2i*}\|}$$

on $\psi_2$ is determined by the locus equation:

$$\psi_{2i*} = \lambda_{max_\psi}^{-1}\|x_{2i*}\|\Sigma_{j=1}^{l_2}\psi_{2j*}\|x_{2j*}\|_{2j*}\|\cos\theta_{x_{2j*}x_{2j*}} - \lambda_{max_\psi}^{-1}\|x_{2i*}\|\Sigma_{j=1}^{l_1}\psi_{1j*}\|x_{1j*}\|\cos\theta_{x_{2j*}x_{1j*}}$$

(1.28)

wherein components of likelihood components and principal eigenaxis components for class B—along the axis of the extreme vector $x_{2i*}$—are symmetrically balanced with opposing components of likelihood components and principal eigenaxis components for class A—along the axis of the extreme vector $x_2$:

$$\psi_{2i*} = \lambda_{max_\psi}^{-1}\|x_{2i*}\|\sum_{j=1}^{l_1} comp_{\overrightarrow{x_{2i*}}}(\overrightarrow{\psi_{2j*}x_{2j*}}) - \lambda_{max_\psi}^{-1}\|x_{2i*}\|\sum_{j=1}^{l_2} comp_{\overrightarrow{x_{2i*}}}(\overrightarrow{\psi_{1j*}x_{1j*}}),$$

wherein $\psi_{2i*}$ determines a scale factor for the extreme vector $$\frac{x_{2i*}}{\|x_{2i*}\|}.$$

Accordingly, Eq. (1.28) determines a scale factor $\psi_2$, for a correlated extreme vector $x_{2*}$.

Given the pointwise covariance statistic in Eq. (1.26), it follows that Eq. (1.27) and Eq. (1.28) determine the manner in which the vector components of a set of 1 scaled extreme vectors $\{\psi_{j*}x_{j*}\}_{j=1}^l$, wherein the set belongs to a collection of N feature vectors $\{x_i\}_{i=1}^N$, are distributed along the axes of respective extreme vectors $x_{1i*}$ or $x_{2i*}$, wherein the vector components of each scaled extreme vector $\psi_{j*}x_{j*}$ are symmetrically distributed according to: (1) a class label +1 or −1; (2) a signed magnitude $\|x_{j*}\|\cos\theta_{x_{1j*}x_{j*}}$ or $\|x_{j*}\|\cos\theta_{x_{2j*}x_{j*}}$; and (3) a symmetrically balanced distribution of 1 scaled extreme vectors $\{\psi_{k*}x_{k*}\}_{k=1}^l$ along the axis of the scaled extreme vector $x_{j*}$, wherein the symmetrically balanced distribution is specified by the scale factor $\psi_{j*}$. Accordingly, the geometric locus of each principal eigenaxis component $$\psi_{1i*}\frac{x_{1i*}}{\|x_{1i*}\|} \text{ or } \psi_{2i*}\frac{x_{2i*}}{\|x_{2i*}\|}$$

on the geometric locus of the principal eigenaxis $\psi$ determines the manner in which the components of an extreme vector $x_{1i*}$ or $x_{2i*}$ are symmetrically distributed over the axes of a set of 1 signed and scaled extreme vectors: $\{\psi_{j*}k_{x_{j*}}\}_{j=1}^l$.

It follows that the geometric locus of each principal eigenaxis component $$\psi_{1i*}\frac{x_{1i*}}{\|x_{1i*}\|} \text{ or } \psi_{2i*}\frac{x_{2i*}}{\|x_{2i*}\|}$$

on the geometric locus of the principal eigenaxis $\psi$ determines a conditional distribution of coordinates for a correlated extreme point $x_{1i*}$ or $x_{2i*}$, wherein $$\psi_{1i*}\frac{x_{1i*}}{\|x_{1i*}\|}$$

determines a pointwise conditional density estimate $p(x_{1i*}|comp_{\overrightarrow{\tau}}(\overrightarrow{x_{1i*}}))$ for the correlated extreme point $x_{1i*}$, wherein the component of the extreme vector $x_{1i*}$ is symmetrically distributed over the geometric locus of the principal eigenaxis $\kappa$:

$$p(x_{1i*} \mid comp_{\overrightarrow{\tau}}(\overrightarrow{x_{1i*}})) = \lambda_{max_\psi}^{-1}\sum_{j=1}^{l_1}\|\psi_{1j*}x_{1j*}\|comp_{\overrightarrow{\psi_{1j*}x_{1j*}}}(\overrightarrow{x_{1i*}}) - \lambda_{max_\psi}^{-1}\sum_{j=1}^{l_2}\|\psi_{2j*}x_{2j*}\|comp_{\overrightarrow{\psi_{2j*}x_{2j*}}}(\overrightarrow{x_{1i*}}),$$

and wherein $$\psi_{2i*}\frac{x_{2i*}}{\|x_{2i*}\|}$$

determines a pointwise conditional density estimate $p(x_{2i*}|comp_{\overrightarrow{-\tau}(\overrightarrow{x_{2i*}})})$ for the correlated extreme point $x_{2i*}$, wherein the component of the extreme vector $k_{x_{2i*}}$ is symmetrically distributed over the axis of the geometric locus of $-\tau$:

$$p(x_{2i*} \mid comp_{-\tau}(\overrightarrow{x_{2i*}})) = \lambda_{max_{\psi}}^{-1} \sum_{j=1}^{l_2} \|\psi_{2j*} x_{2j*}\| comp_{\overrightarrow{\psi_{2j*} x_{2j*}}}(\overrightarrow{x_{2i*}}) -$$

$$\lambda_{max_{\psi}}^{-1} \sum_{j=1}^{l_1} \|\|\psi_{1j*} x_{1j*}\|\| comp_{\overrightarrow{\|\psi_{1j*} x_{1j*}\|}}(\overrightarrow{x_{2i*}}).$$

Thus, each scale factor $\psi_{1i*}$ or $\psi_{2i*}$ determines a conditional density and a corresponding conditional likelihood for a correlated extreme point $x_{1i*}$ or $x_{2i*}$.

Therefore, conditional densities and corresponding conditional likelihoods $\psi_{1i*} x_{2i*}$ for the $x_{1i*}$ extreme points are identically distributed over the principal eigenaxis components on $\tau_1$ $$\tau_1 = \Sigma_{i=1}^{l_1} \psi_{1i*} x_{1i*}$$

wherein $\psi_{1i*} x_{1i*}$ determines a conditional density and a corresponding conditional likelihood for a correlated extreme point $x_{1i*}$, and wherein $\tau_1$ determines a parameter vector for a class-conditional probability density function $p(x_{1i*}|\tau_1)$ for a given set $\{x_{1i*}\}_{i=1}^{l_1}$ of extreme points $x_{1i*}$ that belong to a collection of N feature vectors $\{x_i\}_{i=1}^{N}$:

$$\tau_1 = p(x_{1i*}|\tau_1),$$

wherein the area $\|\psi_{1i*} x_{1i*}\|^2$ under a scaled extreme vector $\psi_{1i*} x_{1i*}$ determines a conditional probability that an extreme point $x_{1i*}$ will be observed within a localized region of either region $Z_1$ or region $Z_2$ within a decision space Z, and wherein the area under the conditional density function $p(x_{1i*}|\tau_1)$ determines the conditional probability $P(x_{1i*}|\tau_1)$ of observing the set $\{x_{1i*}\}_{i=1}^{l_1}$ of extreme points $x_{1i*}$ within localized regions of the decision space $Z=Z_1+Z_2$ of a minimum risk linear classification system $$s^T \tau + \tau_0 \overset{A}{\underset{B}{\gtreqless}} 0.$$

Likewise, conditional densities and corresponding conditional likelihoods $\psi_{2i*} x_{2i*}$ for the $x_{2i*}$ extreme points are identically distributed over the principal eigenaxis components on $\tau_2$ $$\tau_2 = \Sigma_{i=1}^{l_2} \psi_{2i*} x_{2i*},$$

wherein $\psi_{2i*} x_{2i*}$ determines a conditional density and a corresponding conditional likelihood for a correlated extreme point $x_{2i*}$, and wherein $\tau_2$ determines a parameter vector for a class-conditional probability density function $p(x_{2i*}|\tau_2)$ for a given set $\{x_{2i*}\}_{i=1}^{l_2}$ of extreme points $x_{2i*}$ that belong to a collection of N feature vectors $\{x_i\}_{i=1}^{N}$:

$$\tau_2 = p(x_{2i*}|\tau_2),$$

wherein the area $\|\psi_{2i*} x_{2i*}\|^2$ under a scaled extreme vector $\psi_{2i*} x_{2i*}$ determines a conditional probability that an extreme point $x_{2i*}$ will be observed within a localized region of either region $Z_1$ or region $Z_2$ within a decision space Z, and wherein the area under the conditional density function $p(x_{2i*}|\tau_2)$ determines the conditional probability $P(x_{2i*}|\tau_2)$ of observing the set $\{x_{2i*}\}_{i=1}^{l_2}$ of extreme points $x_{2i*}$ within localized regions of the decision space $Z=Z_1+Z_2$ of a minimum risk linear classification system $$s^T \tau + \tau_0 \overset{A}{\underset{B}{\gtreqless}} 0.$$

The integral of a conditional density function $p(x_{1i*}|\tau_1)$ for class A $$P(x_{1i*} \mid \tau_1) = \int_Z \left( \sum_{i=1}^{l_1} \psi_{1i*} x_{1i*} \right) d\tau_1 =$$

$$\int_Z p(x_{1i*} \mid \tau_1) d\tau_1 = \int_Z \tau_1 d\tau_1 = \frac{1}{2} \|\tau_1\|^2 + C = \|\tau_1\|^2 + C_1,$$

over the decision space $Z=Z_1+Z_2$ of a minimum risk linear classification system, determines the conditional probability $P(x_{1i*}|\tau_1)$ of observing a set $\{x_{1i*}\}_{i=1}^{l_1}$ of extreme points $x_{1i*}$ within localized regions of the decision space $Z=Z_1+Z_2$, wherein integrated conditional densities $\|\psi_{1i*} x_{1i*}\|_{min_c}^2$ of extreme points $x_{1i*}$ located within the decision region $Z_1$ determine costs $C_{\overline{\Re}}(Z_1\|\psi_{1i*} x_{1i*}\|_{min_c}^2)$ for expected counter risks $\overline{\Re}_{min}(Z_1\|\psi_{1i*} x_{1i*}\|_{min_c}^2)$ of making correct decisions, and integrated conditional densities $\|\psi_{1i*} x_{1i*}\|_{min_c}^2$ of extreme points $x_{1i*}$ located within the decision region $Z_2$ determine costs $C_{\Re}(Z_2\|\psi_{1i*} x_{1i*}\|_{min_c}^2)$ for expected risks $\Re_{min}(Z_2\|\psi_{1i*} x_{1i*}\|_{min_c}^2)$ of making decision errors.

Accordingly, all of the scaled extreme vectors $\psi_{1i*} x_{1i*}$ from class A possess critical minimum eigenenergies $\|\psi_{1i*} x_{1i*}\|_{min_c}^2$ that determine either costs $C_{\Re}$ for obtaining expected risks of making decision errors or costs $C_{\overline{\Re}}$ for obtaining expected counter risks of making correct decisions.

Therefore, the conditional probability function $P(x_{1i*}|\tau_1)$ for class A is given by the integral $$P(x_{1i*}|\tau_1) = \int_Z \tau_1 d\tau_1 = \|Z|\tau_1\|_{min_c}^2 + C_1 \qquad (1.29)$$

over the decision space $Z=Z_1+Z_2$ of a minimum risk linear classification system, wherein the integral of Eq. (1.29) has a solution in terms of the critical minimum eigenenergy $\|Z|\tau_1\|_{min_c}^2$ exhibited by $\tau_1$ and an integration constant $C_1$.

The integral of a conditional density function $p(x_{2i*}|\tau_2)$ for class B $$P(x_{2i*} \mid \tau_2) = \int_Z \left( \sum_{i=1}^{l_2} \psi_{2i*} x_{2i*} \right) d\tau_2 =$$

$$\int_Z p(x_{2i*} \mid \tau_2) d\tau_2 = \int_Z \tau_2 d\tau_2 = \frac{1}{2} \|\tau_2\|^2 + C = \|\tau_2\|^2 + C_2$$

over the decision space $Z=Z_1+Z_2$ of a minimum risk linear classification system, determines the conditional probability $P(x_{2i*}|\tau_2)$ of observing a set $\{x_{2i*}\}_{i=1}^{l_2}$ of extreme points $x_{2i*}$ within localized regions of the decision space $Z=Z_1+Z_2$, wherein integrated conditional densities $\|\psi_{2i*} x_{2i*}\|_{min_c}^2$ of extreme points $x_{2i*}$ located within the decision region $Z_1$ determine costs $C_{\Re}(Z_1\|\psi_{2i*} x_{2i*}\|_{min_c}^2)$ for expected risks $\Re_{min}(Z_1\|\psi_{2i*} x_{2i*}\|_{min_c}^2)$ of making decision errors, and integrated conditional densities $\psi_{2i*} x_{2i*}\|_{min_c}^2$ of extreme points $x_{2i*}$ located within the decision region $Z_2$ determine costs $C_{\overline{\Re}}(Z_2\|\|\psi_{2i*}x_{2i*}\|_{min_c}^2)$ for expected counter risks $\overline{\Re}_{min}(Z_2\|\|\psi_{2i*}x_{2i*}\|_{min_c}^2)$ of making correct decisions.

Accordingly, all of the scaled extreme vectors $\psi_{2i*}k_{x_{2i*}}$ from class B possess critical minimum eigenenergies $\|\psi_{2i*}k_{x_{2i*}}\|_{min_c}^2$ that determine either costs $C_{\Re}$ for obtaining expected risks of making decision errors or costs $C_{\overline{\Re}}$ for obtaining expected counter risks of making correct decisions.

Therefore, the conditional probability function $P(x_{2i*}|\tau_2)$ for class B is given by the integral $$P(x_{2i*}|\tau_2) = \int_Z \tau_2 d\tau_2 = \|Z|\tau_2\|_{min_c}^2 + C_2 \quad (1.30)$$

over the decision space $Z=Z_1+Z_2$ of a minimum risk linear classification system, wherein the integral of Eq. (1.30) has a solution in terms of the critical minimum eigenenergy $\|Z|\tau_2\|_{min_c}^2$ exhibited by $\tau_2$ and an integration constant $C_2$.

Machine learning algorithms of the present invention find the right mix of principal eigenaxis components on the dual loci of $\psi$ and $\tau$ by accomplishing an elegant, statistical balancing feat within the Wolfe dual principal eigenspace of $\psi$ and $\tau$. The scale factors $\{\psi_{i*}\}_{i=1}^l$ of the principal eigenaxis components on $\psi$ play a fundamental role in the statistical balancing feat.

Using Eq. (1.27), the integrated lengths $\Sigma_{i=1}^{l_1}\psi_{1i*}$ of the principal eigenaxis components on $\psi_1$ satisfy the identity:

$$\Sigma_{i=1}^{l_1}\psi_{1i*} = \lambda_{max_\psi}^{-1}\Sigma_{i=1}^{l_1}x_{1i*}^T(\Sigma_{j=1}^{l_1}\psi_{1j*}x_{1j*} - \Sigma_{j=1}^{l_2}\psi_{2j*}x_{2j*}) \quad (1.31)$$

and, using Eq. (1.28), the integrated lengths $\Sigma_{i=1}^{l_2}\psi_{2i*}$ of the principal eigenaxis components on $\psi_2$ satisfy the identity:

$$\Sigma_{i=1}^{l_2}\psi_{2i*} = \lambda_{max_\psi}^{-1}\Sigma_{i=1}^{l_2}x_{2i*}^T(\Sigma_{j=1}^{l_2}\psi_{2j*}x_{2j*} - \Sigma_{j=1}^{l_1}\psi_{1j*}x_{1j*}) \quad (1.32)$$

Returning to Eq. (1.22), wherein the principal eigenaxis of $\psi$ is in statistical equilibrium, it follows that the RHS of Eq. (1.31) equals the RHS of Eq. (1.32):

$$\lambda_{max_\psi}^{-1}\Sigma_{i=1}^{l_1}x_{1i*}^T(\Sigma_{j=1}^{l_1}\psi_{1j*}x_{1j*} - \Sigma_{j=1}^{l_2}\psi_{2j*}x_{2j*}) =$$

$$\lambda_{max_\psi}^{-1}\Sigma_{i=1}^{l_2}x_{2i*}^T(\Sigma_{j=1}^{l_2}\psi_{2j*}x_{2j*} - \Sigma_{j=1}^{l_1}\psi_{1j*}x_{1j*}),$$

wherein components of all of the extreme vectors $x_{1i*}$ and $x_{2i*}$ from class A and class B are distributed over the axes of $\tau_1$ and $\tau_2$ in the symmetrically balanced manner:

$$\lambda_{max_\psi}^{-1}\Sigma_{i=1}^{l_1}x_{1i*}^T(\tau_1-\tau_2) = \lambda_{max_\psi}^{-1}\Sigma_{i=1}^{l_2}x_{2i*}^T(\tau_2-\tau_1), \quad (1.33)$$

wherein components of extreme vectors $x_{1i*}$ along the axis of $\tau_2$ oppose components of extreme vectors $x_{1i*}$ along the axis of $\tau_1$, and components of extreme vectors $x_{2i*}$ along the axis of $\tau_1$ oppose components of extreme vectors $x_{2i*}$ along the axis of $\tau_2$.

Using Eq. (1.33), it follows that components $\|x_{1i*}\|\cos\theta_{\tau_1 x_{1i*}}$ of extreme vectors $x_{1i*}$ along the axis of $\tau_1$, wherein the axis of $\tau_1$ is determined by distributions of conditional likelihoods of extreme points $x_{1i*}$, and opposing components $-\|x_{1i*}\|\cos\theta_{\tau_2 x_{1i*}}$ of extreme vectors $x_{1i*}$ along the axis of $\tau_2$ wherein the axis of $\tau_2$ is determined by distributions of conditional likelihoods of extreme points $x_{2i*}$, are symmetrically balanced with components $\|x_{2i*}\|\cos\theta_{\tau_2 x_{2i*}}$ of extreme vectors $x_{2i*}$ along the axis of $\tau_2$, wherein the axis of $\tau_2$ is determined by distributions of conditional likelihoods of extreme points $x_{2*}$, and opposing components $-\|x_{2i*}\|\cos\theta_{\tau_1 x_{2i*}}$ of extreme vectors $x_{2i*}$ along the axis of $\tau_1$, wherein the axis of $\tau_1$ is determined by distributions of conditional likelihoods of extreme points $x_{1i*}$:

$$\lambda_{max_\psi}^{-1}\|\tau_1\|\sum_{i=1}^{l_1} comp_{\overrightarrow{\tau_1}}(\overrightarrow{x_{1i*}}) - \lambda_{max_\psi}^{-1}\|\tau_2\|\sum_{i=1}^{l_1} comp_{\overrightarrow{\tau_2}}(\overrightarrow{x_{1i*}}) =$$

$$\lambda_{max_\psi}^{-1}\|\tau_2\|\sum_{i=1}^{l_2} comp_{\overrightarrow{\tau_2}}(\overrightarrow{x_{2i*}}) - \lambda_{max_\psi}^{-1}\|\tau_1\|\sum_{i=1}^{l_2} comp_{\overrightarrow{\tau_1}}(\overrightarrow{x_{2i*}}),$$

wherein counteracting and opposing components of likelihoods of extreme vectors $x_{1i*}$ associated with counter risks and risks for class A, along the axis of $\tau$—are symmetrically balanced with counteracting and opposing components of likelihoods of extreme vectors $x_{2i*}$ associated with counter risks and risks for class B, along the axis of $-\tau$.

Now rewrite Eq. (1.33) as:

$$\lambda_{max_\psi}^{-1}\Sigma_{i=1}^{l_1}x_{1i*}^T\tau_1 + \lambda_{max_\psi}^{-1}\Sigma_{i=1}^{l_2}x_{2i*}^T\tau_1 =$$

$$\lambda_{max_\psi}^{-1}\Sigma_{i=1}^{l_1}x_{1i*}^T\tau_2 + \lambda_{max_\psi}^{-1}\Sigma_{i=1}^{l_2}x_{2i*}^T\tau_2 \quad (1.34)$$

wherein components of all of the extreme vectors $x_{1i*}$ and $x_{2i*}$ from class A and class B, along the axes of $\tau_1$ and $\tau_2$, satisfy the locus equation:

$$\left[\sum_{i=1}^{l_1} comp_{\overrightarrow{\tau_1}}(\overrightarrow{x_{1i*}}) + \sum_{i=1}^{l_2} comp_{\overrightarrow{\tau_1}}(\overrightarrow{x_{2i*}})\right]\lambda_{max_\psi}^{-1}$$

$$\|\tau_1\| = \left[\sum_{i=1}^{l_2} comp_{\overrightarrow{\tau_2}}(\overrightarrow{x_{2i*}}) + \sum_{i=1}^{l_1} comp_{\overrightarrow{\tau_2}}(\overrightarrow{x_{1i*}})\right]\lambda_{max_\psi}^{-1}\|\tau_2\|$$

wherein components of likelihoods of extreme vectors $x_{1i*}$ and $x_{2i*}$ associated with counter risks and risks for class A and class B—along the axis of $\tau_1$, are symmetrically balanced with components of likelihoods of extreme vectors $x_{1i*}$ and $x_{2i*}$ associated with counter risks and risks for class A and class B—along the axis of $\tau_2$.

Therefore, machine learning algorithms of the invention determine scale factors $\psi_{1i*}$ and $\psi_{2i*}$ for the geometric locus of signed and scaled extreme points in Eq. (1.11)

$$\tau = \tau_1 - \tau_2$$

$$= \sum_{i=1}^{l_1} \psi_{1i*}x_{1i*} - \sum_{i=1}^{l_2} \psi_{2i*}x_{2i*},$$

that satisfy suitable length constraints, wherein the principal eigenaxis of $\psi$ and the principal eigenaxis of $\tau$ are both formed by symmetrical distributions of likelihoods of extreme vectors $x_{1i*}$ and $x_{2i*}$ from class A and class B, wherein components of likelihoods of extreme vectors $x_{1i*}$ and $x_{2i*}$ associated with counter risks and risks for class A and class B are symmetrically balanced with each other: along the axis of $\psi_1$ and $\psi_2$ of the principal eigenaxis of $\psi$ and along the axis of $\tau_1$ and $\tau_2$ of the principal eigenaxis of $\tau$.

Given Eqs (1.33) and (1.34), it follows that the locus equation $$\lambda_{max_\psi}^{-1}(\Sigma_{i=1}^{l_1} + \Sigma_{i=1}^{l_2}x_{2i*})^T\{\tau_1-\tau_2\} = 0 \quad (1.35)$$

determines the primal equilibrium point of a minimum risk linear classification system—within a Wolfe dual principal eigenspace—wherein the form of Eq. (1.35) is determined by geometric and statistical conditions that are satisfied by the dual loci of $\psi$ and $\tau$.

A discriminant function of the invention satisfies the geometric locus of a linear decision boundary of a minimum risk linear classification system in terms of the critical minimum eigenenergy $\|Z|\tau\|_{min_c}^2$ and the minimum expected risk $\mathfrak{R}_{min}(Z\|\tau\|_{min_c}^2)$ exhibited by a dual locus $\tau$, wherein the total allowed eigenenergy $\|Z|\tau\|_{min_c}^2$ and the minimum expected risk $\mathfrak{R}_{min}(Z\|\tau\|_{min_c}^2)$ exhibited by the dual locus of determines the minimum expected risk $\mathfrak{R}_{min}(Z\|\tau\|_{min_c}^2)$ and the total allowed eigenenergy $\|Z|\tau\|_{min_c}^2$ exhibited by the minimum risk linear classification system.

The KKT condition in Eq. (1.7) on the Lagrangian function in Eq. (1.2) and the theorem of Karush, Kuhn, and Tucker determine the manner in which a discriminant function of the invention satisfies the geometric loci of the linear decision boundary in Eq. (1.15) and the linear decision borders in Eqs (1.16) and (1.17).

Accordingly, given a Wolfe dual geometric locus of scaled unit extreme vectors $$\psi = \sum_{i=1}^{l} \psi_{i*} \frac{x_{i*}}{\|x_{i*}\|},$$

wherein $\{\psi_{i*} > 0\}_{i=1}^{l}$ and $\sum_{i=1}^{l} \psi_{i*} y_i = 0$, it follows that the 1 likelihood components and corresponding principal eigenaxis components $\{\psi_{i*} x_{i*}\}_{i=1}^{l}$ on the dual locus of $\tau$ satisfy the system of locus equations:

$$\psi_{i*}[y_i(x_{i*}^T \tau + \tau_0) - 1 + \xi_i] = 0, \ i=1, \ldots, l \quad (1.36)$$

within the primal principal eigenspace of the minimum risk linear classification system, wherein either $\xi_i = \xi = 0$ or $\xi_i = \xi \ll 1$, e.g. $\xi_i = \xi = 0.02$.

Take the set $\{\psi_{1i*} x_{1i*}\}_{i=1}^{l_1}$ of $l_1$ scaled extreme vectors that belong to class A. Using Eq. (1.36) and letting $y_i = +1$, it follows that the total allowed eigenenergy and the minimum expected risk exhibited by $\tau_1$ are both determined by the identity $$\|Z|\tau_1\|_{min_c}^2 - \|\tau_1\|\|\tau_2\|\cos\theta_{\tau_1\tau_2} = \sum_{i=1}^{l_1} \psi_{1i*}(1-\xi_i-\tau 0), \quad (1.37)$$

wherein the constrained discriminant function $s^T\tau + \tau_0 = +1$ satisfies the geometric locus of the linear decision border in Eq. (1.16) in terms of the critical minimum eigenenergy $\|Z|\tau_1\|_{min_c}^2$ and the minimum expected risk $\mathfrak{R}_{min}(Z\|\tau_1\|_{min_c}^2)$ exhibited by $\tau_1$, and wherein the eigenenergy functional $\|Z|\tau_1\|_{min_c}^2 - \|\tau_1\|\|\tau_2\|\cos\theta_{\tau_1\tau_2}$ is equivalent to the functional $\sum_{i=1}^{l_1} \psi_{1i*}(1-\xi_i-\tau 0)$ within the primal principal eigenspace of the dual locus of $\tau_1 - \tau_2$, and wherein $\tau_1$ and $\psi_1$ are symmetrically and equivalently related to each other within the Wolfe dual-principal eigenspace.

Take the set $\{\psi_{2i*} x_{2i*}\}_{i=1}^{l_2}$ of $l_2$ scaled extreme vectors that belong to class B. Using Eq. (1.36) and letting $y_i = 1$, it follows that the total allowed eigenenergy and the minimum expected risk exhibited by $\tau_2$ are both determined by the identity $$\|Z|\tau_2\|_{min_c}^2 - \|\tau_2\|\|\tau_1\|\cos\theta_{\tau_2\tau_1} = \sum_{i=1}^{l_2} \psi_{2i*}(1-\xi_i-\tau 0), \quad (1.38)$$

wherein the constrained discriminant function $s^T\tau + \tau_0 = -1$ satisfies the geometric locus of the linear decision border in Eq. (1.17) in terms of the critical minimum eigenenergy $\|Z|\tau_2\|_{min_c}^2$ and the minimum expected risk $\mathfrak{R}_{min}(Z\|\tau_2\|_{min_c}^2)$ exhibited by $\tau_2$ and wherein the eigenenergy functional $\|Z|\tau_2\|_{min_c}^2 - \|\tau_2\|\|\tau_1\|\cos\theta_{\tau_2\tau_1}$ is equivalent to the functional $\sum_{i=1}^{l_2} \psi_{2i*}(1-\xi_i+\tau_0)$ within the primal principal eigenspace of the dual locus of $\tau_1 - \tau_2$, and wherein $\tau_2$ and $\psi_2$ are symmetrically and equivalently related to each other within the Wolfe dual-principal eigenspace.

Summation over the complete system of locus equations that are satisfied by $\tau_1$ $$(\sum_{i=1}^{l_1} \psi_{1i*} x_{1i*}^T)\tau = \sum_{i=1}^{l_1} \psi_{1i*}(1-\xi_i+\tau_0)$$

and by $\tau_2$ $$(-\sum_{i=1}^{l_2} \psi_{2i*} x_{2i*}^T)\tau = \sum_{i=1}^{l_2} \psi_{2i*}(1-\xi_i+\tau_0),$$

and using the equilibrium constraint on the dual locus of $\psi$ in Eq. (1.22), wherein the principal eigenaxis of $\psi$ is in statistical equilibrium, produces the identity that determines the total allowed eigenenergy $\|Z|\tau\|_{min_c}^2$ and the minimum expected risk $\mathfrak{R}_{min}(Z\|\tau\|_{min_c}^2)$ exhibited by the dual locus of $\tau$:

$$(\tau_1 - \tau_2)^T \tau \equiv \sum_{i=1}^{l_1} \psi_{1i*}(1-\xi_i-\tau_0) + \sum_{i=1}^{l_2} \psi_{2i*}(1-\xi_i+\tau_0) \quad (1.39)$$

$$\equiv \sum_{i=1}^{l} \psi_{i*}(1-\xi_i),$$

wherein the constrained discriminant function $s^T\tau + \tau_0 = 0$ satisfies the geometric locus of the linear decision boundary in Eq. (1.15) in terms of the critical minimum eigenenergy $\|Z|\tau_1-\tau_2\|_{min_c}^2$ and the minimum expected risk $\mathfrak{R}_{min}(Z\|\tau_1-\tau_2\|_{min_c}^2)$ exhibited by the dual locus of $\tau$, and wherein the eigenenergy functional $\|Z|\tau_1-\tau_2\|_{min_c}^2$ is equivalent to the functional:

$$\|Z|\tau\|_{min_c}^2 \equiv \sum_{i=1}^{l_1} \psi_{1i*} \frac{x_{1i*}}{\|x_{1i*}\|}(1-\xi_i-\tau_0) + \sum_{i=1}^{l_2} \psi_{2i*} \frac{x_{2i*}}{\|x_{2i*}\|}(1-\xi_i+\tau_0)$$

$$\equiv \sum_{i=1}^{l} \psi_{i*} \frac{x_{i*}}{\|x_{i*}\|}(1-\xi_i),$$

within the primal principal eigenspace of the dual locus of $\tau_1 - \tau_2$, and wherein the dual loci of $\tau$ and $\psi$ are symmetrically and equivalently related to each other within the Wolfe dual-principal eigenspace.

Given Eq. (1.39), it follows that the total allowed eigenenergy $\|Z|\tau_1-\tau_2\|_{min_c}^2$ and the minimum expected risk $\mathfrak{R}_{min}(Z\|\tau_1-\tau_2\|_{min_c}^2)$ exhibited by the dual locus of $\tau$ are both determined by the integrated magnitudes $\psi_{i*}$ of the principal eigenaxis components on the dual locus of $\psi$ $$(\tau_1-\tau_2)\tau = \sum_{i=1}^{l} \psi_{i*}(1-\xi_i) = \sum_{i=1}^{l} \psi_{i*} - \sum_{i=1}^{l} \psi_{i*}\xi_i,$$

wherein regularization parameters $\xi_i = \xi \ll 1$ determine negligible constraints on the minimum expected risk $\mathfrak{R}_{min}(Z\|\tau_1-\tau_2\|_{min_c}^2)$ and the total allowed eigenenergy $|Z|\tau_1-\tau_2\|_{min_c}^2$ exhibited by the dual locus of $\tau$.

Now, take any given collection $\{x_i\}_{i=1}^{N}$ of feature vectors $x_i$ that are inputs to one of the machine learning algorithm of the invention, wherein each feature vector $x_i$ has a label $y_i$, wherein $y_i = +1$ if $x_i \in A$ and $y_i = -1$ if $x_i \in B$.

The system of locus equations in Eqs (1.37)-(1.39) determines the manner in which a constrained discriminant function of the invention satisfies parametric, primary and secondary integral equations of binary classification over the decision space of a minimum risk linear classification system of the invention. The primary integral equation is devised first.

Using Eq. (1.11), Eq. (1.13), Eq. (1.22) and Eqs (1.37)-(1.39), it follows that the constrained discriminant function $$D(s) = s^T \tau - \left(\frac{1}{l}\sum_{i=1}^{l} x_{i*}^T\right)\tau + \frac{1}{l}\sum_{i=1}^{l} y_i(1-\xi_i):$$

$$D(s) = 0, \ D(s) = +1, \text{ and } D(s) = -1,$$

satisfies the locus equations $$\|Z|\tau_1\|_{min_c}^2 - \|\tau_1\|\|\tau_2\|\cos\theta_{\tau_1\tau_2} + \delta(y)\Sigma_{i=1}^{l_1}\psi_{1i*} = \frac{1}{2}\|Z|\tau_1 - \tau_2\|_{min_c}^2 \quad (1.40)$$

and $$\|Z|\tau_2\|_{min_c}^2 - \|\tau_2\|\|\tau_1\|\cos\theta_{\tau_2\tau_1} - \delta(y)\Sigma_{i=1}^{l_2}\psi_{2i*} = \frac{1}{2}\|Z|\tau_1 - \tau_2\|_{min_c}^2 \quad (1.41)$$

over the decision regions $Z_1$ and $Z_2$ of the decision space $Z$ of the minimum risk linear classification system $$s^T\tau + \tau_0 \underset{B}{\overset{A}{\gtreqless}} 0,$$

wherein the parameters $\delta(y)\Sigma_{i=1}^{l_1}\psi_{1i*}$ and $-\delta(y)\Sigma_{i=1}^{l_2}\psi_{2i*}$:

$$\delta(y) \triangleq \frac{1}{l}\sum_{i=1}^{l} y_i(1-\xi_i)$$

are equalizer statistics.

Using Eqs (1.40) and (1.41) along with the identity in Eq. (1.31)

$$\Sigma_{i=1}^{l_1}\psi_{1i*} = \lambda_{max_\psi}^{-1}\Sigma_{i=1}^{l_1}x_{1i*}^T(\Sigma_{j=1}^{l_1}\psi_{1j*}x_{1j*} - \Sigma_{j=1}^{l_2}\psi_{2j*}x_{2j*}),$$

and the identity in Eq. (1.32)

$$\Sigma_{i=1}^{l_2}\psi_{2i*} = \lambda_{max_\psi}^{-1}\Sigma_{i=1}^{l_2}x_{2i*}^T(\Sigma_{j=1}^{l_2}\psi_{2j*}x_{2j*} - \Sigma_{j=1}^{l_1}\psi_{1j*}x_{1j*}),$$

it follows that the constrained discriminant function satisfies the locus equation over the decision regions $Z_1$ and $Z_2$ of the decision space $Z$ of the minimum risk linear classification system:

$$\|Z|\tau_1\|_{min_c}^2 - \|\tau_1\|\|\tau_2\|\cos\theta_{\tau_1\tau_2}\delta(y)\lambda_{max_\psi}^{-1}\Sigma_{i=1}^{l_1}x_{1i*}^T\tau$$

$$= \|Z|\tau_2\|_{min_c}^2 - \|\tau_2\|\|\tau_1\|\cos\theta_{\tau_2\tau_1}\delta(y)\lambda_{max_\psi}^{-1}\Sigma_{i=1}^{l_2}x_{2i*}^T\tau, \quad (1.42)$$

wherein both the left-hand side and the right-hand side of Eq. (1.42) satisfy half the total allowed eigenenergy $\|Z|\tau_1-\tau_2\|_{min_c}^2$ and half the minimum expected risk $\Re_{min}(Z\|\|\tau_1-\tau_2\|_{min_c}^2)$ exhibited by the minimum risk linear classification system $$s^T\tau + \tau_0 \underset{B}{\overset{A}{\gtreqless}} 0.$$

Returning to the integral in Eq. (1.29):

$$P = (x_{1i*}|\tau_1) = \int_Z \tau_1 d\tau_1 = \|Z|\tau_1\|_{min_c}^2 + C_1,$$

wherein the above integral determines a conditional probability $P(x_{1i*}|\tau_1)$ for class A, and to the integral in Eq. (1.30)

$$P = (x_{2i*}|\tau_2) = \int_Z \tau_2 d\tau_2 = \|Z|\tau_2\|_{min_c}^2 + C_2,$$

wherein the above integral determines a conditional probability $P(x_{2i*}|\tau_2)$ for class B, it follows that the value for the integration constant $C_1$ in Eq. (1.29) is: $C_1 = -\|\tau_1\|\|\tau_2\|\cos\theta_{\tau_1\tau_2}$, and the value for the integration constant $C_2$ in Eq. (1.30) is: $C_2 = -\|\tau_2\|\|\tau_1\|\cos\theta_{\tau_2\tau_1}$.

Substituting the value for $C_1$ into Eq. (1.29), and using Eq. (1.29) and Eq. (1.42), it follows that the conditional probability $P(x_{1i*}|\tau_1)$ for class A, wherein the integral of the conditional density function $p(x_{1i*}|\tau_1)$ for class A is given by the integral:

$$\begin{aligned}
P(x_{1i*}|\tau_1) &= \int_Z p(x_{1i*}|\tau_1)d\tau_1 + \delta(y)\lambda_{max_\psi}^{-1}\sum_{i=1}^{l_1} x_{1i*}^T(\tau_1-\tau_2) \\
&= \int_Z \tau_1 d\tau_1 + \delta(y)\lambda_{max_\psi}^{-1}\sum_{i=1}^{l_1} x_{1i*}^T(\tau_1-\tau_2) \\
&= \|Z|\tau_1\|_{min_c}^2 - \|\tau_1\|\|\tau_2\|\cos\theta_{\tau_1\tau_2} + \\
&\quad \delta(y)\lambda_{max_\psi}^{-1}\sum_{i=1}^{l_1} x_{1i*}^T(\tau_1-\tau_2) \\
&\equiv \frac{1}{2}\|Z|\tau_1-\tau_2\|_{min_c}^2 \\
&\equiv \frac{1}{2}\Re_{min}(Z\|\|\tau_1-\tau_2\|_{min_c}^2),
\end{aligned} \quad (1.43)$$

over the decision space $Z=Z_1+Z_2$ of the minimum risk linear classification system, is determined by half the total allowed eigenenergy $\frac{1}{2}\|Z|\tau_1-\tau_2\|_{min_c}^2$ and half the minimum expected risk $\frac{1}{2}\Re_{min}(Z\|\|\tau_1-\tau_2\|_{min_c}^2)$ that is exhibited by the dual locus of $\tau=t_1-\tau_2$.

Substituting the value for $C_2$ into Eq. (1.30), and using Eq. (1.30) and Eq. (1.42), it follows that the conditional probability $P(x_{2i}|\tau_2)$ for class B, wherein the integral of the conditional density function $p(x_{2i*}|\tau_2)$ for class B is given by the integral:

$$\begin{aligned}
P(x_{2i*}|\tau_2) &= \int_Z p(x_{2i*}|\tau_2)d\tau_2 + \delta(y)\lambda_{max_\psi}^{-1}\sum_{i=1}^{l_2} x_{2i*}^T(\tau_1-\tau_2) \\
&= \int_Z \tau_2 d\tau_2 + \delta(y)\lambda_{max_\psi}^{-1}\sum_{i=1}^{l_2} x_{2i*}^T(\tau_1-\tau_2) \\
&= \|Z|\tau_2\|_{min_c}^2 - \|\tau_2\|\|\tau_1\|\cos\theta_{\tau_2\tau_1} + \\
&\quad \delta(y)\lambda_{max_\psi}^{-1}\sum_{i=1}^{l_2} x_{2i*}^T(\tau_1-\tau_2) \\
&\equiv \frac{1}{2}\|Z|\tau_1-\tau_2\|_{min_c}^2 \\
&\equiv \frac{1}{2}\Re_{min}(Z\|\|\tau_1-\tau_2\|_{min_c}^2),
\end{aligned} \quad (1.44)$$

over the decision space $Z=Z_1+Z_2$ of the minimum risk linear classification system, is determined by half the total allowed eigenenergy $\frac{1}{2}\|Z|\tau_1-\tau_2\|_{min_c}^2$ and half the minimum expected risk $\frac{1}{2}\Re_{min}(Z\|\|\tau_1-\tau_2\|_{min_c}^2)$ that is exhibited by the dual locus of $\tau=t_1-\tau_2$.

Given Eqs (1.43) and (1.44), it follows that the integral of the conditional density function $p(x_{1i*}|\tau_1)$ for class A and the integral of the conditional density function $p(x_{2i*}|\tau_2)$ for class B are both constrained to satisfy half the total allowed eigenenergy $\frac{1}{2}\|Z|\tau_1-\tau_2\|_{min_c}^2$ and half the minimum expected risk $\frac{1}{2}\mathfrak{R}_{min}(Z\|\tau_1-\tau_2\|_{min_c}^2)$ that is exhibited by the minimum risk linear classification system $$s^T\tau + \tau_0 \underset{B}{\overset{A}{\gtreqless}} 0.$$

Therefore, the conditional probability $P(x_{1i*}|\tau_1)$ of observing the set $\{x_{1i*}\}_{i=1}^{l_1}$ of $l_1$ extreme points $x_{1i*}$ from class A within localized regions of the decision space $Z=Z_1+Z_2$ of the minimum risk linear classification system is equal to the conditional probability $P(x_{2i*}|\tau_2)$ of observing the set $\{x_{2i*}\}_{i=1}^{l_2}$ of $l_2$ extreme points $x_{2i*}$ from class B within localized regions of the decision space $Z=Z_1+Z_2$ of the minimum risk linear classification system, wherein $P(x_{1i*}|\tau_1)=P(x_{2i*}|\tau_2)$, and wherein all of the extreme points belong to the collection of feature vectors $\{x_i\}_{i=1}^N$ that are inputs to a machine learning algorithm of the invention, wherein distributions of the feature vectors have similar covariance matrices.

Therefore, minimum risk linear classification systems of the invention exhibit a novel property of computer-implemented linear classification systems, wherein for any given collection of feature vectors $\{x_i\}_{i=1}^N$ that are inputs to one of the machine learning algorithms of the invention, wherein distributions of the feature vectors have similar covariance matrices: (1) the conditional probability, (2) the minimum expected risk, and (3) the total allowed eigenenergy exhibited by a minimum risk linear classification system for class A is equal to (1) the conditional probability, (2) the minimum expected risk, and (3) the total allowed eigenenergy exhibited by the minimum risk linear classification system for class B.

Using Eqs (1.43) and (1.44), it follows that the constrained discriminant function of the invention $$D(s) = s^T\tau - \left(\frac{1}{l}\sum_{i=1}^{l} x_i^T\right)\tau + \frac{1}{l}\sum_{i=1}^{l} y_i(1-\xi_i): D(s) = 0,$$

$$D(s) = +1, \text{ and } D(s) = -1,$$

is the solution of the parametric, fundamental integral equation of binary classification:

$$f_1(D(s)) = \int_{Z_1} \tau_1 d\tau_1 + \int_{Z_2} \tau_1 d\tau_1 + \delta(y)\lambda_{max_\psi}^{-1}\sum_{i=1}^{l_1} x_{1i*}^T(\tau_1-\tau_2) \quad (1.45)$$

$$= \int_{Z_1} \tau_2 d\tau_2 + \int_{Z_2} \tau_2 d\tau_2 + \delta(y)\lambda_{max_\psi}^{-1}\sum_{i=1}^{l_2} x_{2i*}^T(\tau_1-\tau_2),$$

over the decision space $Z=Z_1+Z_2$ of the minimum risk linear classification system $$s^T\tau + \tau_0 \underset{B}{\overset{A}{\gtreqless}} 0$$

of the invention, wherein the decision space Z is spanned by symmetrical decision regions $Z_1+Z_2=Z:Z_1\approx Z_2$ and wherein the conditional probability $P(Z_1|\tau_1)$ and the counter risk $\overline{\mathfrak{R}}_{min}(Z_1\|\tau_1\|_{min_c}^2)$ and the eigenenergy $\|Z_1|\tau_1\|_{min_c}^2$ of class A:within the $Z_1$ decision region, and the conditional probability $P(Z_2|\tau_1)$ and the risk $\mathfrak{R}_{min}(Z_2\|\tau_1\|_{min_c}^2)$ and the eigenenergy $\|Z_2|\tau_1\|_{min_c}^2$ of class A:within the $Z_2$ decision region—are symmetrically balanced with—the conditional probability $P(Z_1|\tau_2)$ and the risk $\mathfrak{R}_{min}(Z_1\|\tau_2\|_{min_c}^2)$ and the eigenenergy $\|Z_1|\tau_2\|_{min_c}^2$ of class B:within the $Z_1$ decision region, and the conditional probability $P(Z_2|\tau_2)$ and the counter risk $\overline{\mathfrak{R}}_{min}(Z_2\|\tau_2\|_{min_c}^2)$ and the eigenenergy $\|Z_2|\tau_2\|_{min_c}^2$ of class B:within the $Z_2$ decision region, and wherein the conditional probability $P(Z|\tau_1-\tau_2)$ and the minimum expected risk $\mathfrak{R}_{min}(Z\|\tau_1-\tau_2\|_{min_c}^2)$ and the total allowed eigenenergy $\|Z|\tau_1-\tau_2\|_{min_c}^2$ exhibited by the minimum risk linear classification system are jointly regulated by the primal equilibrium point:

$$\lambda_{max_\psi}^{-1}(\Sigma_{i-1}^{l_1} x_{1i*} + \Sigma_{i=1}^{l_2} x_{2i*})^T\{\tau_1-\tau_2\}=0$$

and the Wolfe dual equilibrium point:

$$\sum_{i=1}^{l_1} \psi_{1i*} \frac{x_{1i*}}{\|x_{1i*}\|} - \sum_{i=1}^{l_2} \psi_{2i*} \frac{x_{2i*}}{\|x_{2i*}\|} = 0$$

of the integral equation $f_1(D(s))$.

Further, the novel principal eigenaxis of the invention that determines discriminant functions of the invention along with minimum risk linear classification systems of the invention satisfies the law of cosines in the symmetrically balanced manner that is outlined below.

Any given geometric locus of signed and scaled extreme points:

$$\tau = \sum_{i=1}^{l_1} \psi_{1i*} x_{1i*} - \sum_{i=1}^{l_2} \psi_{2i*} x_{2i*} = \tau_1 - \tau_2,$$

wherein the geometric locus of a principal eigenaxis $\tau$ determines a dual locus of likelihood components and principal eigenaxis components $\tau=\tau_i-\tau_2$ that represents a discriminant function $D(s)=S^T\tau+\tau_0$ of the invention, wherein principal eigenaxis components and corresponding likelihood components $\psi_{1i*} x_{1i*}$ and $\psi_{2i*} x_{2i*}$ on the dual locus of $\tau_1-\tau_2$ determine conditional densities and conditional likelihoods for respective extreme points $x_{1i*}$ and $x_{2i*}$, and wherein the geometric locus of the principal eigenaxis $\tau$ determines an intrinsic coordinate system $\tau_1-\tau_2$ of a linear decision boundary $s^T\tau+\tau_0=0$ and an eigenaxis of symmetry $$\left(s - \frac{1}{l}\sum_{i=1}^{l_1} x_{i*}\right)^T (\tau_1 - \tau_2)$$

for the decision space $Z_1+Z_2=Z:Z_1\approx Z_2$ of a minimum risk linear classification $$s^T\tau + \tau_0 \underset{B}{\overset{A}{\gtreqless}} 0$$

of the invention, satisfies the law of cosines $$\|\tau\|^2_{min_c} = \|\tau_1 - \tau_2\|^2_{min_c}$$
$$= \|\tau_1\|^2_{min_c} + \|\tau_2\|^2_{min_c} - 2\|\tau_1\|\|\tau_2\|\cos\theta_{\tau_1\tau_2}$$

in the symmetrically balanced manner:

$$\frac{1}{2}\|\tau\|^2_{min_c} = \|\tau_1\|^2_{min_c} - \|\tau_1\|\|\tau_2\|\cos\theta_{\tau_1\tau_2}$$
$$= \|\tau_2\|^2_{min_c} - \|\tau_2\|\|\tau_1\|\cos\theta_{\tau_2\tau_1},$$

wherein $\theta$ is the angle between $\tau_1$ and $\tau_2$ and wherein the dual locus of likelihood components and principal eigenaxis components exhibits symmetrical dimensions and density, wherein the total allowed eigenenergy $\|\tau_1\|_{min_c}^2$ exhibited by the dual locus of components $p(x_{1i*}|\tau_1)$ given class A is symmetrically balanced with the total allowed eigenenergy $\|\tau_2\|_{min_c}^2$ exhibited by the dual locus of components $p(x_{2i*}|\tau_2)$ given class B:

$$\|\tau_1\|_{min_c}^2 = \|\tau_2\|_{min_c}^2,$$

wherein the length of side $\tau_1$ equals the length of side $\tau_2$ $$\|\tau_1\| = \|\tau_2\|,$$

and wherein components of likelihood components and principal eigenaxis components of class A—along the axis of $t_1$—are symmetrically balanced with components of likelihood components and principal eigenaxis components of class B—along the axis of $\tau_2$:

$$\|\tau_1\|\Sigma_{i=1}^{l_1}comp_{\overrightarrow{\tau_1}}(\overrightarrow{\psi_{1i*}x_{1i*}}) = \|\tau_2\|\Sigma_{i=1}^{l_2}comp_{\overrightarrow{\tau_2}}(\overrightarrow{\psi_{2i*}x_{2i*}}),$$

wherein components of critical minimum eigenenergies exhibited by scaled extreme vectors from class A and corresponding counter risks and risks for class A—along the axis of $\tau_1$, are symmetrically balanced with components of critical minimum eigenenergies exhibited by scaled extreme vectors from class B and corresponding counter risks and risks for class B—along the axis of $\tau_2$ and wherein the opposing component of $\tau_2$—along the axis of $\tau_1$, is symmetrically balanced with the opposing component of $\tau_1$—along the axis of $\tau_2$:

$$\|\tau_1\|[-\|\tau_2\|\cos\theta\tau_1\tau_2] = \|\tau_2\|[-\|\tau_1\|\cos\theta\tau_2\tau_1],$$

wherein opposing components of likelihood components and principal eigenaxis components of class B—along the axis of $\tau_1$, are symmetrically balanced with opposing components of likelihood components and principal eigenaxis components of class A—along the axis of $\tau_2$:

$$\|\tau_1\|\Sigma_{i=1}^{l_2}-comp_{\overrightarrow{\tau_1}}(\overrightarrow{\psi_{2i*}x_{2i*}}) = \|\tau_2\|\Sigma_{i=1}^{l_1}-comp_{\overrightarrow{\tau_2}}(\overrightarrow{\psi_{1i*}x_{1i*}}),$$

wherein opposing components of critical minimum eigenenergies exhibited by scaled extreme vectors from class B and corresponding counter risks and risks for class B—along the axis of $\tau_1$, are symmetrically balanced with opposing components of critical minimum eigenenergies exhibited by scaled extreme vectors from class A and corresponding counter risks and risks for class A—along the axis of $\tau_2$ and wherein opposing and counteracting random forces and influences of the minimum risk linear classification system of the invention are symmetrically balanced with each other—about the geometric center of the dual locus $\tau$:

$$\|\tau_1\|\left(\sum_{i=1}^{l_1}comp_{\overrightarrow{\tau_1}}(\overrightarrow{\psi_{1i*}x_{1i*}}) - \sum_{i=1}^{l_2}comp_{\overrightarrow{\tau_1}}(\overrightarrow{\psi_{2i*}x_{2i*}})\right) =$$
$$\|\tau_2\|\left(\sum_{i=1}^{l_2}comp_{\overrightarrow{\tau_2}}(\overrightarrow{\psi_{2i*}x_{2i*}}) - \sum_{i=1}^{l_1}comp_{\overrightarrow{\tau_2}}(\overrightarrow{\psi_{1i*}x_{1i*}})\right),$$

—wherein the statistical fulcrum of $\tau$ is located.

Figure 12:
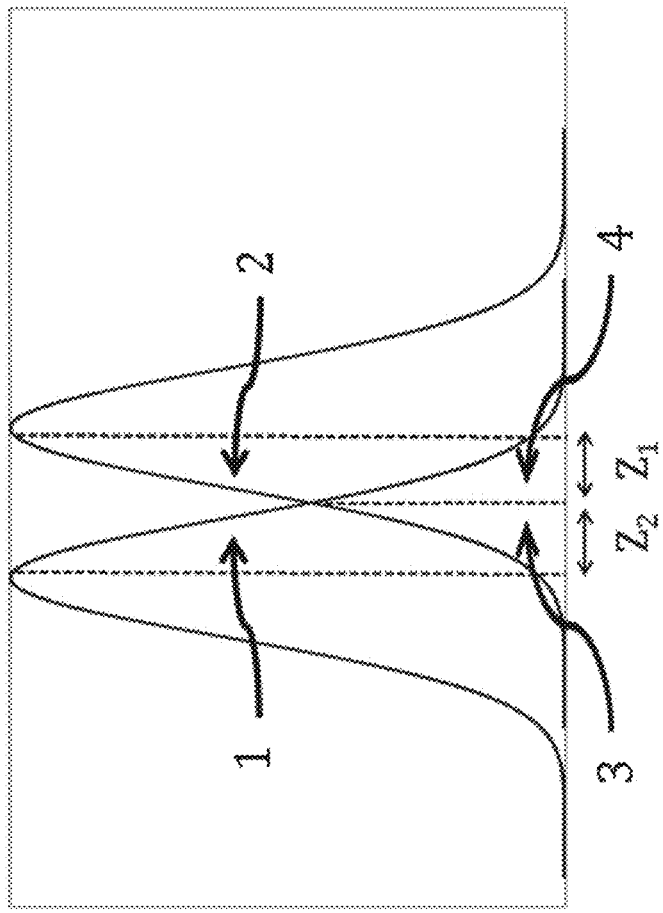
FIG. 12 illustrates regions of counter risk and regions of risk within decision regions of linear classification systems in which distributions of two collections of feature vectors are overlapping with each other.

Accordingly, counteracting and opposing components of critical minimum eigenenergies exhibited by all of the scaled extreme vectors on the geometric locus of the principal eigenaxis $\tau=\tau_1-\tau_2$ of the invention, along the axis of the principal eigenaxis $\tau$, and corresponding counter risks and risks exhibited by the minimum risk linear classification system $$s^T\tau + \tau_0 \overset{A}{\underset{B}{\gtreqless}} 0$$

of the invention, are symmetrically balanced with each other about the geometric center of the dual locus $\tau$, wherein the statistical fulcrum of $\tau$ is located. FIG. 12 illustrates regions of counter risk and regions of risk within the decision regions of a minimum risk linear classification system in which distributions of feature vectors are overlapping with each other.

Now, take the previous collection $\{x_i\}_{i=1}^N$ of labeled feature vectors $x_i$ that are inputs to one of the machine learning algorithm of the invention, wherein each feature vector $x_i$ has a label $y_i$, wherein $y_i=+1$ if $x_i \in A$ and $y_i=-1$ if $x_i \in B$, and wherein distributions of the feature vectors have similar covariance matrices.

Given that a constrained discriminant function of the invention $$D(s) = \left(s - \frac{1}{l}\sum_{i=1}^{l}x_{i*}\right)^T \tau_1 - \left(s - \frac{1}{l}\sum_{i=1}^{l}x_{i*}\right)^T \tau_2 + \frac{1}{l}\sum_{i=1}^{l}y_i(1-\xi_i):\ D(s) = 0,$$

$$D(s) = +1, \text{ and } D(s) = -1,$$

is the solution of the parametric, fundamental integral equation of binary classification in Eq. (1.45), and given that the discriminant function is represented by a dual locus of likelihood components and principal eigenaxis components $\tau=\tau_1-\tau_2$ that satisfies the law of cosines in the symmetrically balanced manner outlined above, it follows that the constrained discriminant function satisfies the parametric, secondary integral equation of binary classification:

$$f_2(D(S)): \int_{Z_1}\tau_1 d\tau_1 - \int_{Z_1}\tau_2 d\tau_2 + \delta(y)\lambda_{max_\psi}^{-1}\Sigma_{i=1}^{l_1}x_{1i*}^T(\tau_1-\tau_2) =$$

$$\int_{Z_2}\tau_2 d\tau_2 - \int_{Z_2}\tau_1 d\tau_1 + \delta(y)\lambda_{max_\psi}^{-1}\Sigma_{i=1}^{l_2}x_{2i*}^T(\tau_1-\tau_2),$$

over the $Z_1$ and $Z_2$ decision regions of a minimum risk linear classification system, wherein opposing and counteracting random forces and influences of the minimum risk linear classification system are symmetrically balanced with each other—within the $Z_1$ and $Z_2$ decision regions—in the following manners: (1) the eigenenergy $\|Z_1|\tau_1\|_{min_c}^2$ and the counter risk $\bar{\mathfrak{R}}_{min}(Z_1\|\tau_1\|_{min_c}^2)$ and the conditional probability $P(Z_1|\tau_1)$ of class A are symmetrically balanced with the opposing eigenenergy $\|Z_1|\tau_2\|_{min_c}^2$, and the opposing risk $\mathfrak{R}_{\min}(Z_1\|\tau_2\|_{min_c}^2)$ and the opposing conditional probability $P(Z_1|\tau_2)$ of class B:within the $Z_1$ decision region; (2) the eigenenergy $\|Z_2|\tau_2\|_{min_c}^2$ and the counter risk $\overline{\mathfrak{R}}_{\min}(Z_2\|\tau_2\|_{min_c}^2)$ and the conditional probability $P(Z_2|\tau_2)$ of class B is symmetrically balanced with the opposing eigenenergy $\|Z_2|\tau_1\|_{min_c}^2$ and the opposing risk $\mathfrak{R}_{\min}(Z_2\|\tau_1\|_{min_c}^2)$ and the opposing conditional probability $P(Z_2|\tau_1)$ of class A:within the $Z_2$ decision region; (3) the eigenenergy $\|Z_1|\tau_1\|_{min_c}^2$ and the counter risk $\overline{\mathfrak{R}}_{\min}(Z_1\|\tau_1\|_{min_c}^2)$ and the conditional probability $P(Z_1|\tau_1)$ of class A and the opposing eigenenergy $\|Z_1|\tau_2\|_{min_c}^2$ and the opposing risk $\mathfrak{R}_{\min}(Z_1\|\tau_2\|_{min_c}^2)$ and the opposing conditional probability $P(Z_1|\tau_2)$ of class B:within the $Z_1$ decision region—are symmetrically balanced with the eigenenergy $\|Z_2|\tau_2\|_{min_c}^2$ and the counter risk $\overline{\mathfrak{R}}_{\min}(Z_2\|\tau_2\|_{min_c}^2)$ and the conditional probability $P(Z_2|\tau_2)$ of class B and the opposing eigenenergy $\|Z_2|\tau_1\|_{min_c}^2$ and the opposing risk $\mathfrak{R}_{\min}(Z_2\|\tau_1\|_{min_c}^2)$ and the opposing conditional probability $P(Z_2|\tau_1)$ of class A:within the $Z_2$ decision region, wherein the minimum risk linear classification system satisfies a state of statistical equilibrium, wherein the expected risk $\mathfrak{R}_{\min}(Z\|\tau_1-\tau_2\|_{min_c}^2)$ and the total allowed eigenenergy $\|Z|\tau_1-\tau_2\|_{min_c}^2$ exhibited by the minimum risk linear classification system are minimized, and wherein the minimum risk linear classification system exhibits the minimum probability of error for feature vectors that belong to and are related to the given collection $\{x_i\}_{i=1}^N$ of feature vectors, wherein distributions of the feature vectors have similar covariance matrices.

Therefore, minimum risk linear classification systems of the invention exhibit a novel and useful property, wherein for any given collection of labeled feature vectors that are inputs to a machine learning algorithm of the invention, wherein distributions of the feature vectors have similar covariance matrices, the minimum risk linear classification system determined by the machine learning algorithm satisfies a state of statistical equilibrium, wherein the expected risk and the total allowed eigenenergy exhibited by the minimum risk linear classification system are minimized, and the minimum risk linear classification system exhibits the minimum probability of error for classifying the collection of feature vectors and feature vectors related to the collection into two classes, wherein the distributions of the feature vectors have similar covariance matrices.

Further, discriminant functions of minimum risk linear classification systems of the invention exhibit a novel and useful property, wherein a discriminant function D(s) of a minimum risk linear classification system is determined by a linear combination of a collection of extreme vectors $x_{i*}$, a collection of signed and scaled extreme vectors $\psi_{1i*}x_{1i*}$ and $-\psi_{2i*}x_{2i*}$, a collection of signs $y_i=+1$ or $y_i=-1$ associated with the extreme vectors $x_{i*}$, and a collection of regularization parameters $\xi_i=\xi=0$ or $\xi_i=\xi\ll1$:

$$D(s) = \left(s - \frac{1}{l}\sum_{i=1}^{l} x_{i*}\right)^T \left(\sum_{i=1}^{l_1} \psi_{1i*}x_{1i*} - \sum_{i=1}^{l_2} \psi_{2i*}x_{2i*}\right) + \frac{1}{l}\sum_{i=1}^{l} y_i(1-\xi_i),$$

wherein the collection of extreme vectors $\{x_{i*}\}_{i=1}^l$ belong to a collection of feature vectors $\{x_i\}_{i=1}^N$ that are inputs to one of the machine learning algorithms of the invention, and wherein the scales of the extreme vectors are determined by the machine learning algorithm used to determine the discriminant function D(s) of the minimum risk linear classification system sign(D(s)) that classifies the collection of feature vectors $\{x_i\}_{i=1}^N$ into two classes:

$$\text{sign}(D(s)) \overset{\Delta}{=} s^T\tau + \tau_0 \overset{A}{\underset{B}{\gtreqless}} 0,$$

wherein the output of the minimum risk linear classification system sign(D(s)) is related to the two classes, and wherein the minimum risk linear classification system sign(D(s)) exhibits the minimum probability of error for classifying feature vectors that belong to and are related to the collection of feature vectors used to determine the system sign(D(s)), wherein distributions of the feature vectors have similar covariance matrices.

Therefore, a discriminant function D(s) of a minimum risk linear classification system sign(D(s)) provides a scalable module that can be used to determine an ensemble $E=\Sigma_{j=1}^{M-1}\text{sign}(D_{ij}(s))$ of discriminant functions of minimum risk linear classification systems, wherein the ensemble of M-1 discriminant functions of M-1 minimum risk linear classification systems exhibits the minimum probability of error for classifying feature vectors that belong to and are related to M given collections of feature vectors.

More specifically, discriminant functions of minimum risk linear classification systems provide scalable modules that are used to determine a discriminant function of an M-class minimum risk linear classification system that classifies feature vectors into M classes, wherein the total allowed eigenenergy and the minimum expected risk that is exhibited by the M- class minimum risk linear classification system is determined by the total allowed eigenenergy and the minimum expected risk that is exhibited by M ensembles of M-1 discriminant functions of M-1 minimum risk linear classification systems $E_M=\tau_{i=1}^M\Sigma_{j=1}^{M-1}\text{sign}(D_{ij}(s))$, wherein each minimum risk linear classification system sign($D_{ij}(s)$) of an ensemble $E_{c_i}\Sigma_{j=1}^{M-1}\text{sign}(D_{ij}(s))$ for a given class $c_i$ exhibits a total allowed eigenenergy and a minimum expected risk that is minimum for a given collection of feature vectors, wherein distributions of the feature vectors have similar covariance matrices, and wherein the total allowed eigenenergy and the expected risk that is exhibited by the ensemble $E_{c_i}$ is minimum for M given collections of feature vectors, and wherein the total allowed eigenenergy and the expected risk exhibited by the M-class minimum risk linear classification system is minimum for the M given collections of feature vectors.

It follows that discriminant functions of M- class minimum risk linear classification systems that are determined by machine learning algorithms of the invention exhibit the minimum probability of error for classifying feature vectors that belong to M collections of feature vectors and unknown feature vectors related to the M collections of feature vectors.

It immediately follows that discriminant functions of minimum risk linear classification systems of the invention also provide scalable modules that are used to determine a fused discriminant function of a fused minimum risk linear classification system that classifies two types of feature vectors into two classes, wherein each type of feature vector has a different number of vector components. The total allowed eigenenergy and the minimum expected risk exhibited by the fused minimum risk linear classification system is determined by the total allowed eigenenergy and the minimum expected risk that is exhibited by an ensemble of a discriminant function of a minimum risk linear classification system sign(D(s)) and a different discriminant function of a different minimum risk linear classification system sign($\hat{D}$(s)):$\overline{E}_2$=sign(D(s))+sign($\hat{D}$(s)), wherein the total allowed eigenenergy and the expected risk exhibited by the fused minimum risk linear classification system is minimum for a given collection of feature vectors, wherein distributions of the feature vectors have similar covariance matrices, and a given collection of different feature vectors, wherein distributions of the different feature vectors have similar covariance matrices.

Any given fused discriminant function of a fused minimum risk linear classification system $\overline{E}_2$=sign(D(s))+sign($\hat{D}$(s)) that is determined by a machine learning algorithm of the invention exhibits the minimum probability of error for classifying feature vectors that belong to and are related to a collection of feature vectors, wherein distributions of the feature vectors have similar covariance matrices, as well as different feature vectors that belong to and are related to a collection of different feature vectors, wherein distributions of the different feature vectors have similar covariance matrices.

Discriminant functions of minimum risk linear classification systems of the invention also provide scalable modules that are used to determine a fused discriminant function of a fused M-class minimum risk linear classification system that classifies two types of feature vectors into M classes, wherein each type of feature vector has a different number of vector components, and wherein the total allowed eigenenergy and the minimum expected risk exhibited by the fused M-class minimum risk linear classification system is determined by the total allowed eigenenergy and the minimum expected risk that is exhibited by M ensembles of M−1 discriminant functions of M−1 minimum risk linear classification systems $E_M = \Sigma_{i=1}^{M} \Sigma_{j=1}^{M-1}$ sign($D_{ij}$(s)) and M different ensembles of M−1 different discriminant functions of M−1 different minimum risk linear classification systems $\hat{E}_M = \Sigma_{i=1}^{M} \Sigma_{j=1}^{M-1}$ sign($\hat{D}_{ij}$((s)):

$$\overline{E}_M = \Sigma_{i=1}^{M} \Sigma_{j=1}^{M-1} \text{sign}(D_{ij}(s)) + \Sigma_{i=1}^{M} \Sigma_{j=1}^{M-1} \text{sign}(\hat{D}_{ij}(s)),$$

wherein the total allowed eigenenergy and the expected risk exhibited by the fused M- class minimum risk linear classification system is minimum for M given collections of feature vectors and M given collections of different feature vectors, wherein distributions of feature vectors have similar covariance matrices for each minimum risk linear classification system sign($D_{ij}$(s)), and wherein distributions of different feature vectors have similar covariance matrices for each different minimum risk linear classification system sign($\hat{D}_{ij}$(s)).

Accordingly, fused discriminant functions of fused M-class minimum risk linear classification systems that are determined by machine learning algorithms of the invention exhibit the minimum probability of error for classifying feature vectors that belong to M collections of feature vectors and unknown feature vectors related to the M collections of feature vectors as well as different feature vectors that belong to M collections of different feature vectors and unknown different feature vectors related to the M collections of different feature vectors, wherein distributions of feature vectors have similar covariance matrices for each minimum risk linear classification system sign($D_{ij}$ (s)) and distributions of different feature vectors have similar covariance matrices for each different minimum risk linear classification system sign($\hat{D}_{ij}$(s)).

Further, given that discriminant functions of the invention determine likely locations of feature vectors that belong to given collections of feature vectors and any given unknown feature vectors related to a given collection, wherein a given collection of feature vectors belong to two classes, and given that discriminant functions of the invention identify decision regions related to two classes that given collections of feature vectors and any given unknown feature vectors related to a given collection are located within, and given that discriminant functions of the invention recognize classes of feature vectors that belong to given collections of feature vectors and any given unknown feature vectors related to a given collection, wherein minimum risk linear classification systems of the invention decide which of two classes that given collections of feature vectors and any given unknown feature vectors related to a given collection belong to, and thereby classify given collections of feature vectors and any given unknown feature vectors related to a given collection, it follows that discriminant functions of minimum risk linear classification systems of the invention can be used to determine a classification error rate and a measure of overlap between distributions of feature vectors for two classes of feature vectors, wherein distributions of the feature vectors have similar covariance matrices. Further, discriminant functions of minimum linear classification systems of the invention can be used to determine if distributions of two collections of feature vectors are homogenous distributions.

Embodiment 1

Figure 6:
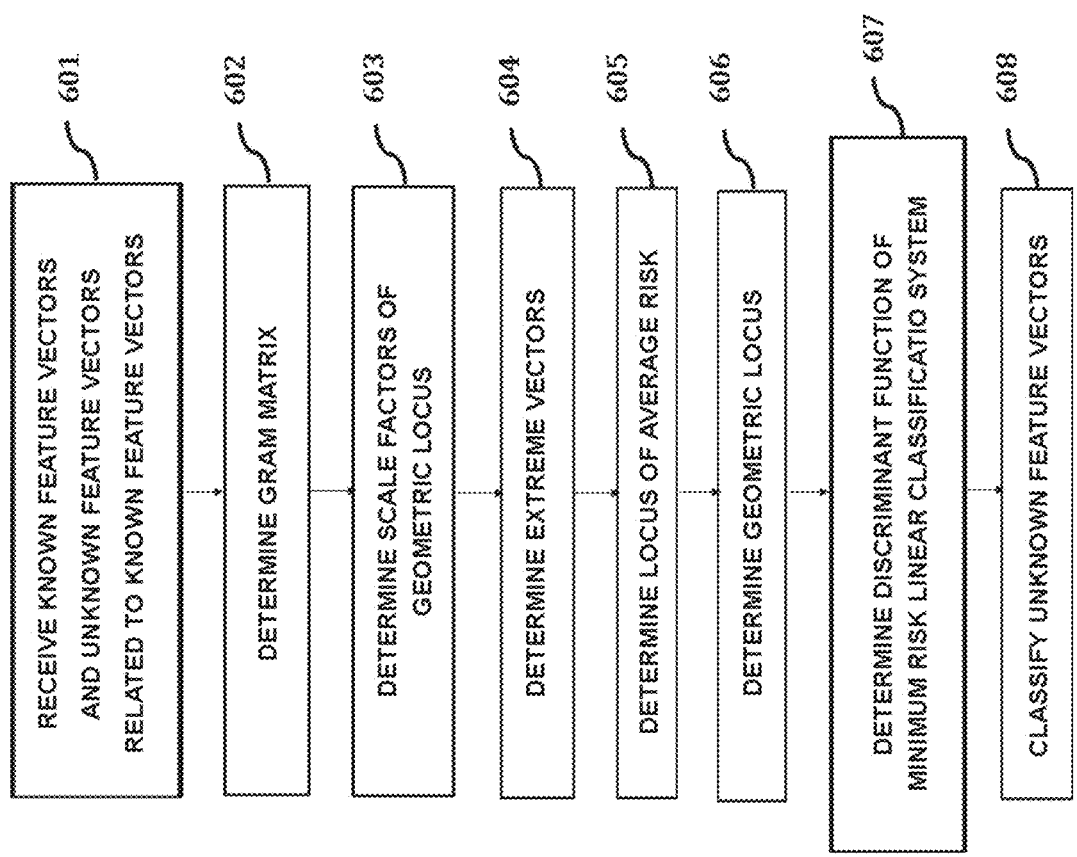
FIG. 6 is a flow diagram of programmed instructions executed by the processor of FIG. 11 to implement the method for determining a discriminant function of a minimum risk linear classification system that classifies feature vectors into two classes.

The method to determine a discriminant function of a minimum risk linear classification system that classifies feature vectors into two classes, designed in accordance with the invention, is fully described within the detailed description of the invention. FIG. 6 is a flow diagram of programmed instructions executed by the processor of FIG. 11 to implement the method for determining a discriminant function of a minimum risk linear classification system that classifies feature vectors into two classes. The process of determining the discriminant function of a minimum risk linear classification system comprises the following steps:

Receive an N×d data set of feature vectors within a computer system wherein N is the number of feature vectors, d is the number of vector components in each feature vector, and each one of the N feature vectors is labeled with information that identifies which of the two classes each one of the N feature vectors belongs to.

Receive unknown feature vectors related to the data set within the computer system.

Determine a Gram matrix using the data set by calculating a matrix of all possible inner products of the signed N feature vectors, wherein each one of the N feature vectors has a sign of +1 or 1 that identifies which of the two classes each one of the N feature vectors belongs to, and calculate a regularized Gram matrix from the Gram matrix.

Determine the scale factors of a geometric locus of signed and scaled extreme points by using the regularized Gram matrix to solve the dual optimization problem in Eq. (1.9).

Determine the extreme vectors on the geometric locus by identifying scale factors in the vector of scale factors that exceed zero by a small threshold T, e.g.: T=0.0050.

Determine a sign vector of the signs associated with the extreme vectors using the data set, and compute the average sign using the sign vector.

Determine a locus of average risk using the extreme vectors.

Determine the geometric locus by using the N feature vectors and the unknown feature vectors to calculate a matrix of inner products between the signed N feature vectors and the unknown feature vectors, and multiply the matrix by the vector of scale factors.

Determine the discriminant function of the minimum risk linear classification system, wherein the minimum risk linear classification system is determined by computing the sign of the discriminant function, and classify any given unknown feature vectors.

Embodiment 2

Figure 7:
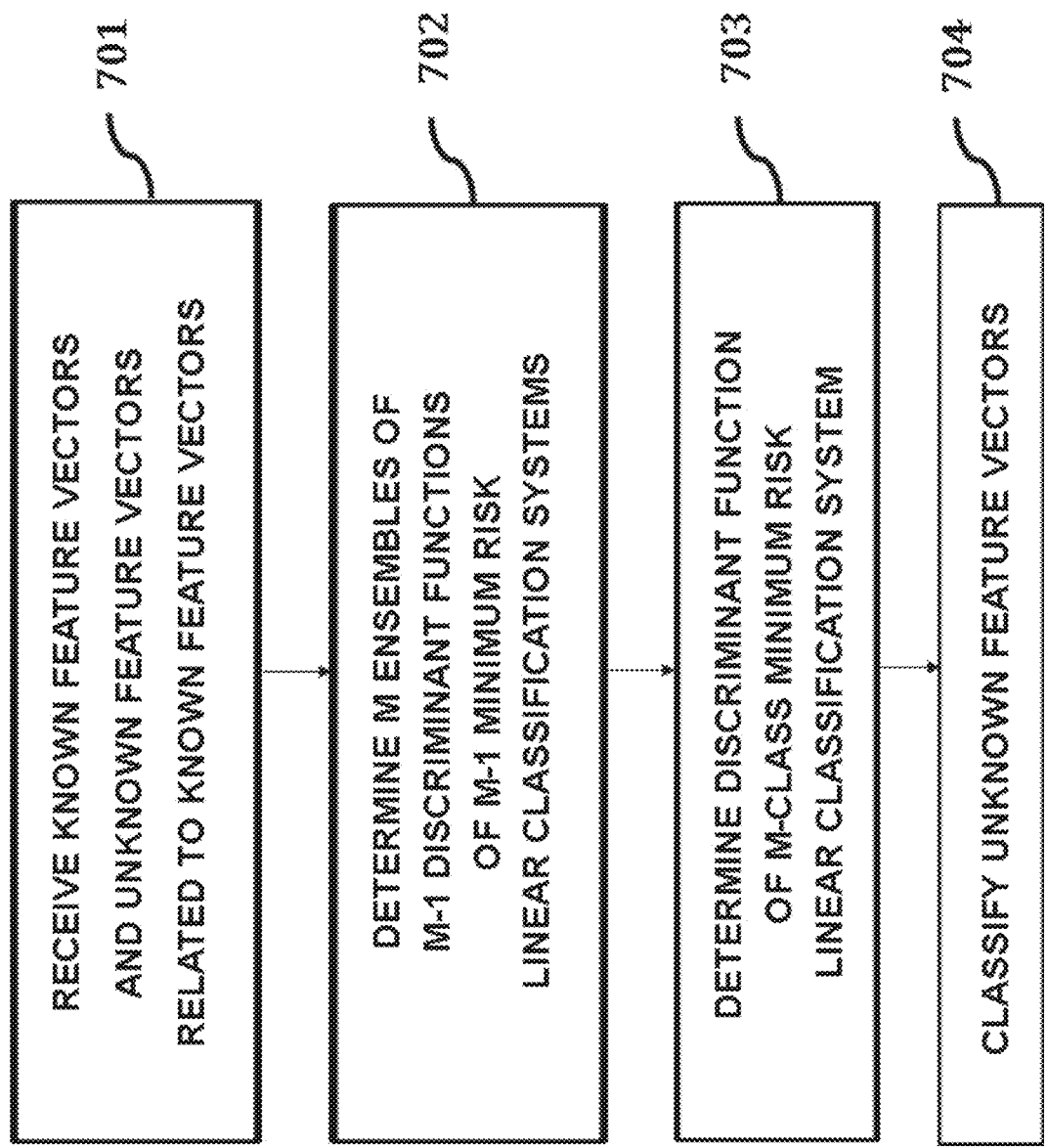
FIG. 7 is a flow diagram of programmed instructions executed by the processor of FIG. 11 to implement the method for determining a discriminant function of an M-class minimum risk linear classification system that classifies feature vectors into M classes.
Figure 11:
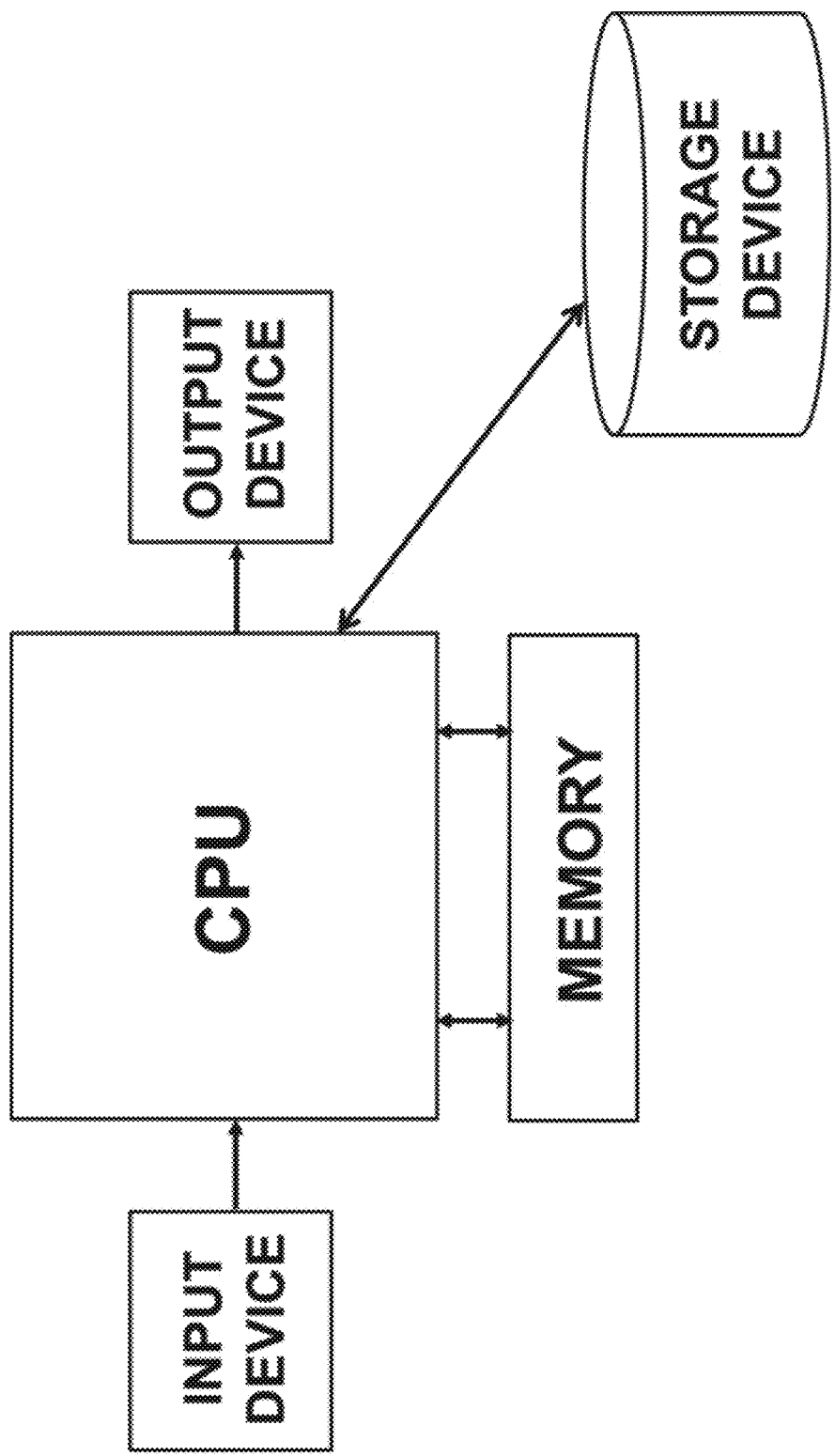
FIG. 11 illustrates hardware components that may be used to implement discriminant functions of minimum risk linear classification systems of the invention.

FIG. 7 is a flow diagram of programmed instructions executed by the processor of FIG. 11 to implement the method for determining a discriminant function of an M-class minimum risk linear classification system that classifies feature vectors into M classes.

A discriminant function of an M- class minimum risk linear classification system that classifies feature vectors into M classes is determined by using a machine learning algorithm of the invention and M collections of N feature vectors, wherein each feature vector in a given collection belongs to the same class, to determine M ensembles of M-1 discriminant functions of M-1 minimum risk linear classification systems, wherein the determination of each one of the M ensembles involves using the machine algorithm to determine M-1 discriminant functions of M-1 minimum risk linear classification systems for a class $c_i$ of feature vectors, wherein the N feature vectors that belong to the class $c_i$ have the sign +1 and all of the N feature vectors that belong to all of the other M-1 classes have the sign -1:

$$E_{c_i} = \Sigma_{j=1}^{M-1} \text{sign}(D_{ij}(s)),$$

wherein the input of the machine learning algorithm for each discriminant function of a minimum risk linear classification system $\text{sign}(D_{ij}(s))$ is the collection of N feature vectors that belongs to the class $c_i$ and a collection of N feature vectors that belongs to one of the other M-1 classes, and wherein the ensemble $E_{c_i}$ for class $c_i$ is determined by summing the M-1 discriminant functions of the M-1 minimum risk linear classification systems $E_{c_i} = \Sigma_{j=1}^{M-1} \text{sign}(D_{ij}(s))$, wherein the discriminant function $D_{ij}(s)$ discriminates between feature vectors that belong to class i and class j, and wherein the minimum risk linear classification system $\text{sign}(D_{ij}(s))$ decides which of the two classes i or j that a feature vector s belongs to: according to the sign of +1 or -1 that is output by the signum function $\text{sign}(D_{ij}(s))$, and wherein the output of the minimum risk linear classification system of the ensemble $E_{c_i}$ is determined by the sum:

$$\Sigma_{j=1}^{M-1} \text{sign}(D_{ij}(s)).$$

Therefore, the M ensembles of the M-1 discriminant functions of the M-1 minimum risk linear classification systems $$E_M = \Sigma_{i=1}^{M} \Sigma_{j=1}^{M-1} \text{sign}(D_{ij}(s))$$

determine the discriminant function of an M- class minimum risk linear classification system that classifies a feature vector s into the class $c_i$ associated with the ensemble $E_{c_i}$ that has the largest positive signed output, wherein each ensemble $E_{c_i}$ of M-1 discriminant functions of M-1 minimum risk linear classification systems for a given class $c_i$ of feature vectors exhibits the minimum probability of error for classifying the feature vectors that belong to the M collections of N feature vectors and unknown feature vectors related to the M collections, wherein distributions of the feature vectors have similar covariance matrices.

The discriminant function of the M-class minimum risk linear classification system $D_{E_M}(s)$ $$D_{E_M}(s) = \Sigma_{i=1}^{M} \Sigma_{j=1}^{M-1} \text{sign}(D_{ij}(s))$$

exhibits the minimum probability of error for classifying feature vectors that belong to the M collections of N feature vectors and unknown feature vectors related to the M collections of N feature vectors, wherein distributions of the feature vectors have similar covariance matrices, wherein the discriminant function of the M-class minimum risk linear classification system function determines likely locations of feature vectors that belong to and are related to the M collections of N feature vectors and identifies decision regions related to the M classes that the feature vectors are located within, wherein the discriminant function recognizes the classes of the feature vectors, and wherein the M- class minimum risk linear classification decides which of the M classes that the feature vectors belong to, and thereby classifies the feature vectors.

Embodiment 3

A fused discriminant function of a fused minimum risk linear classification system that classifies two types of feature vectors into two classes, wherein the types of feature vectors have different numbers of vector components, is determined by using a machine learning algorithm of the invention and a collection of N feature vectors and a collection of N different feature vectors to determine an ensemble of a discriminant function of a minimum risk linear classification system $\text{sign}(D(s))$ and a different discriminant function of a different minimum risk linear classification system $\text{sign}(\hat{D}(s))$: $\overline{E}_2 = \text{sign}(D(s)) + \text{sign}(\hat{D}(s))$, wherein the discriminant function and the different discriminant function are both determined by the process that is described in EMBODIMENT 1.

The fused discriminant function of the fused minimum risk linear classification system $$\overline{D}_{E_2}(s) = \text{sign}(D(s)) + \text{sign}(\hat{D}(s))$$

exhibits the minimum probability of error for classifying the feature vectors that belong to the collection of N feature vectors and unknown feature vectors related to the collection of N feature vectors, wherein distributions of the feature vectors have similar covariance matrices, as well as the different feature vectors that belong to the collection of N different feature vectors and unknown different feature vectors related to the collection of N different feature vectors, wherein distributions of the different feature vectors have similar covariance matrices, wherein the fused discriminant function determines likely locations of feature vectors that belong to and are related to the collection of N feature vectors as well as different feature vectors that belong to and are related to the collection of N different feature vectors and identifies decision regions related to the two classes that the feature vectors and the different feature vectors are located within, wherein the fused discriminant function recognizes the classes of the feature vectors and the different feature vectors, and wherein the fused minimum risk linear classification decides which of the two classes that the feature vectors and the different feature vectors belong to, and thereby classifies the feature vectors and the different feature vectors.

Embodiment 4

Figure 8:
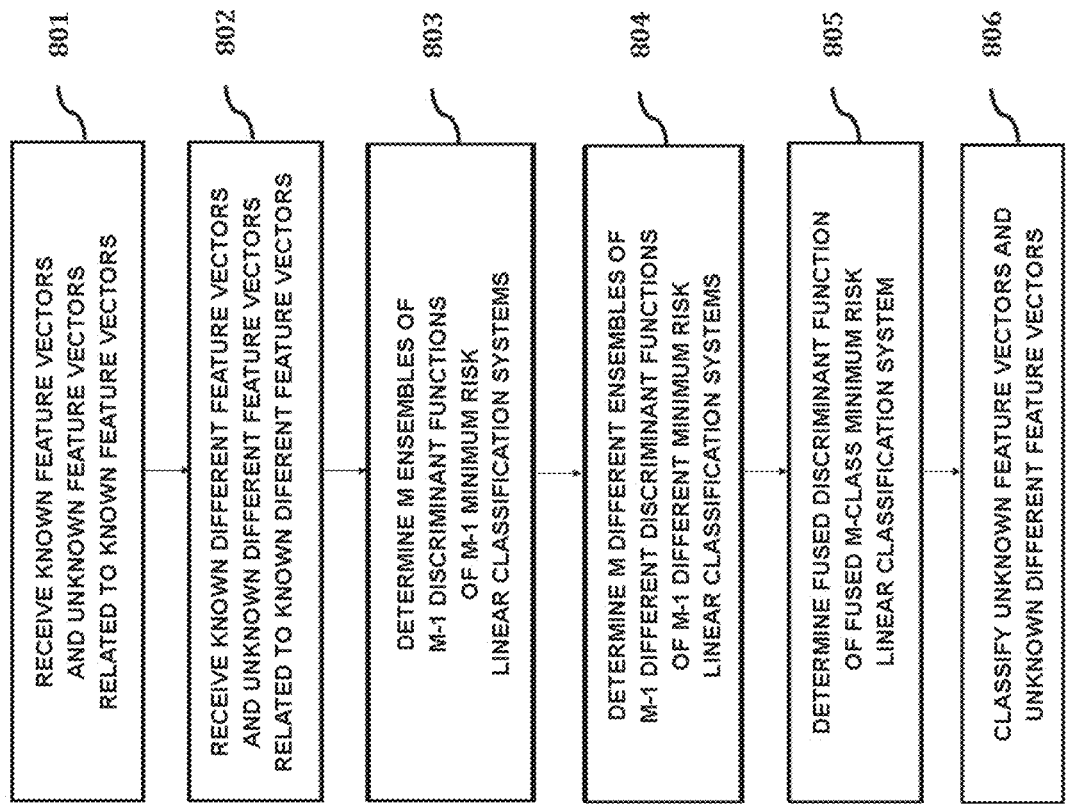
FIG. 8 is a flow diagram of programmed instructions executed by the processor of FIG. 11 to implement the method for determining a fused discriminant function of a fused M-class minimum risk linear classification system that classifies two types of feature vectors into M classes.

FIG. 8 is a flow diagram of programmed instructions executed by the processor of FIG. 11 to implement the method for determining a fused discriminant function of a fused M-class minimum risk linear classification system that classifies two types of feature vectors into M classes, wherein the types of feature vectors have different numbers of vector components.

A fused discriminant function of a fused M- class minimum risk linear classification system that classifies two types of feature vectors into M classes is determined by using a machine learning algorithm of the invention and M collections of N feature vectors to determine M ensembles of M-1 discriminant functions of M-1 minimum risk linear classification systems $E_M = \sum_{i=1}^{M} \sum_{j=1}^{M-1} \text{sign}(D_{ij}(s))$ as well as M collections of N different feature vectors to determine M different ensembles of M-1 different discriminant functions of M-1 different minimum risk linear classification systems $\hat{E}_M = \sum_{i=1}^{M} \sum_{j=1}^{M-1} \text{sign}(\hat{D}_{ij}(s))$, wherein the M ensembles and the M different ensembles are both determined by the process that is described in EMBODIMENT 2.

The fused discriminant function of the fused M- class minimum risk linear classification system $\overline{\overline{D}}_{E_M}(s)$ $$\overline{\overline{D}}_{E_M}(s) = E_M + \hat{E}_M = \sum_{i=1}^{M} \sum_{i=1}^{M-1} \text{sign}(D_{ij}(s)) + \sum_{i=1}^{M} \sum_{i=1}^{M-1} \text{sign}(\hat{D}_{ij}(s))$$

exhibits the minimum probability of error for classifying feature vectors that belong to the M collections of N feature vectors and unknown feature vectors related to the M collections of N feature vectors, wherein distributions of the feature vectors have similar covariance matrices, as well as different feature vectors that belong to the M collections of N different feature vectors and unknown different feature vectors related to the M collections of N different feature vectors, wherein distributions of the different feature vectors have similar covariance matrices, wherein the fused discriminant function determines likely locations of feature vectors that belong to and are related to the M collections of N feature vectors as well as different feature vectors that belong to and are related to the M collections of N different feature vectors and identifies decision regions related to the M classes that the feature vectors and the different feature vectors are located within, wherein the fused discriminant function recognizes the classes of the feature vectors and the different feature vectors, and wherein the fused M- class minimum risk linear classification decides which of the M classes that the feature vectors and the different feature vectors belong to, and thereby classifies the feature vectors and the different feature vectors.

Embodiment 5

Figure 9:
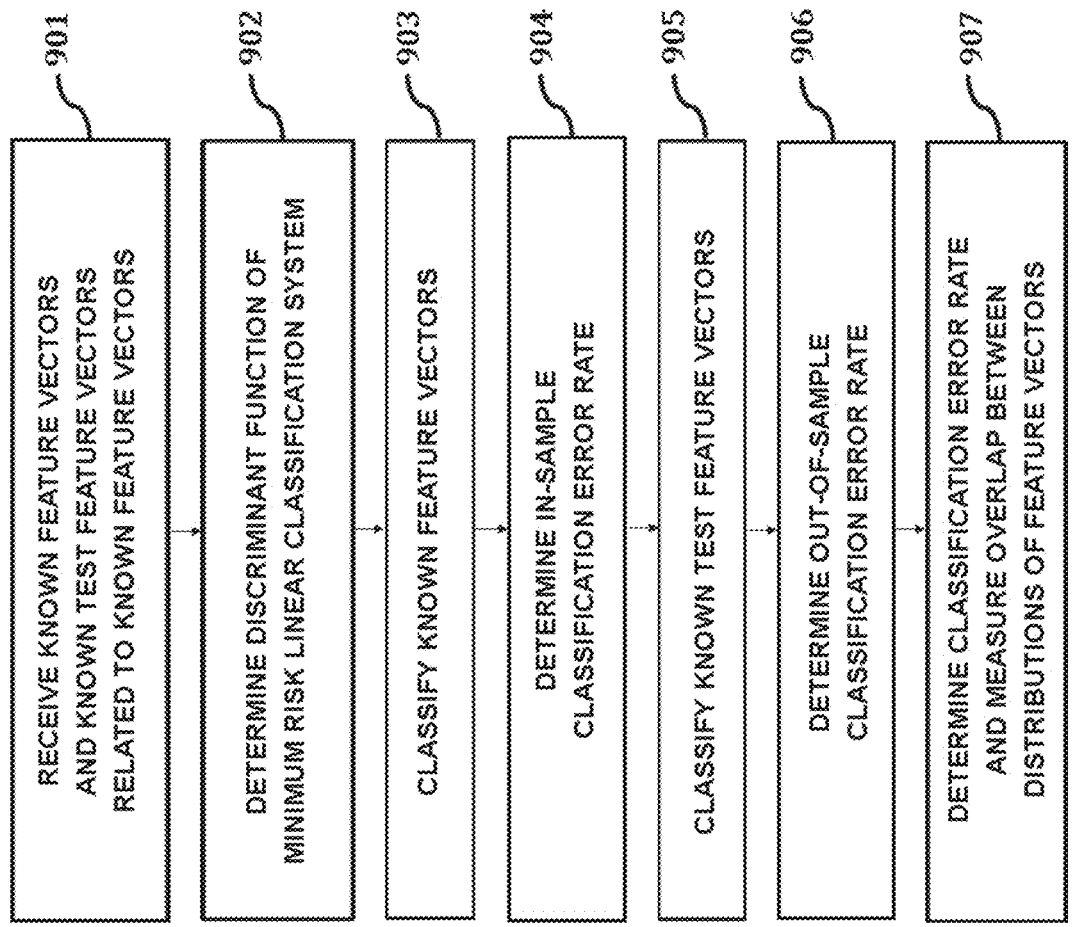
FIG. 9 is a flow diagram of programmed instructions executed by the processor of FIG. 11 to implement the method for using a discriminant function of a minimum risk linear classification system to determine a classification error rate and a measure of overlap between distributions of feature vectors for two classes of feature vectors.

FIG. 9 is a flow diagram of programmed instructions executed by the processor of FIG. 11 to implement the method for using a discriminant function of a minimum risk linear classification system to determine a classification error rate and a measure of overlap between distributions of feature vectors for two classes of feature vectors, wherein distributions of the feature vectors have similar covariance matrices.

The process of using a discriminant function of a minimum risk linear classification system to determine a classification error rate and a measure of overlap between distributions of feature vectors for two classes of feature vectors involves the following steps:

Receive an N×d data set of feature vectors within a computer system, wherein N is the number of feature vectors, d is the number of vector components in each feature vector, and each one of the N feature vectors is labeled with information that identifies which of the two classes each one of the N feature vectors belongs to.

Receive an N×d test data set of test feature vectors related to the data set within the computer system, wherein N is a number of test feature vectors, d is a number of vector components in each test feature vector, and each one of the N test feature vectors is labeled with information that identifies which of the two classes each one of the N test feature vectors belongs to.

Determine the discriminant function of the minimum risk linear classification system by performing the steps outlined in EMBODIMENT 1.

Use the minimum risk linear classification system to classify the N feature vectors.

Determine an in-sample classification error rate for the two classes of feature vectors by calculating the average number of wrong decisions of the minimum risk linear classification system for classifying the N features vectors.

Use the minimum risk linear classification system to classify the N test feature vectors.

Determine an out-of-sample classification error rate for the two classes of test feature vectors by calculating the average number of wrong decisions of the minimum risk linear classification system for classifying the N test feature vectors.

Determine the classification error rate for the two classes of feature vectors by averaging the in-sample classification error rate and the out-of-sample classification error rate.

Determine a measure of overlap between distributions of feature vectors for the two classes of feature vectors using the N feature vectors and the extreme vectors that have been identified, by calculating the ratio of the number of the extreme vectors to the number of the N feature vectors, wherein the ratio determines the measure of overlap.

Embodiment 6

Figure 10:
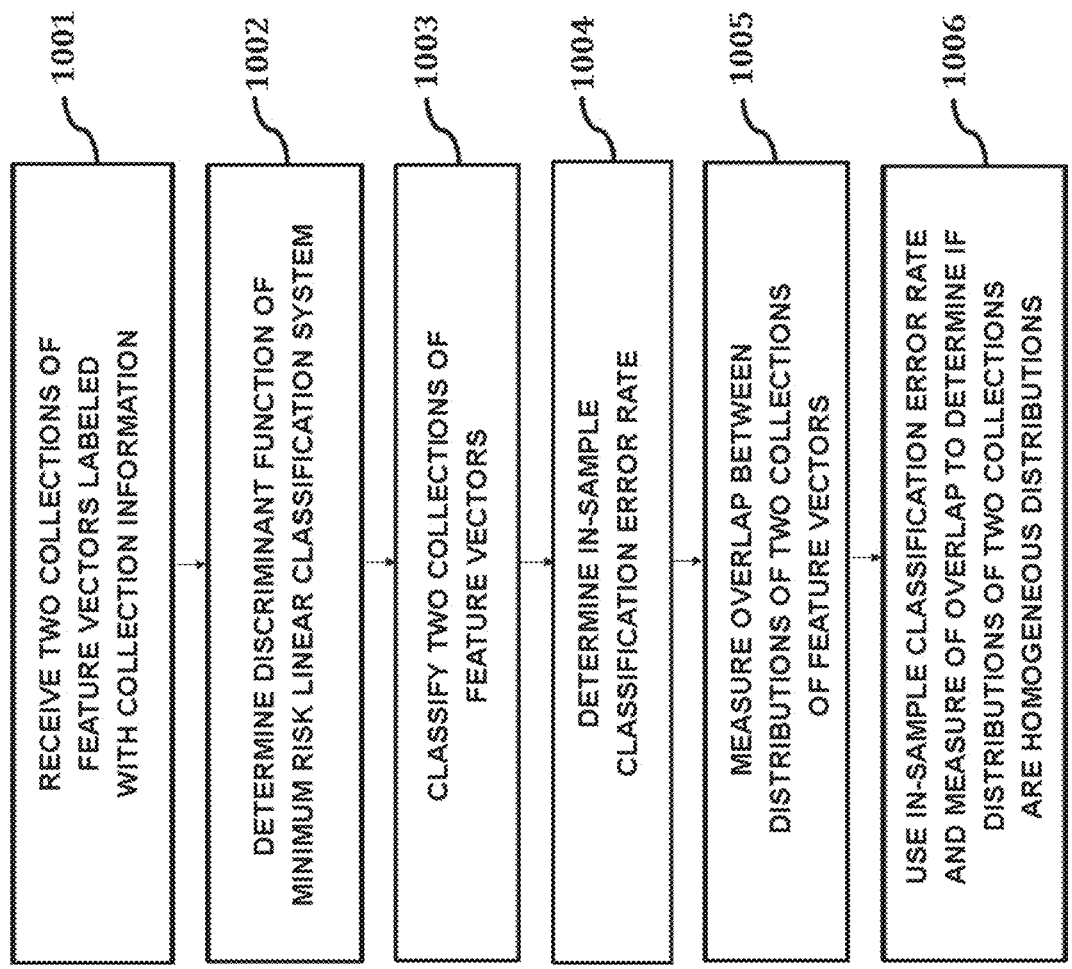
FIG. 10 is a flow diagram of programmed instructions executed by the processor of FIG. 11 to implement the method for using a discriminant function of a minimum risk linear classification system to determine if distributions of two collections of feature vectors are homogenous distributions.

FIG. 10 is a flow diagram of programmed instructions executed by the processor of FIG. 11 to implement the method for using a discriminant function of a minimum risk linear classification system to determine if distributions of two collections of feature vectors are homogenous distributions. The process of using a discriminant function of a minimum risk linear classification system to determine if distributions of two collections of feature vectors are homogenous distributions involves the following steps:

Receive an N×d data set of feature vectors within a computer system, wherein N is the number of feature vectors, d is the number of vector components in each feature vector, and each one of the N feature vectors is labeled with information that identifies which of the two collections each one of the N feature vectors belongs to.

Determine the discriminant function of the minimum risk linear classification system by performing the steps outlined in EMBODIMENT 1.

Use the minimum risk linear classification system to classify the N feature vectors.

Determine an in-sample classification error rate for the two collections of feature vectors by calculating the average number of wrong decisions of the minimum risk linear classification system for classifying the N features vectors.

Determine a measure of overlap between distributions of feature vectors for the two collections of feature vectors using the N feature vectors and the extreme vectors that have been identified, by calculating the ratio of the number of the extreme vectors to the number of the N feature vectors, wherein the ratio determines the measure of overlap.

Determine if the distributions of the two collections of the N feature vectors are homogenous distributions by using the in-sample classification error rate and the measure of overlap, wherein the distributions of the two collections of the N feature vectors are homogenous distributions if the measure of overlap has an approximate value of one and the in-sample classification error rate has an approximate value of one half.

Machine learning algorithms of the invention involve solving certain variants of the inequality constrained optimization that is used by support vector machines, wherein regularization parameters have been defined.

Software for machine learning algorithms of the invention can be obtained by using any of the software packages that solve quadratic programming problems, or via LIBSVM (A Library for Support Vector Machines), SVMlight (an implementation of SVMs in C) or MATLAB SVM toolboxes.

The machine learning methods of the invention disclosed herein may be readily utilized in a wide variety of applications, wherein feature vectors have been extracted from outputs of sensors that include, but are not limited to radar and hyperspectral or multispectral images, biometrics, digital communication signals, text, images, digital waveforms, etc.

More specifically, the applications include, for example and without limitation, general pattern recognition (including image recognition, waveform recognition, object detection, spectrum identification, and speech and handwriting recognition, data classification, (including text, image, and waveform categorization), bioinformatics (including automated diagnosis systems, biological modeling, and bio imaging classification), etc.

One skilled in the art will recognize that any suitable computer system may be used to execute the machine learning methods disclosed herein. The computer system may include, without limitation, a mainframe computer system, a workstation, a personal computer system, a personal digital assistant, or other device or apparatus having at least one processor that executes instructions from a memory medium.

The computer system may further include a display device or monitor for displaying operations associated with the learning machine and one or more memory mediums on which computer programs or software components may be stored. In addition, the memory medium may be entirely or partially located in one or more associated computers or computer systems which connect to the computer system over a network, such as the Internet.

The machine learning method described herein may also be executed in hardware, a combination of software and hardware, or in other suitable executable implementations. The learning machine methods implemented in software may be executed by the processor of the computer system or the processor or processors of the one or more associated computer systems connected to the computer system.

While the invention herein disclosed has been described by means of specific embodiments, numerous modifications and variations could be made by those skilled in the art without departing from the scope of the invention set forth in the claims.

What is claimed is:

1. A computer-implemented method of using feature vectors and machine learning algorithms to determine a discriminant function of a minimum risk linear classification system that classifies said feature vectors into two classes and using said discriminant function of said minimum risk linear classification system to classify unknown feature vectors related to said feature vectors, said method comprising:

receiving an N×d data set of feature vectors within a computer system, wherein N is a number of feature vectors, d is a number of vector components in each feature vector, and each one of said N feature vectors is labeled with information that identifies which of two classes each one of said N feature vectors belongs to, and wherein each said feature vector is defined by a d-dimensional vector of numerical features, wherein said numerical features are extracted from digital signals;

receiving within said computer system unknown feature vectors related to said data set;

determining a Gram matrix using said data set, said determination of said Gram matrix being performed by using processors of said computer system to calculate a matrix of all possible inner products of signed said N feature vectors, wherein each one of said N feature vectors has a sign of +1 or −1 that identifies which of said two classes each one of said N feature vectors belongs to, and using said processors of said computer system to calculate a regularized Gram matrix from said Gram matrix;

determining scale factors of a geometric locus of signed and scaled extreme points using said regularized Gram matrix, wherein said extreme points are located within overlapping regions or near tail regions of distributions of said N feature vectors, said determination of said scale factors being performed by using said processors of said computer system to determine a solution of a dual optimization problem, wherein said scale factors and said geometric locus satisfy a system of fundamental locus equations of binary classification, subject to geometric and statistical conditions for a minimum risk linear classification system in statistical equilibrium, and wherein said scale factors determine conditional densities for said extreme points and also determine critical minimum eigenenergies exhibited by scaled extreme vectors on said geometric locus, wherein said critical minimum eigenenergies determine conditional probabilities of said extreme points and also determine corresponding counter risks and risks of a minimum risk linear classification system, wherein said counter risks are associated with right decisions and said risks are associated with wrong decisions of said minimum risk linear classification system, and wherein said geometric locus determines the principal eigenaxis of the decision boundary of said minimum risk linear classification system, wherein said principal eigenaxis exhibits symmetrical dimensions and density, wherein said conditional probabilities and said critical minimum eigenenergies exhibited by said minimum risk linear classification system are symmetrically concentrated within said principal eigenaxis, and wherein counteracting and opposing components of said critical minimum eigenenergies exhibited by said scaled extreme vectors on said geometric locus together with said corresponding counter risks and risks exhibited by said minimum risk linear classification system are symmetrically balanced with each other about the geometric center of said principal eigenaxis, wherein the center of total allowed eigenenergy and minimum expected risk of said minimum risk linear classification system is located at the geometric center of said geometric locus, and wherein said geometric locus determines a primal representation of a dual locus of likelihood components and principal eigenaxis components, wherein said likelihood components and said principal eigenaxis components are symmetrically distributed over either side of the axis of said dual locus, wherein a statistical fulcrum is placed directly under the center of said dual locus, and wherein said likelihood components of said dual locus determine conditional likelihoods for said extreme points, and wherein said principal eigenaxis components of said dual locus determine an intrinsic coordinate system of geometric loci of a linear decision boundary and corresponding decision borders that jointly partition the decision space of said minimum risk linear classification system into symmetrical decision regions;

determining said extreme vectors on said geometric locus using the vector of said scale factors, said determination of said extreme vectors being performed by using said processors of said computer system to identify said scale factors that exceed zero by a small threshold, and using said processors of said computer system to determine a sign vector of signs associated with said extreme vectors using said data set, and compute the average sign using said sign vector;

determining a locus of average risk for said minimum risk linear classification system using said extreme vectors, said determination of said locus of average risk being performed by using said processors of said computer system to calculate the average vector of said extreme vectors;

determining said geometric locus, said determination of said geometric locus being performed by using said processors of said computer system to calculate a matrix of inner products between said signed said N feature vectors and said unknown feature vectors, and multiply said matrix by said vector of scale factors;

determining the discriminant function of said minimum risk linear classification system, using said locus of aggregate risk and said average sign and said geometric locus, said determination of said discriminant function of said minimum risk linear classification system being performed by using said processors of said computer system to subtract said locus of aggregate risk from sum of said geometric locus and said average sign, wherein said discriminant function of said minimum risk linear classification system satisfies said system of fundamental locus equations of binary classification, and wherein said discriminant function of said minimum risk linear classification system determines likely locations of said N feature vectors and also determines said geometric loci of said linear decision boundary and said corresponding decision borders that jointly partition said extreme points into said symmetrical decision regions, wherein said symmetrical decision regions span said overlapping regions or said tail regions of said distributions of said N feature vectors, and wherein said discriminant function of said minimum risk linear classification system satisfies said linear decision boundary in terms of a critical minimum eigenenergy and said minimum expected risk, wherein said counteracting and opposing components of said critical minimum eigenenergies exhibited by said scaled extreme vectors on said geometric locus associated with said corresponding counter risks and risks exhibited by said minimum risk linear classification system are symmetrically distributed over said axis of said dual locus, on equal sides of said statistical fulcrum located at said geometric center of said dual locus, wherein said counteracting and opposing components of said critical minimum eigenenergies together with said corresponding counter risks and risks exhibited by said minimum risk linear system are symmetrically balanced with each other about said geometric center of said dual locus, and wherein said statistical fulcrum is located at said center of said total allowed eigenenergy and said minimum expected risk of said minimum risk linear classification system, wherein said minimum risk linear classification system satisfies a state of statistical equilibrium, wherein said total allowed eigenenergy and said expected risk of said minimum risk linear classification system are minimized, and wherein said minimum risk linear classification system exhibits the minimum probability of error for classifying said N feature vectors that belong to said two classes and said unknown feature vectors related to said data set, wherein said distributions of said feature vectors have similar covariance matrices;

determining which of said two classes said unknown feature vectors belong to using said discriminant function of said minimum risk linear classification system, said determination of said classes of said unknown feature vectors being performed by using said processors of said computer system to apply said discriminant function of said minimum risk linear classification system to said unknown feature vectors, wherein said discriminant function determines likely locations of said unknown feature vectors and identifies said decision regions related to said two classes that said unknown feature vectors are located within, wherein said discriminant function recognizes said classes of said unknown feature vectors, and wherein said minimum risk linear classification system decides which of said two classes said unknown feature belong to and thereby classifies said unknown feature vectors.

2. A computer-implemented method of using feature vectors and machine learning algorithms to determine a fused discriminant function of a fused minimum risk linear classification system that classifies two types of said feature vectors into two classes, wherein said types of said feature vectors have different numbers of vector components, and using said fused discriminant function of said fused minimum risk linear classification system to classify unknown feature vectors related to said two types of said feature vectors, said method comprising:

receiving an N×d data set of feature vectors within a computer system, wherein N is a number of feature vectors, d is a number of vector components in each feature vector, and each one of said N feature vectors is labeled with information that identifies which of two classes each one of said N feature vectors belongs to, and wherein each said feature vector is defined by a d-dimensional vector of numerical features, wherein said numerical features are extracted from digital signals;

receiving an N×p different data set of different feature vectors within said computer system, wherein N is a number of different feature vectors, p is a number of vector components in each different feature vector, and each one of said N different feature vectors is labeled with information that identifies which of said two classes each one of said N different feature vectors belongs to, and wherein each said different feature vector is defined by a p-dimensional vector of numerical features, wherein said numerical features are extracted from digital signals;

receiving within said computer system unknown feature vectors related to said data set and unknown different feature vectors related to said different data set;

determining a Gram matrix using said data set, said determination of said Gram matrix being performed by using processors of said computer system to calculate a matrix of all possible inner products of signed said N feature vectors, wherein each one of said N feature vectors has a sign of +1 or −1 that identifies which of said two classes each one of said N feature vectors belongs to, and using said processors of said computer system to calculate a regularized Gram matrix from said Gram matrix;

determining a different Gram matrix using said different data set, said determination of said different Gram matrix being performed by using processors of said computer system to calculate a matrix of all possible inner products of signed said N different feature vectors, wherein each one of said N different feature vectors has a sign of +1 or −1 that identifies which of said two classes each one of said N different feature vectors belongs to, and using said processors of said computer system to calculate a regularized different Gram matrix from said different Gram matrix;

determining a discriminant function of a minimum risk linear classification system using said regularized Gram matrix and said data set, said determination of said discriminant function of said minimum risk linear classification system comprising the steps of:

determining scale factors of a geometric locus of signed and scaled extreme points using said regularized Gram matrix, wherein said extreme points are located within overlapping regions or near tail regions of distributions of said N feature vectors, said determination of said scale factors being performed by using said processors of said computer system to determine a solution of a dual optimization problem, wherein said scale factors and said geometric locus satisfy a system of fundamental locus equations of binary classification, subject to geometric and statistical conditions for a minimum risk linear classification system in statistical equilibrium, and wherein said scale factors determine conditional densities for said extreme points and also determine critical minimum eigenenergies exhibited by scaled extreme vectors on said geometric locus, wherein said critical minimum eigenenergies determine conditional probabilities of said extreme points and also determine corresponding counter risks and risks of a minimum risk linear classification system, wherein said counter risks are associated with right decisions and said risks are associated with wrong decisions of said minimum risk linear classification system, and wherein said geometric locus determines the principal eigenaxis of the decision boundary of said minimum risk linear classification system, wherein said principal eigenaxis exhibits symmetrical dimensions and density, wherein said conditional probabilities and said critical minimum eigenenergies exhibited by said minimum risk linear classification system are symmetrically concentrated within said principal eigenaxis, and wherein said counteracting and opposing components of said critical minimum eigenenergies exhibited by said scaled extreme vectors on said geometric locus together with said corresponding counter risks and risks exhibited by said minimum risk linear classification system are symmetrically balanced with each other about the geometric center of said principal eigenaxis, wherein the center of total allowed eigenenergy and minimum expected risk of said minimum risk linear classification system is located at the geometric center of said geometric locus, and wherein said geometric locus determines a primal representation of a dual locus of likelihood components and principal eigenaxis components, wherein said likelihood components and said principal eigenaxis components are symmetrically distributed over either side of the axis of said dual locus, wherein a statistical fulcrum is placed directly under the center of said dual locus, and wherein said likelihood components of said dual locus determine conditional likelihoods for said extreme points, and wherein said principal eigenaxis components of said dual locus determine an intrinsic coordinate system of geometric loci of a linear decision boundary and corresponding decision borders that jointly partition the decision space of said minimum risk linear classification system into symmetrical decision regions;

determining said extreme vectors on said geometric locus using the vector of said scale factors, said determination of said extreme vectors being performed by using said processors of said computer system to identify said scale factors that exceed zero by a small threshold, and using said processors of said computer system to determine a sign vector of signs associated with said extreme vectors using said data set, and compute the average sign using said sign vector;

determining a locus of average risk for said minimum risk linear classification system using said extreme vectors, said determination of said locus of average risk being performed by using said processors of said computer system to calculate the average vector of said extreme vectors;

determining said geometric locus, said determination of said geometric locus being performed by using said processors of said computer system to calculate a matrix of inner products between said signed said N feature vectors and said unknown feature vectors, and multiply said matrix by said vector of scale factors;

determining the discriminant function of said minimum risk linear classification system, using said locus of aggregate risk and said average sign and said geometric locus, said determination of said discriminant function of said minimum risk linear classification system being performed by using said processors of said computer system to subtract said locus of aggregate risk from sum of said geometric locus and said average sign, wherein said discriminant function of said minimum risk linear classification system satisfies said system of fundamental locus equations of binary classification, and wherein said discriminant function of said minimum risk linear classification system determines likely locations of said N feature vectors and also determines said geometric loci of said linear decision boundary and said corresponding decision borders that jointly partition said extreme points into said symmetrical decision regions, wherein said symmetrical decision regions span said overlapping regions or said tail regions of said distributions of said N feature vectors, and wherein said discriminant function of said minimum risk linear classification system satisfies said linear decision boundary in terms of a critical minimum eigenenergy and said minimum expected risk, wherein said counteracting and opposing components of said critical minimum eigenenergies exhibited by said scaled extreme vectors on said geometric locus associated with said corresponding counter risks and risks exhibited by said minimum risk linear classification system are symmetrically distributed over said axis of said dual locus, on equal sides of said statistical fulcrum located at said geometric center of said dual locus, wherein said counteracting and opposing components of said critical minimum eigenenergies together with said corresponding counter risks and risks exhibited by said minimum risk linear system are symmetrically balanced with each other about said geometric center of said dual locus, and wherein said statistical fulcrum is located at said center of said total allowed eigenenergy and said minimum expected risk of said minimum risk linear classification system, wherein said minimum risk linear classification system satisfies a state of statistical equilibrium, wherein said total allowed eigenenergy and said expected risk of said minimum risk linear classification system are minimized, and wherein said minimum risk linear classification system exhibits the minimum probability of error for classifying said N feature vectors that belong to said two classes and said unknown feature vectors related to said data set, wherein said distributions of said feature vectors have similar covariance matrices;

determining a different discriminant function of a different minimum risk linear classification system using said regularized different Gram matrix and said different data set, said determination of said different discriminant function of said different minimum risk linear classification system being performed by using said processors of said computer system to perform said steps of determining said discriminant function of said minimum risk linear classification system, wherein said different minimum risk linear classification system exhibits the minimum probability of error for classifying said N different feature vectors that belong to said two classes and said unknown different feature vectors related to said different data set, wherein distributions of said different feature vectors have similar covariance matrices;

determining a fused discriminant function of a fused minimum risk linear classification system using said discriminant function of said minimum risk linear classification system and said different discriminant function of said different minimum risk linear classification system, said determination of said fused discriminant function of said fused minimum risk linear classification system being performed by using said processors of said computer system to sum said discriminant function of said minimum risk linear classification system and said different discriminant function of said different minimum risk linear classification system; and determining which of said two classes said unknown feature vectors and said unknown different feature vectors belong to using said fused discriminant function of said fused minimum risk linear classification system, said determination of said classes of said unknown feature vectors and said unknown different feature vectors being performed by using said processors of said computer system to apply said fused discriminant function of said fused minimum risk linear classification system to said unknown feature vectors and said unknown different feature vectors, wherein said fused discriminant function determines likely locations of said unknown feature vectors and said unknown different feature vectors and identifies said decision regions related to said two classes that said unknown feature vectors and said unknown different feature vectors are located within, wherein said fused discriminant function recognizes said classes of said unknown feature vectors and said unknown different feature vectors, and wherein said fused minimum risk linear classification system decides which of said two classes said unknown feature vectors and said unknown different feature vectors belong to and thereby classifies said unknown feature vectors and said unknown different feature.

3. A computer-implemented method of using feature vectors and machine learning algorithms to determine a discriminant function of an M-class minimum risk linear classification system that classifies said feature vectors into M classes and using said discriminant function of said M-class minimum risk linear classification system to classify unknown feature vectors related to said feature vectors, said method comprising:

receiving M N×d data sets of feature vectors within a computer system, wherein M is a number of classes, N is a number of feature vectors in each one of said M data sets, d is a number of vector components in each feature vector, and each one of said N feature vectors in each one of said M data sets belongs to the same class and is labeled with information that identifies said class, and wherein each said feature vector is defined by a d-dimensional vector of numerical features, wherein said numerical features are extracted from digital signals;

receiving within said computer system unknown feature vectors related to said M data sets;

determining M ensembles of M−1 discriminant functions of M−1 minimum risk linear classification systems using said M data sets, wherein the determination of each one of said M ensembles comprises the steps of:

determining M−1 Gram matrices for a class of feature vectors using said M data sets, said determination of said M−1 Gram matrices being performed by using processors of said computer system to calculate M−1 matrices, wherein each matrix contains all possible inner products of signed feature vectors that belong to said class and one of the other M−1 classes, wherein said N feature vectors that belong to said class have the sign +1, and said N feature vectors that belong to said other class have the sign −1, and wherein said M−1 matrices account for all of the other said M−1 classes, and calculating M−1 regularized Gram matrices from said M−1 Gram matrices;

determining M−1 discriminant functions of M−1 minimum risk linear classification systems using said M−1 regularized Gram matrices, wherein the determination of each one of said M−1 discriminant functions of M−1 minimum risk linear classification systems further comprises the steps of:

determining scale factors of a geometric locus of signed and scaled extreme points using one of said regularized Gram matrices, wherein said extreme points are located within overlapping regions or near tail regions of distributions of feature vectors that belong to said class and one of the other said M–1 classes, said determination of said scale factors being performed by using said processors of said computer system to determine a solution of a dual optimization problem, wherein said scale factors and said geometric locus satisfy a system of fundamental locus equations of binary classification, subject to geometric and statistical conditions for a minimum risk linear classification system in statistical equilibrium, and wherein said scale factors determine conditional densities for said extreme points and also determine critical minimum eigenenergies exhibited by scaled extreme vectors on said geometric locus, wherein said critical minimum eigenenergies determine conditional probabilities of said extreme points and also determine corresponding counter risks and risks of a minimum risk linear classification system, wherein said counter risks are associated with right decisions and said risks are associated with wrong decisions of said minimum risk linear classification system, and wherein said geometric locus determines the principal eigenaxis of the decision boundary of said minimum risk linear classification system, wherein said principal eigenaxis exhibits symmetrical dimensions and density, wherein said conditional probabilities and said critical minimum eigenenergies exhibited by said minimum risk linear classification system are symmetrically concentrated within said principal eigenaxis, and wherein counteracting and opposing components of said critical minimum eigenenergies exhibited by said scaled extreme vectors on said geometric locus together with said corresponding counter risks and risks exhibited by said minimum risk linear classification system are symmetrically balanced with each other about the geometric center of said principal eigenaxis, wherein the center of total allowed eigenenergy and minimum expected risk of said minimum risk linear classification system is located at the geometric center of said geometric locus, and wherein said geometric locus determines a primal representation of a dual locus of likelihood components and principal eigenaxis components, wherein said likelihood components and said principal eigenaxis components are symmetrically distributed over either side of the axis of said dual locus, wherein a statistical fulcrum is placed directly under the center of said dual locus, and wherein said likelihood components of said dual locus determine conditional likelihoods for said extreme points, and wherein said principal eigenaxis components of said dual locus determine an intrinsic coordinate system of geometric loci of a linear decision boundary and corresponding decision borders that jointly partition the decision space of said minimum risk linear classification system into symmetrical decision regions;

determining said extreme vectors on said geometric locus using the vector of said scale factors, said determination of said extreme vectors being performed by using said processors of said computer system to identify said scale factors that exceed zero by a small threshold, and using said processors of said computer system to determine a sign vector of signs associated with said extreme vectors using said data set, and compute the average sign using said sign vector;

determining a locus of average risk for said minimum risk linear classification system using said extreme vectors, said determination of said locus of average risk being performed by using said processors of said computer system to calculate the average vector of said extreme vectors;

determining said geometric locus, said determination of said geometric locus being performed by using said processors of said computer system to calculate a matrix of inner products between said signed said feature vectors that belong to said class and said other class and said unknown feature vectors, and multiply said matrix by said vector of scale factors;

determining the discriminant function of said minimum linear classification system, using said locus of average risk and said average sign and said geometric locus, said determination of said discriminant function of said minimum risk linear classification system being performed by using said processors of said computer system to subtract said locus of average risk from sum of said geometric locus and said average sign, wherein said discriminant function of said minimum risk linear classification system satisfies said system of fundamental locus equations of binary classification, and wherein said discriminant function of said minimum risk linear classification system determines likely locations of said N feature vectors from said class and said N feature vectors from said other class and also determines said geometric loci of said linear decision boundary and said corresponding decision borders that jointly partition said extreme points into said symmetrical decision regions, wherein said symmetrical decision regions span said overlapping regions or said tail regions of said distributions of said N feature vectors that belong to said class and said N feature vectors that belong to said other class, and wherein said discriminant function of said minimum risk linear classification system satisfies said linear decision boundary in terms of a critical minimum eigenenergy and said minimum expected risk, wherein said counteracting and opposing components of said critical minimum eigenenergies exhibited by said scaled extreme vectors on said geometric locus associated with said corresponding counter risks and risks exhibited by said minimum risk linear classification system are symmetrically distributed over said axis of said dual locus, on equal sides of said statistical fulcrum located at said geometric center of said dual locus, wherein said counteracting and opposing components of said critical minimum eigenenergies together with said corresponding counter risks and risks exhibited by said minimum risk linear system are symmetrically balanced with each other about said geometric center of said dual locus, and wherein said statistical fulcrum is located at said center of said total allowed eigenenergy and said minimum expected risk of said minimum risk linear classification system, wherein said minimum risk linear classification system satisfies a state of statistical equilibrium, wherein said total allowed eigenenergy and said expected risk of said minimum risk linear classification system are minimized, and wherein said minimum risk linear classification system exhibits the minimum probability of error for classifying said N feature vectors that belong to said class and said N feature vectors that belong to said other class and said unknown feature vectors related to said data set and said other data set, wherein said distributions of said feature vectors have similar covariance matrices;

determining a discriminant function of an M-class minimum risk linear classification system using said M ensembles of M−1 discriminant functions of M−1 minimum risk linear classification systems, said determination of said discriminant function of said M-class minimum risk linear classification system being performed by using said processors of said computer system to sum said M ensembles of M−1 discriminant functions of M−1 minimum risk linear classification systems;

determining which of said M classes said unknown feature vectors belong to using said discriminant function of said M-class minimum risk linear classification system, said determination of said classes of said unknown feature vectors being performed by using said processors of said computer system to apply said discriminant function of said M-class minimum risk linear classification system to said unknown feature vectors, wherein said discriminant function determines likely locations of said unknown feature vectors and identifies said decision regions related to said M classes that said unknown feature vectors are located within, wherein said discriminant function recognizes said classes of said unknown feature vectors, and wherein said M-class minimum risk linear classification system decides which of said M classes said unknown feature vectors belong to and thereby classifies said unknown feature vectors.

4. A computer-implemented method of using feature vectors and machine learning algorithms to determine a fused discriminant function of a fused M-class minimum risk linear classification system that classifies two types of said feature vectors into M classes, wherein said types of said feature vectors have different numbers of vector components, and using said fused discriminant function of said fused M-class minimum risk linear classification system to classify unknown feature vectors related to said two types of said feature vectors, said method comprising:

receiving M N×d data sets of feature vectors within a computer system, wherein M is a number of classes, N is a number of feature vectors in each one of said M data sets, d is a number of vector components in each feature vector, and each one of said N feature vectors in each one of said M data sets belongs to the same class and is labeled with information that identifies said class, and wherein each said feature vector is defined by a d-dimensional vector of numerical features, wherein said numerical features are extracted from digital signals;

receiving M N×p different data sets of different feature vectors within said computer system, wherein M is said number of said classes, N is a number of different feature vectors in each one of said M different data sets, p is a number of vector components in each different feature vector, and each one of said N different feature vectors in each one of said M different data sets belongs to the same class and is labeled with information that identifies said class, and wherein each said different feature vector is defined by a p-dimensional vector of numerical features, wherein said numerical features are extracted from digital signals;

receiving within said computer system unknown feature vectors related to said M data sets and unknown different feature vectors related to said M different data sets;

determining M ensembles of M−1 discriminant functions of M−1 minimum risk linear classification systems using said M data sets, wherein the determination of each one of said M ensembles comprises the steps of:

determining M−1 Gram matrices for a class of feature vectors using said M data sets, said determination of said M−1 Gram matrices being performed by using processors of said computer system to calculate M−1 matrices, wherein each matrix contains all possible inner products of signed feature vectors that belong to said class and one of the other M−1 classes, wherein said N feature vectors that belong to said class have the sign +1, and said N feature vectors that belong to said other class have the sign −1, and wherein said M−1 matrices account for all of the other said M−1 classes, and calculating M−1 regularized Gram matrices from said M−1 Gram matrices;

determining M−1 discriminant functions of M−1 minimum risk linear classification systems using said M−1 regularized Gram matrices, wherein the determination of each one of said M−1 discriminant functions of M−1 minimum risk linear classification systems further comprises the steps of:

determining scale factors of a geometric locus of signed and scaled extreme points using one of said regularized Gram matrices, wherein said extreme points are located within overlapping regions or near tail regions of distributions of feature vectors that belong to said class and one of the other said M−1 classes, said determination of said scale factors being performed by using said processors of said computer system to determine a solution of a dual optimization problem, wherein said scale factors and said geometric locus satisfy a system of fundamental locus equations of binary classification, subject to geometric and statistical conditions for a minimum risk linear classification system in statistical equilibrium, and wherein said scale factors determine conditional densities for said extreme points and also determine critical minimum eigenenergies exhibited by scaled extreme vectors on said geometric locus, wherein said critical minimum eigenenergies determine conditional probabilities of said extreme points and also determine corresponding counter risks and risks of a minimum risk linear classification system, wherein said counter risks are associated with right decisions and said risks are associated with wrong decisions of said minimum risk linear classification system, and wherein said geometric locus determines the principal eigenaxis of the decision boundary of said minimum risk linear classification system, wherein said principal eigenaxis exhibits symmetrical dimensions and density, wherein said conditional probabilities and said critical minimum eigenenergies exhibited by said minimum risk linear classification system are symmetrically concentrated within said principal eigenaxis, and wherein counteracting and opposing components of said critical minimum eigenenergies exhibited by said scaled extreme vectors on said geometric locus together with said corresponding counter risks and risks exhibited by said minimum risk linear classification system are symmetrically balanced with each other about the geometric center of said principal eigenaxis, wherein the center of total allowed eigenenergy and minimum expected risk of said minimum risk linear classification system is located at the geometric center of said geometric locus, and wherein said geometric locus determines a primal representation of a dual locus of likelihood components and principal eigenaxis components, wherein said likelihood components and said principal eigenaxis components are symmetrically distributed over either side of the axis of said dual locus, wherein a statistical fulcrum is placed directly under the center of said dual locus, and wherein said likelihood components of said dual locus determine conditional likelihoods for said extreme points, and wherein said principal eigenaxis components of said dual locus determine an intrinsic coordinate system of geometric loci of a linear decision boundary and corresponding decision borders that jointly partition the decision space of said minimum risk linear classification system into symmetrical decision regions;

determining said extreme vectors on said geometric locus using the vector of said scale factors, said determination of said extreme vectors being performed by using said processors of said computer system to identify said scale factors that exceed zero by a small threshold, and using said processors of said computer system to determine a sign vector of signs associated with said extreme vectors using said data set, and compute the average sign using said sign vector;

determining a locus of average risk for said minimum risk linear classification system using said extreme vectors, said determination of said locus of average risk being performed by using said processors of said computer system to calculate the average vector of said extreme vectors;

determining said geometric locus, said determination of said geometric locus being performed by using said processors of said computer system to calculate a matrix of inner products between said signed said feature vectors that belong to said class and said other class and said unknown feature vectors, and multiply said matrix by said vector of scale factors;

determining the discriminant function of said minimum linear classification system, using said locus of average risk and said average sign and said geometric locus, said determination of said discriminant function of said minimum risk linear classification system being performed by using said processors of said computer system to subtract said locus of average risk from sum of said geometric locus and said average sign, wherein said discriminant function of said minimum risk linear classification system satisfies said system of fundamental locus equations of binary classification, and wherein said discriminant function of said minimum risk linear classification system determines likely locations of said N feature vectors from said class and said N feature vectors from said other class and also determines said geometric loci of said linear decision boundary and said corresponding decision borders that jointly partition said extreme points into said symmetrical decision regions, wherein said symmetrical decision regions span said overlapping regions or said tail regions of said distributions of said N feature vectors that belong to said class and said N feature vectors that belong to said other class, and wherein said discriminant function of said minimum risk linear classification system satisfies said linear decision boundary in terms of a critical minimum eigenenergy and said minimum expected risk, wherein said counteracting and opposing components of said critical minimum eigenenergies exhibited by said scaled extreme vectors on said geometric locus associated with said corresponding counter risks and risks exhibited by said minimum risk linear classification system are symmetrically distributed over said axis of said dual locus, on equal sides of said statistical fulcrum located at said geometric center of said dual locus, wherein said counteracting and opposing components of said critical minimum eigenenergies together with said corresponding counter risks and risks exhibited by said minimum risk linear system are symmetrically balanced with each other about said geometric center of said dual locus, and wherein said statistical fulcrum is located at said center of said total allowed eigenenergy and said minimum expected risk of said minimum risk linear classification system, wherein said minimum risk linear classification system satisfies a state of statistical equilibrium, wherein said total allowed eigenenergy and said expected risk of said minimum risk linear classification system are minimized, and wherein said minimum risk linear classification system exhibits the minimum probability of error for classifying said N feature vectors that belong to said class and said N feature vectors that belong to said other class and said unknown feature vectors related to said data set and said other data set, wherein said distributions of said feature vectors have similar covariance matrices;

determining M different ensembles of M−1 different discriminant functions of M−1 different minimum risk linear classification systems using said M different data sets, said determination of said M different ensembles of M−1 different discriminant functions of M−1 different minimum risk linear classification systems being performed by performing said steps of determining M ensembles of M−1 discriminant functions of M−1 minimum risk linear classification systems;

determining a fused discriminant function of a fused M-class minimum risk linear classification system using said M ensembles of M−1 discriminant functions of M−1 minimum risk linear classification systems and said M different ensembles of M−1 different discriminant functions of M−1 different minimum risk linear classification systems, said determination of said fused discriminant function of said fused M-class minimum risk linear classification system being performed by using said processors of said computer system to sum said M ensembles of M−1 discriminant functions of M−1 minimum risk linear classification systems and said M different ensembles of M−1 different discriminant functions of M−1 different minimum risk linear classification systems;

determining which of said M classes said unknown feature vectors and said unknown different feature vectors belong to using said fused discriminant function of said fused M-class minimum risk linear classification system, said determination of said classes of said unknown feature vectors and said unknown different feature vectors being performed by using said processors of said computer system to apply said fused discriminant function of said fused M-class minimum risk linear classification system to said unknown feature vectors and said unknown different feature vectors, wherein said fused discriminant function determines likely locations of said unknown feature vectors and said unknown different feature vectors and identifies said decision regions related to said M classes that said unknown feature vectors and said unknown different feature vectors are located within, wherein said fused discriminant function recognizes said classes of said unknown feature vectors and said unknown different feature vectors, and wherein said fused M-class minimum risk linear classification system decides which of said M classes said unknown feature vectors and said unknown different feature vectors belong to and thereby classifies said unknown feature vectors and said unknown different feature vectors.

5. A computer-implemented method of using feature vectors and machine learning algorithms to determine a discriminant function of a minimum risk linear classification system that classifies said feature vectors into two classes and using said discriminant function of said minimum risk linear classification system to determine a classification error rate and a measure of overlap between distributions of said feature vectors, said method comprising:

receiving an N×d data set of feature vectors within a computer system, wherein N is a number of feature vectors, d is a number of vector components in each feature vector, and each one of said N feature vectors is labeled with information that identifies which of two classes each one of said N feature vectors belongs to, and wherein each said feature vector is defined by a d-dimensional vector of numerical features, wherein said numerical features are extracted from digital signals;

receiving an N×d test data set of test feature vectors related to said data set within said computer system, wherein N is a number of test feature vectors, d is a number of vector components in each test feature vector, and each one of said N test feature vectors is labeled with information that identifies which of said two classes each one of said N test feature vectors belongs to;

determining a Gram matrix using said data set, said determination of said Gram matrix being performed by using processors of said computer system to calculate a matrix of all possible inner products of signed said N feature vectors, wherein each one of said N feature vectors has a sign of +1 or −1 that identifies which of said two classes each one of said N feature vectors belongs to, and using said processors of said computer system to calculate a regularized Gram matrix from said Gram matrix;

determining scale factors of a geometric locus of signed and scaled extreme points using said regularized Gram matrix, wherein said extreme points are located within overlapping regions or near tail regions of distributions of said N feature vectors, said determination of said scale factors being performed by using said processors of said computer system to determine a solution of a dual optimization problem, wherein said scale factors and said geometric locus satisfy a system of fundamental locus equations of binary classification, subject to geometric and statistical conditions for a minimum risk linear classification system in statistical equilibrium, and wherein said scale factors determine conditional densities for said extreme points and also determine critical minimum eigenenergies exhibited by scaled extreme vectors on said geometric locus, wherein said critical minimum eigenenergies determine conditional probabilities of said extreme points and also determine corresponding counter risks and risks of a minimum risk linear classification system, wherein said counter risks are associated with right decisions and said risks are associated with wrong decisions of said minimum risk linear classification system, and wherein said geometric locus determines the principal eigenaxis of the decision boundary of said minimum risk linear classification system, wherein said principal eigenaxis exhibits symmetrical dimensions and density, wherein said conditional probabilities and said critical minimum eigenenergies exhibited by said minimum risk linear classification system are symmetrically concentrated within said principal eigenaxis, and wherein counteracting and opposing components of said critical minimum eigenenergies exhibited by said scaled extreme vectors on said geometric locus together with said corresponding counter risks and risks exhibited by said minimum risk linear classification system are symmetrically balanced with each other about the geometric center of said principal eigenaxis, wherein the center of total allowed eigenenergy and minimum expected risk of said minimum risk linear classification system is located at the geometric center of said geometric locus, and wherein said geometric locus determines a primal representation of a dual locus of likelihood components and principal eigenaxis components, wherein said likelihood components and said principal eigenaxis components are symmetrically distributed over either side of the axis of said dual locus, wherein a statistical fulcrum is placed directly under the center of said dual locus, and wherein said likelihood components of said dual locus determine conditional likelihoods for said extreme points, and wherein said principal eigenaxis components of said dual locus determine an intrinsic coordinate system of geometric loci of a linear decision boundary and corresponding decision borders that jointly partition the decision space of said minimum risk linear classification system into symmetrical decision regions;

determining said extreme vectors on said geometric locus using the vector of said scale factors, said determination of said extreme vectors being performed by using said processors of said computer system to identify said scale factors that exceed zero by a small threshold, and using said processors of said computer system to determine a sign vector of signs associated with said extreme vectors using said data set, and compute the average sign using said sign vector;

determining a locus of average risk for said minimum risk linear classification system using said extreme vectors, said determination of said locus of average risk being performed by using said processors of said computer system to calculate the average vector of said extreme vectors;

determining said geometric locus, said determination of said geometric locus being performed by using said processors of said computer system to calculate a matrix of inner products between said signed said N feature vectors and said unknown feature vectors, and multiply said matrix by said vector of scale factors;

determining the discriminant function of said minimum risk linear classification system, using said locus of aggregate risk and said average sign and said geometric locus, said determination of said discriminant function of said minimum risk linear classification system being performed by using said processors of said computer system to subtract said locus of aggregate risk from sum of said geometric locus and said average sign, wherein said discriminant function of said minimum risk linear classification system satisfies said system of fundamental locus equations of binary classification, and wherein said discriminant function of said minimum risk linear classification system determines likely locations of said N feature vectors and also determines said geometric loci of said linear decision boundary and said corresponding decision borders that jointly partition said extreme points into said symmetrical decision regions, wherein said symmetrical decision regions span said overlapping regions or said tail regions of said distributions of said N feature vectors, and wherein said discriminant function of said minimum risk linear classification system satisfies said linear decision boundary in terms of a critical minimum eigenenergy and said minimum expected risk, wherein said counteracting and opposing components of said critical minimum eigenenergies exhibited by said scaled extreme vectors on said geometric locus associated with said corresponding counter risks and risks exhibited by said minimum risk linear classification system are symmetrically distributed over said axis of said dual locus, on equal sides of said statistical fulcrum located at said geometric center of said dual locus, wherein said counteracting and opposing components of said critical minimum eigenenergies together with said corresponding counter risks and risks exhibited by said minimum risk linear system are symmetrically balanced with each other about said geometric center of said dual locus, and wherein said statistical fulcrum is located at said center of said total allowed eigenenergy and said minimum expected risk of said minimum risk linear classification system, wherein said minimum risk linear classification system satisfies a state of statistical equilibrium, wherein said total allowed eigenenergy and said expected risk of said minimum risk linear classification system are minimized, and wherein said minimum risk linear classification system exhibits the minimum probability of error for classifying said N feature vectors and said N test feature vectors related to said data set, wherein said distributions of said feature vectors have similar covariance matrices;

determining which of said two classes said N feature vectors belong to using said discriminant function of said minimum risk linear classification system, said determination of said classes of said N feature vectors being performed by using said processors of said computer system to apply said discriminant function of said minimum risk linear classification system to said N feature vectors, wherein said discriminant function determines likely locations of said N feature vectors and identifies said decision regions related to said two classes that said N feature vectors are located within, wherein said discriminant function recognizes said classes of said N feature vectors, and wherein said minimum risk linear classification system decides which of said two classes said N feature vectors belong to and thereby classifies said N feature vectors;

determining an in-sample classification error rate for said two classes of feature vectors, said determination of said error rate being performed by using said processors of said computer system to calculate the average number of wrong decisions made by said minimum risk linear classification system for classifying said N features vectors;

determining which of said two classes said N test feature vectors belong to using said discriminant function of said minimum risk linear classification system, said determination of said classes of said N test feature vectors being performed by using said processors of said computer system to apply said discriminant function of said minimum risk linear classification system to said N test feature vectors, wherein said discriminant function determines likely locations of said N test feature vectors and identifies said decision regions related to said two classes that said N test feature vectors are located within, wherein said discriminant function recognizes said classes of said N test feature vectors, and wherein said minimum risk linear classification system decides which of said two classes said N test feature vectors belong to and thereby classifies said N test feature vectors;

determining an out-of-sample classification error rate for said two classes of feature vectors, said determination of said error rate being performed by using said processors of said computer system to calculate the average number of wrong decisions made by said minimum risk linear classification system for classifying said N test features vectors;

determining a classification error rate for said two classes of feature vectors, said determination of said classification error rate being performed by using said processors of said computer system to average said in-sample classification error rate and said out-of-sample classification error rate; and determining a measure of overlap between distributions of feature vectors for said two classes of feature vectors using said N feature vectors and said extreme vectors, said determination of said measure of overlap being performed by using said processors of said computer system to calculate the ratio of the number of said extreme vectors to the number of said N feature vectors, wherein said ratio determines said measure of overlap.

6. A computer-implemented method of using feature vectors and machine learning algorithms to determine a discriminant function of a minimum risk linear classification system that classifies collections of said feature vectors into two classes and using said discriminant function of said minimum risk linear classification system to determine if distributions of said collections of said feature vectors are homogenous distributions, said method comprising:

receiving an N×d data set of feature vectors within a computer system, wherein N is a number of feature vectors, d is a number of vector components in each feature vector, and each one of said N feature vectors is labeled with information that identifies which of two collections each one of said N feature vectors belongs to, and wherein each said feature vector is defined by a d-dimensional vector of numerical features, wherein said numerical features are extracted from digital signals;

determining a Gram matrix using said data set, said determination of said Gram matrix being performed by using processors of said computer system to calculate a matrix of all possible inner products of signed said N feature vectors, wherein each one of said N feature vectors has a sign of +1 or −1 that identifies which of said two classes each one of said N feature vectors belongs to, and using said processors of said computer system to calculate a regularized Gram matrix from said Gram matrix;

determining scale factors of a geometric locus of signed and scaled extreme points using said regularized Gram matrix, wherein said extreme points are located within overlapping regions or near tail regions of distributions of said N feature vectors, said determination of said scale factors being performed by using said processors of said computer system to determine a solution of a dual optimization problem, wherein said scale factors and said geometric locus satisfy a system of fundamental locus equations of binary classification, subject to geometric and statistical conditions for a minimum risk linear classification system in statistical equilibrium, and wherein said scale factors determine conditional densities for said extreme points and also determine critical minimum eigenenergies exhibited by scaled extreme vectors on said geometric locus, wherein said critical minimum eigenenergies determine conditional probabilities of said extreme points and also determine corresponding counter risks and risks of a minimum risk linear classification system, wherein said counter risks are associated with right decisions and said risks are associated with wrong decisions of said minimum risk linear classification system, and wherein said geometric locus determines the principal eigenaxis of the decision boundary of said minimum risk linear classification system, wherein said principal eigenaxis exhibits symmetrical dimensions and density, wherein said conditional probabilities and said critical minimum eigenenergies exhibited by said minimum risk linear classification system are symmetrically concentrated within said principal eigenaxis, and wherein counteracting and opposing components of said critical minimum eigenenergies exhibited by said scaled extreme vectors on said geometric locus together with said corresponding counter risks and risks exhibited by said minimum risk linear classification system are symmetrically balanced with each other about the geometric center of said principal eigenaxis, wherein the center of total allowed eigenenergy and minimum expected risk of said minimum risk linear classification system is located at the geometric center of said geometric locus, and wherein said geometric locus determines a primal representation of a dual locus of likelihood components and principal eigenaxis components, wherein said likelihood components and said principal eigenaxis components are symmetrically distributed over either side of the axis of said dual locus, wherein a statistical fulcrum is placed directly under the center of said dual locus, and wherein said likelihood components of said dual locus determine conditional likelihoods for said extreme points, and wherein said principal eigenaxis components of said dual locus determine an intrinsic coordinate system of geometric loci of a linear decision boundary and corresponding decision borders that jointly partition the decision space of said minimum risk linear classification system into symmetrical decision regions;

determining said extreme vectors on said geometric locus using the vector of said scale factors, said determination of said extreme vectors being performed by using said processors of said computer system to identify said scale factors that exceed zero by a small threshold, and using said processors of said computer system to determine a sign vector of signs associated with said extreme vectors using said data set, and compute the average sign using said sign vector;

determining a locus of average risk for said minimum risk linear classification system using said extreme vectors, said determination of said locus of average risk being performed by using said processors of said computer system to calculate the average vector of said extreme vectors;

determining said geometric locus, said determination of said geometric locus being performed by using said processors of said computer system to calculate a matrix of inner products between said signed said N feature vectors and said unknown feature vectors, and multiply said matrix by said vector of scale factors;

determining the discriminant function of said minimum risk linear classification system, using said locus of aggregate risk and said average sign and said geometric locus, said determination of said discriminant function of said minimum risk linear classification system being performed by using said processors of said computer system to subtract said locus of aggregate risk from sum of said geometric locus and said average sign, wherein said discriminant function of said minimum risk linear classification system satisfies said system of fundamental locus equations of binary classification, and wherein said discriminant function of said minimum risk linear classification system determines likely locations of said N feature vectors and also determines said geometric loci of said linear decision boundary and said corresponding decision borders that jointly partition said extreme points into said symmetrical decision regions, wherein said symmetrical decision regions span said overlapping regions or said tail regions of said distributions of said N feature vectors, and wherein said discriminant function of said minimum risk linear classification system satisfies said linear decision boundary in terms of a critical minimum eigenenergy and said minimum expected risk, wherein said counteracting and opposing components of said critical minimum eigenenergies exhibited by said scaled extreme vectors on said geometric locus associated with said corresponding counter risks and risks exhibited by said minimum risk linear classification system are symmetrically distributed over said axis of said dual locus, on equal sides of said statistical fulcrum located at said geometric center of said dual locus, wherein said counteracting and opposing components of said critical minimum eigenenergies together with said corresponding counter risks and risks exhibited by said minimum risk linear system are symmetrically balanced with each other about said geometric center of said dual locus, and wherein said statistical fulcrum is located at said center of said total allowed eigenenergy and said minimum expected risk of said minimum risk linear classification system, wherein said minimum risk linear classification system satisfies a state of statistical equilibrium, wherein said total allowed eigenenergy and said expected risk of said minimum risk linear classification system are minimized, and wherein said minimum risk linear classification system exhibits the minimum probability of error for classifying said N feature vectors and said N test feature vectors related to said data set, wherein said distributions of said feature vectors have similar covariance matrices;

determining which of said two collections said N feature vectors belong to using said discriminant function of said minimum risk linear classification system, said determination of said collections of said N feature vectors being performed by using said processors of said computer system to apply said discriminant function of said minimum risk linear classification system to said N feature vectors, wherein said discriminant function determines likely locations of said N feature vectors and identifies said decision regions related to said two collections that said N feature vectors are located within, wherein said discriminant function recognizes said collections of said N feature vectors, and wherein said minimum risk linear classification system decides which of said two collections said N feature vectors belong to belong to and thereby classifies said N feature vectors;

determining an in-sample classification error rate for said two collections of feature vectors, said determination of said error rate being performed by using said processors of said computer system to calculate the average number of wrong decisions made by said minimum risk linear classification system for classifying said N features vectors;

determining a measure of overlap between said distributions of said N feature vectors for said two collections of feature vectors using said N feature vectors and said extreme vectors, said determination of said measure of overlap being performed by using said processors of said computer system to calculate the ratio of the number of said extreme vectors to the number of said N feature vectors, wherein said ratio determines said measure of overlap; and determining if said distributions of said two collections of said N feature vectors are homogenous distributions using said in-sample classification error rate and said measure of overlap, wherein said distributions of said N feature vectors are homogenous distributions if said measure of overlap has an approximate value of one and said in-sample classification error rate has an approximate value of one half.

* * * * *